US007314864B1

(12) United States Patent
Nishimoto

(10) Patent No.: US 7,314,864 B1
(45) Date of Patent: Jan. 1, 2008

(54) HUMANIN, A POLYPEPTIDE SUPPRESSING NEURONAL DEATH

(75) Inventor: Ikuo Nishimoto, Tokyo (JP)

(73) Assignee: Keio University, Tokyo (JP)

(*) Notice: Subject to any disclaimer, the term of this patent is extended or adjusted under 35 U.S.C. 154(b) by 0 days.

(21) Appl. No.: 10/088,724

(22) PCT Filed: Sep. 14, 2000

(86) PCT No.: PCT/JP00/06314

§ 371 (c)(1),
(2), (4) Date: Jun. 14, 2002

(87) PCT Pub. No.: WO01/21787

PCT Pub. Date: Mar. 29, 2001

(30) Foreign Application Priority Data

Sep. 17, 1999  (JP) ................... 11-264679
Jun. 29, 2000  (JP) ..................... 2000-201456

(51) Int. Cl.
*A61K 38/00* (2006.01)
*A61K 39/00* (2006.01)
*A01N 37/18* (2006.01)
*A01N 63/00* (2006.01)
*C12P 21/06* (2006.01)
*C12P 21/04* (2006.01)
*C07H 21/02* (2006.01)
*C07H 21/04* (2006.01)

(52) U.S. Cl. .............................. 514/12; 514/2; 514/13; 514/14; 530/350; 530/300; 435/69.1; 435/69.7; 435/320.1; 424/93.21; 424/185.1; 424/192.1; 536/23.1; 536/23.4

(58) Field of Classification Search ................ 530/350, 530/300, 325; 536/23.1, 23.5; 435/69.1, 435/320.1; 514/2
See application file for complete search history.

(56) References Cited

FOREIGN PATENT DOCUMENTS

| WO | WO 97/27296 A1 | 7/1997 |
| WO | WO 98/15179 A1 | 4/1998 |
| WO | WO 00/14204 A1 | 3/2000 |
| WO | WO 01/21786 A1 | 3/2001 |
| WO | WO 01/76532 A2 | 10/2001 |

OTHER PUBLICATIONS

Genbank ACC No. AA579497, Sep. 12, 1997.*
Hardy et al., 1998, Science, 282, pp. 1075-1079.*
Offen et al., 2000, J Neural Transm, 58, pp. 153-166.*
Vickers, 2002, Drugs Aging, 19 (7), pp. 487-494.*
Paznekas et al., 1997, Biochem. Biophys. Res. Comm., 238, pp. 1-6.*
Dixon et al., 1997, Hum. Mol. Gen., 6, No. 5, pp. 727-737.*
Brenneman et al., "Activity-Dependant Neurotrophic Factor: Structure-Activity Relationships of Femtomolar-Acting Peptides," *J. Pharmacology Exp. Therapeutics*, 285(2): 619-627 (1998).
Brenneman et al., "A Femtomolar-acting Neuroprotective Peptide," *J. Clinical Investigation*, 97(10): 2299-2307 (1996).
Dore et al., "Insulin-like growth factor I protects and rescues hippocampal neurons against β-amyloid- and human amylin-induced toxicity," *PNAS*, 94:4772-4777 (1997).
Guo et al., "Calbindin D28k blocks the proapoptotic actions of mutant presenilin 1: Reduced oxidative stress and preserved mitochondrial function," *PNAS*, 95: 3227-3232 (1998).
Guo et al., "Secreted β-Amyloid Precursor Protein Counteracts the Proapoptotic Action of Mutant Presenilin-1 by Activation of NF—ηB and Stabilization of Calcium Homeostasis*," *J. Biological Chemistry*, 273(20):12341-12351 (1998).
Mark et al., "Basic FGF attenuates amyloid β-peptide-induced oxidative stress, mitchondrial dysfunction, and impairment of Na+/K+-ATPase activity in hippocampal neurons," *Brain Research*, 756:205-214 (1997).
XP-02230776, "Homo sapiens mitochondrial DNA, complete genome," (2000).
Mattson et al., "Estrogens stabilize mitochondrial function and protect neural cells against the pro-apoptotic action of mutant presenilin-1," *NeuroReport*, 8:3817-3821 (1997).
Hashimoto et al., "A rescue factor abolishing neuronal cell death by a wide spectrum of familial Alzheimer's disease genes and Aβ" *Proceedings of the National Academy of Science* (May 22, 2001) 98(11):6336-6341.
Mamiya and Ukal, "[Gly$^{14}$]-Humanin improved the learning and memory impairment induced by scopolamine in vivo" *British Journal of Pharmacology* (2001) 134:1597-1599.
Tajima et al. "Humanin derivative, S14G-HN, prevents amyloid-beta-induced memory impairment in mice." J Neurosci Res. (Mar. 1, 2005), 79(5):714-23.

(Continued)

*Primary Examiner*—Olga N. Chernyshev
(74) *Attorney, Agent, or Firm*—Townsend and Townsend and Crew LLP

(57) ABSTRACT

The present invention provides polypeptides that suppresses neuronal death associated with Alzheimer's disease. Using a neuronal cell system, wherein the expression of familial Alzheimer's disease mutant APP can be induced by ecdysone treatment, a gene that protects the neurons from cell death was successfully isolated. The gene encodes a secretory polypeptide consisting of 24 amino acids, and this polypeptide suppresses neuronal death caused by the expression of APP mutants and presenilin mutants. The polypeptide also suppressed cell death of primary neuronal culture caused by Aβ. Furthermore, by mutating the amino acids of the polypeptide, the neuronal death suppression activity of the polypwptide was successfully and significantly enhanced. These polypeptides and derivatives thereof are useful as pharmaceuticals to prevent neuronal death associated with Alzheimer's disease, and as seed compounds for developing novel pharmaceuticals for Alzheimer's disease.

21 Claims, 25 Drawing Sheets

OTHER PUBLICATIONS

Loo et al. "Apoptosis is induced by beta-amyloid in cultured central nervous system neurons." Proc Natl Acad Sci U S A. Sep. 1, 1993), 90(17):7951-5.

Haley TG, McCormick WG. "Pharmacological effects produced by intracerebral injection of drugs in the conscious mouse." (1957) Br J Pharmacol 12:12-15.IDS.

* cited by examiner

Figure 19C
Figure 19D
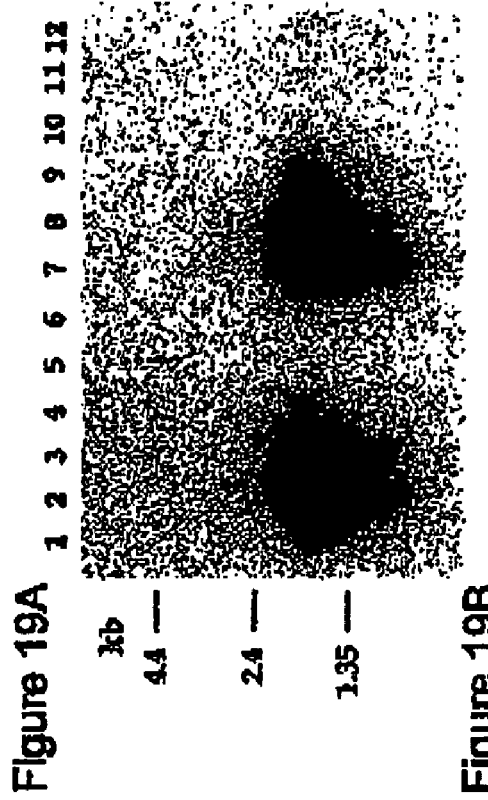
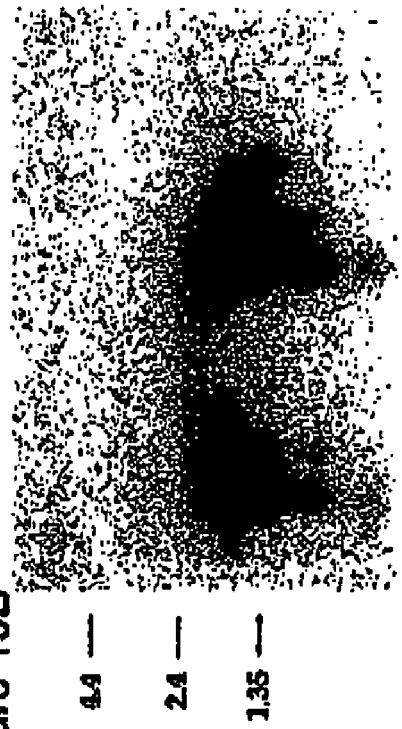
Figure 19A
Figure 19B

Figure 21

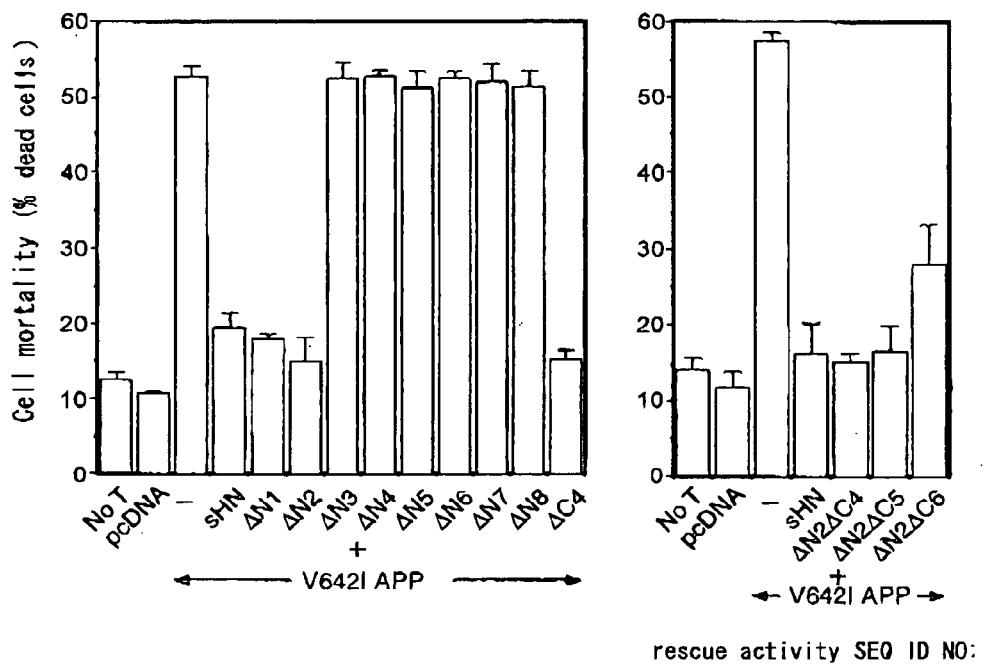

| | | rescue activity | SEQ ID NO: |
|---|---|---|---|
| Humanin: | MAPRGFSCLLLLTSEIDLPVKRRA | ++ | 5 |
| ΔN₁-Humanin: | APRGFSCLLLLTSEIDLPVKRRA | ++ | 12 |
| ΔN₂-Humanin: | PRGFSCLLLLTSEIDLPVKRRA | ++ | 13 |
| ΔN₃-Humanin: | RGFSCLLLLTSEIDLPVKRRA | - | 14 |
| ΔN₄-Humanin: | GFSCLLLLTSEIDLPVKRRA | - | 15 |
| ΔN₅-Humanin: | FSCLLLLTSEIDLPVKRRA | - | 16 |
| ΔN₆-Humanin: | SCLLLLTSEIDLPVKRRA | - | 17 |
| ΔN₇-Humanin: | CLLLLTSEIDLPVKRRA | - | 18 |
| ΔN₈-Humanin: | LLLLTSEIDLPVKRRA | - | 19 |
| ΔN₃ΔC₆-Humanin: | PRGFSCLLLLTSEIDL | + | 20 |
| ΔN₂ΔC₅-Humanin: | PRGFSCLLLLTSEIDLP | ++ | 21 |
| ΔN₂ΔC₄-Humanin: | PRGFSCLLLLTSEIDLPV | ++ | 22 |
| ΔN₂-Humanin: | PRGFSCLLLLTSEIDLPVKRRA | ++ | 13 |
| ΔC₄-Humanin: | MAPRGFSCLLLLTSEIDLPV | ++ | 23 |

SEQUENCE LISTING

```
<160> NUMBER OF SEQ ID NOS: 102

<210> SEQ ID NO 1
<211> LENGTH: 85
<212> TYPE: DNA
<213> ORGANISM: Artificial
<220> FEATURE:
<223> OTHER INFORMATION: artificially synthesized sequence

<400> SEQUENCE: 1
aattcaccat ggctccacga gggttcagct gtctcttact tttaaccagt gaaattgacc      60
tgcccgtgaa gaggcgggca ggtac                                           85

<210> SEQ ID NO 2
<211> LENGTH: 77
<212> TYPE: DNA
<213> ORGANISM: Artificial
<220> FEATURE:
<223> OTHER INFORMATION: artificially synthesized sequence

<400> SEQUENCE: 2
ctgcccgcct cttcacgggc aggtcaattt cactggttaa aagtaagaga cagctgaacc      60
ctcgtggagc catggtg                                                    77

<210> SEQ ID NO 3
<211> LENGTH: 79
<212> TYPE: DNA
<213> ORGANISM: Artificial
<220> FEATURE:
<223> OTHER INFORMATION: artificially synthesized sequence

<400> SEQUENCE: 3
ctgcccgcct cttcacgggc aggtcaattt cactggttaa aagtaagaga cagctgaacc      60
ctcgtggagc catgtggtg                                                  79

<210> SEQ ID NO 4
<211> LENGTH: 75
<212> TYPE: DNA
<213> ORGANISM: Homo sapiens
<220> FEATURE:
<221> NAME/KEY: CDS
<222> LOCATION: (1)..(72)
<223> OTHER INFORMATION:

<400> SEQUENCE: 4 atg gct cca cga ggg ttc agc tgt ctc tta ctt tta acc agt gaa att      48
Met Ala Pro Arg Gly Phe Ser Cys Leu Leu Leu Leu Thr Ser Glu Ile
1               5                   10                  15 gac ctg ccc gtg aag agg cgg gca tga                                   75
Asp Leu Pro Val Lys Arg Arg Ala
            20

<210> SEQ ID NO 5
<211> LENGTH: 24
<212> TYPE: PRT
<213> ORGANISM: Homo sapiens

<400> SEQUENCE: 5
```

-continued

```
Met Ala Pro Arg Gly Phe Ser Cys Leu Leu Leu Thr Ser Glu Ile
1               5                   10                  15

Asp Leu Pro Val Lys Arg Arg Ala
            20

<210> SEQ ID NO 6
<211> LENGTH: 34
<212> TYPE: PRT
<213> ORGANISM: Artificial
<220> FEATURE:
<223> OTHER INFORMATION: artificially synthesized sequence (sHN-FLAG)

<400> SEQUENCE: 6

Met Ala Pro Arg Gly Phe Ser Cys Leu Leu Leu Thr Ser Glu Ile
1               5                   10                  15

Asp Leu Pro Val Lys Arg Arg Ala Gly Thr Asp Tyr Lys Asp Asp
            20                  25                  30

Asp Lys

<210> SEQ ID NO 7
<211> LENGTH: 24
<212> TYPE: PRT
<213> ORGANISM: Artificial
<220> FEATURE:
<223> OTHER INFORMATION: artificially synthesized sequence (HNR)

<400> SEQUENCE: 7

Met Ala Pro Arg Gly Phe Ser Cys Arg Leu Leu Thr Ser Glu Ile
1               5                   10                  15

Asp Leu Pro Val Lys Arg Arg Ala
            20

<210> SEQ ID NO 8
<211> LENGTH: 24
<212> TYPE: PRT
<213> ORGANISM: Artificial
<220> FEATURE:
<223> OTHER INFORMATION: artificially synthesized sequence (HNG)

<400> SEQUENCE: 8

Met Ala Pro Arg Gly Phe Ser Cys Leu Leu Leu Thr Gly Glu Ile
1               5                   10                  15

Asp Leu Pro Val Lys Arg Arg Ala
            20

<210> SEQ ID NO 9
<211> LENGTH: 24
<212> TYPE: PRT
<213> ORGANISM: Artificial
<220> FEATURE:
<223> OTHER INFORMATION: artificially synthesized sequence (HNA)

<400> SEQUENCE: 9

Met Ala Pro Arg Gly Phe Ser Ala Leu Leu Leu Thr Ser Glu Ile
1               5                   10                  15

Asp Leu Pro Val Lys Arg Arg Ala
            20

<210> SEQ ID NO 10
<211> LENGTH: 24
<212> TYPE: PRT
<213> ORGANISM: Artificial
<220> FEATURE:
<223> OTHER INFORMATION: artificially synthesized sequence
```

```
<400> SEQUENCE: 10

Met Ala Pro Arg Gly Phe Ser Cys Leu Leu Leu Leu Thr Ser Glu Ile
1               5                   10                  15

Asp Leu Pro Val Ala Ala Ala Ala
            20

<210> SEQ ID NO 11
<211> LENGTH: 19
<212> TYPE: DNA
<213> ORGANISM: Artificial
<220> FEATURE:
<223> OTHER INFORMATION: artificially synthesized sequence

<400> SEQUENCE: 11
gggtgttgag cttgaacgc                                              19

<210> SEQ ID NO 12
<211> LENGTH: 23
<212> TYPE: PRT
<213> ORGANISM: Artificial
<220> FEATURE:
<223> OTHER INFORMATION: artificially synthesized sequence
      (deltaN1-Humanin)

<400> SEQUENCE: 12

Ala Pro Arg Gly Phe Ser Cys Leu Leu Leu Leu Thr Ser Glu Ile Asp
1               5                   10                  15

Leu Pro Val Lys Arg Arg Ala
            20

<210> SEQ ID NO 13
<211> LENGTH: 22
<212> TYPE: PRT
<213> ORGANISM: Artificial
<220> FEATURE:
<223> OTHER INFORMATION: artificially synthesized sequence
      (deltaN2-Humanin)

<400> SEQUENCE: 13

Pro Arg Gly Phe Ser Cys Leu Leu Leu Leu Thr Ser Glu Ile Asp Leu
1               5                   10                  15

Pro Val Lys Arg Arg Ala
            20

<210> SEQ ID NO 14
<211> LENGTH: 21
<212> TYPE: PRT
<213> ORGANISM: Artificial
<220> FEATURE:
<223> OTHER INFORMATION: artificially synthesized sequence
      (deltaN3-Humanin)

<400> SEQUENCE: 14

Arg Gly Phe Ser Cys Leu Leu Leu Leu Thr Ser Glu Ile Asp Leu Pro
1               5                   10                  15

Val Lys Arg Arg Ala
            20

<210> SEQ ID NO 15
<211> LENGTH: 20
<212> TYPE: PRT
<213> ORGANISM: Artificial
<220> FEATURE:
<223> OTHER INFORMATION: artificially synthesized sequence
```

(deltaN4-Humanin)

<400> SEQUENCE: 15

Gly Phe Ser Cys Leu Leu Leu Thr Ser Glu Ile Asp Leu Pro Val
1               5                   10                  15

Lys Arg Arg Ala
            20

<210> SEQ ID NO 16
<211> LENGTH: 19
<212> TYPE: PRT
<213> ORGANISM: Artificial
<220> FEATURE:
<223> OTHER INFORMATION: artificially synthesized sequence
      (deltaN5-Humanin)

<400> SEQUENCE: 16

Phe Ser Cys Leu Leu Leu Thr Ser Glu Ile Asp Leu Pro Val Lys
1               5                   10                  15

Arg Arg Ala

<210> SEQ ID NO 17
<211> LENGTH: 18
<212> TYPE: PRT
<213> ORGANISM: Artificial
<220> FEATURE:
<223> OTHER INFORMATION: artificially synthesized sequence
      (deltaN6-Humanin)

<400> SEQUENCE: 17

Ser Cys Leu Leu Leu Leu Thr Ser Glu Ile Asp Leu Pro Val Lys Arg
1               5                   10                  15

Arg Ala

<210> SEQ ID NO 18
<211> LENGTH: 17
<212> TYPE: PRT
<213> ORGANISM: Artificial
<220> FEATURE:
<223> OTHER INFORMATION: artificially synthesized sequence
      (deltaN7-Humanin)

<400> SEQUENCE: 18

Cys Leu Leu Leu Leu Thr Ser Glu Ile Asp Leu Pro Val Lys Arg Arg
1               5                   10                  15

Ala

<210> SEQ ID NO 19
<211> LENGTH: 16
<212> TYPE: PRT
<213> ORGANISM: Artificial
<220> FEATURE:
<223> OTHER INFORMATION: artificially synthesized sequence
      (deltaN8-Humanin)

<400> SEQUENCE: 19

Leu Leu Leu Leu Thr Ser Glu Ile Asp Leu Pro Val Lys Arg Arg Ala
1               5                   10                  15

<210> SEQ ID NO 20
<211> LENGTH: 16
<212> TYPE: PRT
<213> ORGANISM: Artificial
<220> FEATURE:
<223> OTHER INFORMATION: artificially synthesized sequence (deltaN2 deltaC6-Humanin)

<400> SEQUENCE: 20

Pro Arg Gly Phe Ser Cys Leu Leu Leu Leu Thr Ser Glu Ile Asp Leu
1               5                   10                  15

<210> SEQ ID NO 21
<211> LENGTH: 17
<212> TYPE: PRT
<213> ORGANISM: Artificial
<220> FEATURE:
<223> OTHER INFORMATION: artificially synthesized sequence
      (deltaN2 deltaC5-Humanin; HN-17
      )

<400> SEQUENCE: 21

Pro Arg Gly Phe Ser Cys Leu Leu Leu Leu Thr Ser Glu Ile Asp Leu
1               5                   10                  15

Pro

<210> SEQ ID NO 22
<211> LENGTH: 18
<212> TYPE: PRT
<213> ORGANISM: Artificial
<220> FEATURE:
<223> OTHER INFORMATION: artificially synthesized sequence
      (deltaN2 deltaC4-Humanin)

<400> SEQUENCE: 22

Pro Arg Gly Phe Ser Cys Leu Leu Leu Leu Thr Ser Glu Ile Asp Leu
1               5                   10                  15

Pro Val

<210> SEQ ID NO 23
<211> LENGTH: 20
<212> TYPE: PRT
<213> ORGANISM: Artificial
<220> FEATURE:
<223> OTHER INFORMATION: artificially synthesized sequence
      (deltaC4-Humanin)

<400> SEQUENCE: 23

Met Ala Pro Arg Gly Phe Ser Cys Leu Leu Leu Leu Thr Ser Glu Ile
1               5                   10                  15

Asp Leu Pro Val
            20

<210> SEQ ID NO 24
<211> LENGTH: 17
<212> TYPE: PRT
<213> ORGANISM: Artificial
<220> FEATURE:
<223> OTHER INFORMATION: artificially synthesized sequence (HNG-17)

<400> SEQUENCE: 24

Pro Arg Gly Phe Ser Cys Leu Leu Leu Leu Thr Gly Glu Ile Asp Leu
1               5                   10                  15

Pro

<210> SEQ ID NO 25
<211> LENGTH: 17
<212> TYPE: PRT
<213> ORGANISM: Artificial
<220> FEATURE:
<223> OTHER INFORMATION: artificially synthesized sequence

```
<400> SEQUENCE: 25

Ala Arg Gly Phe Ser Cys Leu Leu Leu Thr Gly Glu Ile Asp Leu
1               5                   10                  15

Pro

<210> SEQ ID NO 26
<211> LENGTH: 17
<212> TYPE: PRT
<213> ORGANISM: Artificial
<220> FEATURE:
<223> OTHER INFORMATION: artificially synthesized sequence

<400> SEQUENCE: 26

Pro Ala Gly Phe Ser Cys Leu Leu Leu Thr Gly Glu Ile Asp Leu
1               5                   10                  15

Pro

<210> SEQ ID NO 27
<211> LENGTH: 17
<212> TYPE: PRT
<213> ORGANISM: Artificial
<220> FEATURE:
<223> OTHER INFORMATION: artificially synthesized sequence

<400> SEQUENCE: 27

Pro Arg Ala Phe Ser Cys Leu Leu Leu Thr Gly Glu Ile Asp Leu
1               5                   10                  15

Pro

<210> SEQ ID NO 28
<211> LENGTH: 17
<212> TYPE: PRT
<213> ORGANISM: Artificial
<220> FEATURE:
<223> OTHER INFORMATION: artificially synthesized sequence

<400> SEQUENCE: 28

Pro Arg Gly Ala Ser Cys Leu Leu Leu Thr Gly Glu Ile Asp Leu
1               5                   10                  15

Pro

<210> SEQ ID NO 29
<211> LENGTH: 17
<212> TYPE: PRT
<213> ORGANISM: Artificial
<220> FEATURE:
<223> OTHER INFORMATION: artificially synthesized sequence

<400> SEQUENCE: 29

Pro Arg Gly Phe Ala Cys Leu Leu Leu Thr Gly Glu Ile Asp Leu
1               5                   10                  15

Pro

<210> SEQ ID NO 30
<211> LENGTH: 17
<212> TYPE: PRT
<213> ORGANISM: Artificial
<220> FEATURE:
<223> OTHER INFORMATION: artificially synthesized sequence

<400> SEQUENCE: 30

Pro Arg Gly Phe Ser Ala Leu Leu Leu Leu Thr Gly Glu Ile Asp Leu
```

```
                1               5                  10                  15
Pro

<210> SEQ ID NO 31
<211> LENGTH: 17
<212> TYPE: PRT
<213> ORGANISM: Artificial
<220> FEATURE:
<223> OTHER INFORMATION: artificially synthesized sequence

<400> SEQUENCE: 31

Pro Arg Gly Phe Ser Cys Ala Leu Leu Leu Thr Gly Glu Ile Asp Leu
1               5                   10                  15
Pro

<210> SEQ ID NO 32
<211> LENGTH: 17
<212> TYPE: PRT
<213> ORGANISM: Artificial
<220> FEATURE:
<223> OTHER INFORMATION: artificially synthesized sequence

<400> SEQUENCE: 32

Pro Arg Gly Phe Ser Cys Leu Ala Leu Leu Thr Gly Glu Ile Asp Leu
1               5                   10                  15
Pro

<210> SEQ ID NO 33
<211> LENGTH: 17
<212> TYPE: PRT
<213> ORGANISM: Artificial
<220> FEATURE:
<223> OTHER INFORMATION: artificially synthesized sequence

<400> SEQUENCE: 33

Pro Arg Gly Phe Ser Cys Leu Leu Ala Leu Thr Gly Glu Ile Asp Leu
1               5                   10                  15
Pro

<210> SEQ ID NO 34
<211> LENGTH: 17
<212> TYPE: PRT
<213> ORGANISM: Artificial
<220> FEATURE:
<223> OTHER INFORMATION: artificially synthesized sequence

<400> SEQUENCE: 34

Pro Arg Gly Phe Ser Cys Leu Leu Leu Ala Thr Gly Glu Ile Asp Leu
1               5                   10                  15
Pro

<210> SEQ ID NO 35
<211> LENGTH: 17
<212> TYPE: PRT
<213> ORGANISM: Artificial
<220> FEATURE:
<223> OTHER INFORMATION: artificially synthesized sequence

<400> SEQUENCE: 35

Pro Arg Gly Phe Ser Cys Leu Leu Leu Leu Ala Gly Glu Ile Asp Leu
1               5                   10                  15
Pro
```

<210> SEQ ID NO 36
<211> LENGTH: 17
<212> TYPE: PRT
<213> ORGANISM: Artificial
<220> FEATURE:
<223> OTHER INFORMATION: artificially synthesized sequence

<400> SEQUENCE: 36

Pro Arg Gly Phe Ser Cys Leu Leu Leu Leu Thr Ala Glu Ile Asp Leu
1               5                   10                  15

Pro

<210> SEQ ID NO 37
<211> LENGTH: 17
<212> TYPE: PRT
<213> ORGANISM: Artificial
<220> FEATURE:
<223> OTHER INFORMATION: artificially synthesized sequence

<400> SEQUENCE: 37

Pro Arg Gly Phe Ser Cys Leu Leu Leu Leu Thr Gly Ala Ile Asp Leu
1               5                   10                  15

Pro

<210> SEQ ID NO 38
<211> LENGTH: 17
<212> TYPE: PRT
<213> ORGANISM: Artificial
<220> FEATURE:
<223> OTHER INFORMATION: artificially synthesized sequence

<400> SEQUENCE: 38

Pro Arg Gly Phe Ser Cys Leu Leu Leu Leu Thr Gly Glu Ala Asp Leu
1               5                   10                  15

Pro

<210> SEQ ID NO 39
<211> LENGTH: 17
<212> TYPE: PRT
<213> ORGANISM: Artificial
<220> FEATURE:
<223> OTHER INFORMATION: artificially synthesized sequence

<400> SEQUENCE: 39

Pro Arg Gly Phe Ser Cys Leu Leu Leu Leu Thr Gly Glu Ile Ala Leu
1               5                   10                  15

Pro

<210> SEQ ID NO 40
<211> LENGTH: 17
<212> TYPE: PRT
<213> ORGANISM: Artificial
<220> FEATURE:
<223> OTHER INFORMATION: artificially synthesized sequence

<400> SEQUENCE: 40

Pro Arg Gly Phe Ser Cys Leu Leu Leu Leu Thr Gly Glu Ile Asp Ala
1               5                   10                  15

Pro

<210> SEQ ID NO 41
<211> LENGTH: 17
<212> TYPE: PRT

<213> ORGANISM: Artificial
<220> FEATURE:
<223> OTHER INFORMATION: artificially synthesized sequence

<400> SEQUENCE: 41

Pro Arg Gly Phe Ser Cys Leu Leu Leu Thr Gly Glu Ile Asp Leu
1               5                   10                  15
Ala

<210> SEQ ID NO 42
<211> LENGTH: 24
<212> TYPE: PRT
<213> ORGANISM: Artificial
<220> FEATURE:
<223> OTHER INFORMATION: artificially synthesized sequence

<400> SEQUENCE: 42

Met Ala Pro Arg Gly Phe Ser Asp Leu Leu Leu Thr Gly Glu Ile
1               5                   10                  15

Asp Leu Pro Val Lys Arg Arg Ala
            20

<210> SEQ ID NO 43
<211> LENGTH: 24
<212> TYPE: PRT
<213> ORGANISM: Artificial
<220> FEATURE:
<223> OTHER INFORMATION: artificially synthesized sequence

<400> SEQUENCE: 43

Met Ala Pro Arg Gly Phe Ser Glu Leu Leu Leu Thr Gly Glu Ile
1               5                   10                  15

Asp Leu Pro Val Lys Arg Arg Ala
            20

<210> SEQ ID NO 44
<211> LENGTH: 24
<212> TYPE: PRT
<213> ORGANISM: Artificial
<220> FEATURE:
<223> OTHER INFORMATION: artificially synthesized sequence

<400> SEQUENCE: 44

Met Ala Pro Arg Gly Phe Ser Phe Leu Leu Leu Thr Gly Glu Ile
1               5                   10                  15

Asp Leu Pro Val Lys Arg Arg Ala
            20

<210> SEQ ID NO 45
<211> LENGTH: 24
<212> TYPE: PRT
<213> ORGANISM: Artificial
<220> FEATURE:
<223> OTHER INFORMATION: artificially synthesized sequence

<400> SEQUENCE: 45

Met Ala Pro Arg Gly Phe Ser Gly Leu Leu Leu Thr Gly Glu Ile
1               5                   10                  15

Asp Leu Pro Val Lys Arg Arg Ala
            20

<210> SEQ ID NO 46
<211> LENGTH: 24
<212> TYPE: PRT

<213> ORGANISM: Artificial
<220> FEATURE:
<223> OTHER INFORMATION: artificially synthesized sequence

<400> SEQUENCE: 46

Met Ala Pro Arg Gly Phe Ser His Leu Leu Leu Leu Thr Gly Glu Ile
1               5                   10                  15

Asp Leu Pro Val Lys Arg Arg Ala
            20

<210> SEQ ID NO 47
<211> LENGTH: 24
<212> TYPE: PRT
<213> ORGANISM: Artificial
<220> FEATURE:
<223> OTHER INFORMATION: artificially synthesized sequence

<400> SEQUENCE: 47

Met Ala Pro Arg Gly Phe Ser Ile Leu Leu Leu Leu Thr Gly Glu Ile
1               5                   10                  15

Asp Leu Pro Val Lys Arg Arg Ala
            20

<210> SEQ ID NO 48
<211> LENGTH: 24
<212> TYPE: PRT
<213> ORGANISM: Artificial
<220> FEATURE:
<223> OTHER INFORMATION: artificially synthesized sequence

<400> SEQUENCE: 48

Met Ala Pro Arg Gly Phe Ser Lys Leu Leu Leu Leu Thr Gly Glu Ile
1               5                   10                  15

Asp Leu Pro Val Lys Arg Arg Ala
            20

<210> SEQ ID NO 49
<211> LENGTH: 24
<212> TYPE: PRT
<213> ORGANISM: Artificial
<220> FEATURE:
<223> OTHER INFORMATION: artificially synthesized sequence

<400> SEQUENCE: 49

Met Ala Pro Arg Gly Phe Ser Leu Leu Leu Leu Leu Thr Gly Glu Ile
1               5                   10                  15

Asp Leu Pro Val Lys Arg Arg Ala
            20

<210> SEQ ID NO 50
<211> LENGTH: 24
<212> TYPE: PRT
<213> ORGANISM: Artificial
<220> FEATURE:
<223> OTHER INFORMATION: artificially synthesized sequence

<400> SEQUENCE: 50

Met Ala Pro Arg Gly Phe Ser Met Leu Leu Leu Leu Thr Gly Glu Ile
1               5                   10                  15

Asp Leu Pro Val Lys Arg Arg Ala
            20

<210> SEQ ID NO 51
<211> LENGTH: 24

```
<212> TYPE: PRT
<213> ORGANISM: Artificial
<220> FEATURE:
<223> OTHER INFORMATION: artificially synthesized sequence

<400> SEQUENCE: 51

Met Ala Pro Arg Gly Phe Ser Asn Leu Leu Leu Thr Gly Glu Ile
1               5                   10                  15

Asp Leu Pro Val Lys Arg Arg Ala
            20

<210> SEQ ID NO 52
<211> LENGTH: 24
<212> TYPE: PRT
<213> ORGANISM: Artificial
<220> FEATURE:
<223> OTHER INFORMATION: artificially synthesized sequence

<400> SEQUENCE: 52

Met Ala Pro Arg Gly Phe Ser Pro Leu Leu Leu Thr Gly Glu Ile
1               5                   10                  15

Asp Leu Pro Val Lys Arg Arg Ala
            20

<210> SEQ ID NO 53
<211> LENGTH: 24
<212> TYPE: PRT
<213> ORGANISM: Artificial
<220> FEATURE:
<223> OTHER INFORMATION: artificially synthesized sequence

<400> SEQUENCE: 53

Met Ala Pro Arg Gly Phe Ser Gln Leu Leu Leu Thr Gly Glu Ile
1               5                   10                  15

Asp Leu Pro Val Lys Arg Arg Ala
            20

<210> SEQ ID NO 54
<211> LENGTH: 24
<212> TYPE: PRT
<213> ORGANISM: Artificial
<220> FEATURE:
<223> OTHER INFORMATION: artificially synthesized sequence

<400> SEQUENCE: 54

Met Ala Pro Arg Gly Phe Ser Arg Leu Leu Leu Thr Gly Glu Ile
1               5                   10                  15

Asp Leu Pro Val Lys Arg Arg Ala
            20

<210> SEQ ID NO 55
<211> LENGTH: 24
<212> TYPE: PRT
<213> ORGANISM: Artificial
<220> FEATURE:
<223> OTHER INFORMATION: artificially synthesized sequence

<400> SEQUENCE: 55

Met Ala Pro Arg Gly Phe Ser Ser Leu Leu Leu Thr Gly Glu Ile
1               5                   10                  15

Asp Leu Pro Val Lys Arg Arg Ala
            20

<210> SEQ ID NO 56
```

```
-continued

<211> LENGTH: 24
<212> TYPE: PRT
<213> ORGANISM: Artificial
<220> FEATURE:
<223> OTHER INFORMATION: artificially synthesized sequence

<400> SEQUENCE: 56

Met Ala Pro Arg Gly Phe Ser Thr Leu Leu Leu Thr Gly Glu Ile
1               5                   10                  15

Asp Leu Pro Val Lys Arg Arg Ala
            20

<210> SEQ ID NO 57
<211> LENGTH: 24
<212> TYPE: PRT
<213> ORGANISM: Artificial
<220> FEATURE:
<223> OTHER INFORMATION: artificially synthesized sequence

<400> SEQUENCE: 57

Met Ala Pro Arg Gly Phe Ser Val Leu Leu Leu Thr Gly Glu Ile
1               5                   10                  15

Asp Leu Pro Val Lys Arg Arg Ala
            20

<210> SEQ ID NO 58
<211> LENGTH: 24
<212> TYPE: PRT
<213> ORGANISM: Artificial
<220> FEATURE:
<223> OTHER INFORMATION: artificially synthesized sequence

<400> SEQUENCE: 58

Met Ala Pro Arg Gly Phe Ser Trp Leu Leu Leu Thr Gly Glu Ile
1               5                   10                  15

Asp Leu Pro Val Lys Arg Arg Ala
            20

<210> SEQ ID NO 59
<211> LENGTH: 24
<212> TYPE: PRT
<213> ORGANISM: Artificial
<220> FEATURE:
<223> OTHER INFORMATION: artificially synthesized sequence

<400> SEQUENCE: 59

Met Ala Pro Arg Gly Phe Ser Tyr Leu Leu Leu Thr Gly Glu Ile
1               5                   10                  15

Asp Leu Pro Val Lys Arg Arg Ala
            20

<210> SEQ ID NO 60
<211> LENGTH: 24
<212> TYPE: PRT
<213> ORGANISM: Artificial
<220> FEATURE:
<223> OTHER INFORMATION: artificially synthesized sequence (AGA-HN)

<400> SEQUENCE: 60

Met Ala Pro Ala Gly Ala Ser Cys Leu Leu Leu Thr Gly Glu Ile
1               5                   10                  15

Asp Leu Pro Val Lys Arg Arg Ala
            20
```

```
<210> SEQ ID NO 61
<211> LENGTH: 8
<212> TYPE: PRT
<213> ORGANISM: Artificial
<220> FEATURE:
<223> OTHER INFORMATION: artificially synthesized sequence

<400> SEQUENCE: 61

Asp Tyr Lys Asp Asp Asp Asp Lys
1               5

<210> SEQ ID NO 62
<211> LENGTH: 4
<212> TYPE: PRT
<213> ORGANISM: Homo sapiens

<400> SEQUENCE: 62

Lys Arg Arg Ala
1

<210> SEQ ID NO 63
<211> LENGTH: 10
<212> TYPE: PRT
<213> ORGANISM: Artificial
<220> FEATURE:
<223> OTHER INFORMATION: artificially synthesized sequence
<220> FEATURE:
<221> NAME/KEY: MISC_FEATURE
<222> LOCATION: (2)..(2)
<223> OTHER INFORMATION: "Xaa" indicate arbitrary amino acids not more
      than 10 residues.
<220> FEATURE:
<221> NAME/KEY: MISC_FEATURE
<222> LOCATION: (3)..(3)
<223> OTHER INFORMATION: "Xaa" indicates Cys or a basic amino acid.
<220> FEATURE:
<221> NAME/KEY: MISC_FEATURE
<222> LOCATION: (4)..(4)
<223> OTHER INFORMATION: "Xaa" indicates Leu or Arg.
<220> FEATURE:
<221> NAME/KEY: MISC_FEATURE
<222> LOCATION: (5)..(5)
<223> OTHER INFORMATION: "Xaa" indicate arbitrary amino acids not more
      than 10 residues.
<220> FEATURE:
<221> NAME/KEY: MISC_FEATURE
<222> LOCATION: (8)..(8)
<223> OTHER INFORMATION: "Xaa" indicate Gly or Ser.
<220> FEATURE:
<221> NAME/KEY: MISC_FEATURE
<222> LOCATION: (9)..(9)
<223> OTHER INFORMATION: "Xaa" indicate arbitrary amino acids not more
      than 10 residues.

<400> SEQUENCE: 63

Pro Xaa Xaa Xaa Xaa Leu Thr Xaa Xaa Pro
1               5                   10

<210> SEQ ID NO 64
<211> LENGTH: 10
<212> TYPE: PRT
<213> ORGANISM: Artificial
<220> FEATURE:
<223> OTHER INFORMATION: artificially synthesized sequence
<220> FEATURE:
<221> NAME/KEY: MISC_FEATURE
<222> LOCATION: (2)..(2)
<223> OTHER INFORMATION: "Xaa" indicates 1 to 10 residues of arbitrary
      amino acids.
<220> FEATURE:
<221> NAME/KEY: MISC_FEATURE
<222> LOCATION: (3)..(3)
<223> OTHER INFORMATION: "Xaa" indicates Cys or a basic amino acid.
```

```
<220> FEATURE:
<221> NAME/KEY: MISC_FEATURE
<222> LOCATION: (4)..(4)
<223> OTHER INFORMATION: "Xaa" indicates Leu or Arg.
<220> FEATURE:
<221> NAME/KEY: MISC_FEATURE
<222> LOCATION: (5)..(5)
<223> OTHER INFORMATION: "Xaa" indicates 1 to 10 residues of arbitrary
      amino acids.
<220> FEATURE:
<221> NAME/KEY: MISC_FEATURE
<222> LOCATION: (8)..(8)
<223> OTHER INFORMATION: "Xaa" indicates Gly or Ser.
<220> FEATURE:
<221> NAME/KEY: MISC_FEATURE
<222> LOCATION: (9)..(9)
<223> OTHER INFORMATION: "Xaa" indicates 1 to 10 residues of arbitrary
      amino acids.

<400> SEQUENCE: 64

Pro Xaa Xaa Xaa Xaa Leu Thr Xaa Xaa Pro
1               5                   10

<210> SEQ ID NO 65
<211> LENGTH: 10
<212> TYPE: PRT
<213> ORGANISM: Artificial
<220> FEATURE:
<223> OTHER INFORMATION: artificially synthesized sequence
<220> FEATURE:
<221> NAME/KEY: MISC_FEATURE
<222> LOCATION: (2)..(2)
<223> OTHER INFORMATION: "Xaa" indicate arbitrary amino acids not more
      than 10 residues.
<220> FEATURE:
<221> NAME/KEY: MISC_FEATURE
<222> LOCATION: (3)..(3)
<223> OTHER INFORMATION: "Xaa" indicates Cys, Arg, Lys, or His.
<220> FEATURE:
<221> NAME/KEY: MISC_FEATURE
<222> LOCATION: (4)..(4)
<223> OTHER INFORMATION: "Xaa" indicates Leu or Arg.
<220> FEATURE:
<221> NAME/KEY: MISC_FEATURE
<222> LOCATION: (5)..(5)
<223> OTHER INFORMATION: "Xaa" indicate arbitrary amino acids not more
      than 10 residues.
<220> FEATURE:
<221> NAME/KEY: MISC_FEATURE
<222> LOCATION: (8)..(8)
<223> OTHER INFORMATION: "Xaa" indicates Gly or Ser.
<220> FEATURE:
<221> NAME/KEY: MISC_FEATURE
<222> LOCATION: (9)..(9)
<223> OTHER INFORMATION: "Xaa" indicate arbitrary amino acids not more
      than 10 residues.

<400> SEQUENCE: 65

Pro Xaa Xaa Xaa Xaa Leu Thr Xaa Xaa Pro
1               5                   10

<210> SEQ ID NO 66
<211> LENGTH: 4
<212> TYPE: PRT
<213> ORGANISM: Artificial
<220> FEATURE:
<223> OTHER INFORMATION: artificially synthesized sequence
<220> FEATURE:
<221> NAME/KEY: MISC_FEATURE
<222> LOCATION: (1)..(1)
<223> OTHER INFORMATION: "Xaa" indicates Arg or Ala.
<220> FEATURE:
<221> NAME/KEY: MISC_FEATURE
<222> LOCATION: (2)..(2)
<223> OTHER INFORMATION: "Xaa" indicates Gly or Ala.
```

```
<220> FEATURE:
<221> NAME/KEY: MISC_FEATURE
<222> LOCATION: (3)..(3)
<223> OTHER INFORMATION: "Xaa" indicates Phe or Ala.
<220> FEATURE:
<221> NAME/KEY: MISC_FEATURE
<222> LOCATION: (4)..(4)
<223> OTHER INFORMATION: "Xaa" indicates Ser or Ala.

<400> SEQUENCE: 66

Xaa Xaa Xaa Xaa
1

<210> SEQ ID NO 67
<211> LENGTH: 4
<212> TYPE: PRT
<213> ORGANISM: Artificial
<220> FEATURE:
<223> OTHER INFORMATION: artificially synthesized sequence

<400> SEQUENCE: 67

Arg Gly Phe Ser
1

<210> SEQ ID NO 68
<211> LENGTH: 4
<212> TYPE: PRT
<213> ORGANISM: Artificial
<220> FEATURE:
<223> OTHER INFORMATION: artificially synthesized sequence

<400> SEQUENCE: 68

Ala Gly Phe Ser
1

<210> SEQ ID NO 69
<211> LENGTH: 4
<212> TYPE: PRT
<213> ORGANISM: Artificial
<220> FEATURE:
<223> OTHER INFORMATION: artificially synthesized sequence

<400> SEQUENCE: 69

Arg Ala Phe Ser
1

<210> SEQ ID NO 70
<211> LENGTH: 4
<212> TYPE: PRT
<213> ORGANISM: Artificial
<220> FEATURE:
<223> OTHER INFORMATION: artificially synthesized sequence

<400> SEQUENCE: 70

Arg Gly Ala Ser
1

<210> SEQ ID NO 71
<211> LENGTH: 4
<212> TYPE: PRT
<213> ORGANISM: Artificial
<220> FEATURE:
<223> OTHER INFORMATION: artificially synthesized sequence

<400> SEQUENCE: 71

Arg Gly Phe Ala
1
```

```
<210> SEQ ID NO 72
<211> LENGTH: 4
<212> TYPE: PRT
<213> ORGANISM: Artificial
<220> FEATURE:
<223> OTHER INFORMATION: artificially synthesized sequence

<400> SEQUENCE: 72

Arg Gly Ala Ala
1

<210> SEQ ID NO 73
<211> LENGTH: 4
<212> TYPE: PRT
<213> ORGANISM: Artificial
<220> FEATURE:
<223> OTHER INFORMATION: artificially synthesized sequence

<400> SEQUENCE: 73

Arg Ala Phe Ala
1

<210> SEQ ID NO 74
<211> LENGTH: 4
<212> TYPE: PRT
<213> ORGANISM: Artificial
<220> FEATURE:
<223> OTHER INFORMATION: artificially synthesized sequence

<400> SEQUENCE: 74

Arg Ala Ala Ser
1

<210> SEQ ID NO 75
<211> LENGTH: 4
<212> TYPE: PRT
<213> ORGANISM: Artificial
<220> FEATURE:
<223> OTHER INFORMATION: artificially synthesized sequence

<400> SEQUENCE: 75

Arg Ala Ala Ala
1

<210> SEQ ID NO 76
<211> LENGTH: 4
<212> TYPE: PRT
<213> ORGANISM: Artificial
<220> FEATURE:
<223> OTHER INFORMATION: artificially synthesized sequence

<400> SEQUENCE: 76

Ala Gly Phe Ala
1

<210> SEQ ID NO 77
<211> LENGTH: 4
<212> TYPE: PRT
<213> ORGANISM: Artificial
<220> FEATURE:
<223> OTHER INFORMATION: artificially synthesized sequence

<400> SEQUENCE: 77

Ala Gly Ala Ser
1
```

```
<210> SEQ ID NO 78
<211> LENGTH: 4
<212> TYPE: PRT
<213> ORGANISM: Artificial
<220> FEATURE:
<223> OTHER INFORMATION: artificially synthesized sequence

<400> SEQUENCE: 78

Ala Gly Ala Ala
1

<210> SEQ ID NO 79
<211> LENGTH: 4
<212> TYPE: PRT
<213> ORGANISM: Artificial
<220> FEATURE:
<223> OTHER INFORMATION: artificially synthesized sequence

<400> SEQUENCE: 79

Ala Ala Phe Ser
1

<210> SEQ ID NO 80
<211> LENGTH: 4
<212> TYPE: PRT
<213> ORGANISM: Artificial
<220> FEATURE:
<223> OTHER INFORMATION: artificially synthesized sequence

<400> SEQUENCE: 80

Ala Ala Phe Ala
1

<210> SEQ ID NO 81
<211> LENGTH: 4
<212> TYPE: PRT
<213> ORGANISM: Artificial
<220> FEATURE:
<223> OTHER INFORMATION: artificially synthesized sequence

<400> SEQUENCE: 81

Ala Ala Ala Ser
1

<210> SEQ ID NO 82
<211> LENGTH: 4
<212> TYPE: PRT
<213> ORGANISM: Artificial
<220> FEATURE:
<223> OTHER INFORMATION: artificially synthesized sequence

<400> SEQUENCE: 82

Ala Ala Ala Ala
1

<210> SEQ ID NO 83
<211> LENGTH: 4
<212> TYPE: PRT
<213> ORGANISM: Artificial
<220> FEATURE:
<223> OTHER INFORMATION: artificially synthesized sequence
<220> FEATURE:
<221> NAME/KEY: MISC_FEATURE
<222> LOCATION: (1)..(1)
<223> OTHER INFORMATION: "Xaa" indicates Glu or Ala.
<220> FEATURE:
<221> NAME/KEY: MISC_FEATURE
<222> LOCATION: (2)..(2)
<223> OTHER INFORMATION: "Xaa" indicates Ile or Ala.
```

```
<220> FEATURE:
<221> NAME/KEY: MISC_FEATURE
<222> LOCATION: (3)..(3)
<223> OTHER INFORMATION: "Xaa" indicates Asp or Ala.
<220> FEATURE:
<221> NAME/KEY: MISC_FEATURE
<222> LOCATION: (4)..(4)
<223> OTHER INFORMATION: "Xaa" indicates Leu or Ala.

<400> SEQUENCE: 83

Xaa Xaa Xaa Xaa
1

<210> SEQ ID NO 84
<211> LENGTH: 4
<212> TYPE: PRT
<213> ORGANISM: Artificial
<220> FEATURE:
<223> OTHER INFORMATION: artificially synthesized sequence

<400> SEQUENCE: 84

Glu Ile Asp Leu
1

<210> SEQ ID NO 85
<211> LENGTH: 4
<212> TYPE: PRT
<213> ORGANISM: Artificial
<220> FEATURE:
<223> OTHER INFORMATION: artificially synthesized sequence

<400> SEQUENCE: 85

Ala Ile Asp Leu
1

<210> SEQ ID NO 86
<211> LENGTH: 4
<212> TYPE: PRT
<213> ORGANISM: Artificial
<220> FEATURE:
<223> OTHER INFORMATION: artificially synthesized sequence

<400> SEQUENCE: 86

Glu Ala Asp Leu
1

<210> SEQ ID NO 87
<211> LENGTH: 4
<212> TYPE: PRT
<213> ORGANISM: Artificial
<220> FEATURE:
<223> OTHER INFORMATION: artificially synthesized sequence

<400> SEQUENCE: 87

Glu Ile Ala Leu
1

<210> SEQ ID NO 88
<211> LENGTH: 4
<212> TYPE: PRT
<213> ORGANISM: Artificial
<220> FEATURE:
<223> OTHER INFORMATION: artificially synthesized sequence

<400> SEQUENCE: 88

Glu Ile Asp Ala
1
```

```
<210> SEQ ID NO 89
<211> LENGTH: 4
<212> TYPE: PRT
<213> ORGANISM: Artificial
<220> FEATURE:
<223> OTHER INFORMATION: artificially synthesized sequence

<400> SEQUENCE: 89

Glu Ile Ala Ala
1

<210> SEQ ID NO 90
<211> LENGTH: 4
<212> TYPE: PRT
<213> ORGANISM: Artificial
<220> FEATURE:
<223> OTHER INFORMATION: artificially synthesized sequence

<400> SEQUENCE: 90

Glu Ala Asp Ala
1

<210> SEQ ID NO 91
<211> LENGTH: 4
<212> TYPE: PRT
<213> ORGANISM: Artificial
<220> FEATURE:
<223> OTHER INFORMATION: artificially synthesized sequence

<400> SEQUENCE: 91

Glu Ala Ala Leu
1

<210> SEQ ID NO 92
<211> LENGTH: 4
<212> TYPE: PRT
<213> ORGANISM: Artificial
<220> FEATURE:
<223> OTHER INFORMATION: artificially synthesized sequence

<400> SEQUENCE: 92

Glu Ala Ala Ala
1

<210> SEQ ID NO 93
<211> LENGTH: 4
<212> TYPE: PRT
<213> ORGANISM: Artificial
<220> FEATURE:
<223> OTHER INFORMATION: artificially synthesized sequence

<400> SEQUENCE: 93

Ala Ile Asp Ala
1

<210> SEQ ID NO 94
<211> LENGTH: 4
<212> TYPE: PRT
<213> ORGANISM: Artificial
<220> FEATURE:
<223> OTHER INFORMATION: artificially synthesized sequence

<400> SEQUENCE: 94

Ala Ile Ala Leu
1
```

```
<210> SEQ ID NO 95
<211> LENGTH: 4
<212> TYPE: PRT
<213> ORGANISM: Artificial
<220> FEATURE:
<223> OTHER INFORMATION: artificially synthesized sequence

<400> SEQUENCE: 95

Ala Ile Ala Ala
1

<210> SEQ ID NO 96
<211> LENGTH: 4
<212> TYPE: PRT
<213> ORGANISM: Artificial
<220> FEATURE:
<223> OTHER INFORMATION: artificially synthesized sequence

<400> SEQUENCE: 96

Ala Ala Asp Leu
1

<210> SEQ ID NO 97
<211> LENGTH: 4
<212> TYPE: PRT
<213> ORGANISM: Artificial
<220> FEATURE:
<223> OTHER INFORMATION: artificially synthesized sequence

<400> SEQUENCE: 97

Ala Ala Asp Ala
1

<210> SEQ ID NO 98
<211> LENGTH: 4
<212> TYPE: PRT
<213> ORGANISM: Artificial
<220> FEATURE:
<223> OTHER INFORMATION: artificially synthesized sequence

<400> SEQUENCE: 98

Ala Ala Ala Leu
1

<210> SEQ ID NO 99
<211> LENGTH: 4
<212> TYPE: PRT
<213> ORGANISM: Artificial
<220> FEATURE:
<223> OTHER INFORMATION: artificially synthesized sequence

<400> SEQUENCE: 99

Ala Ala Ala Ala
1

<210> SEQ ID NO 100
<211> LENGTH: 10
<212> TYPE: PRT
<213> ORGANISM: Artificial
<220> FEATURE:
<223> OTHER INFORMATION: artificially synthesized sequence
<220> FEATURE:
<221> NAME/KEY: MISC_FEATURE
<222> LOCATION: (2)..(2)
<223> OTHER INFORMATION: "Xaa" indicates 3-5 arbitrary amino acids
<220> FEATURE:
<221> NAME/KEY: MISC_FEATURE
<222> LOCATION: (3)..(3)
<223> OTHER INFORMATION: "Xaa" indicates Cys or a basic amino acid
```

```
<220> FEATURE:
<221> NAME/KEY: MISC_FEATURE
<222> LOCATION: (4)..(4)
<223> OTHER INFORMATION: "Xaa" indicates Leu or Arg
<220> FEATURE:
<221> NAME/KEY: MISC_FEATURE
<222> LOCATION: (5)..(5)
<223> OTHER INFORMATION: "Xaa" indicates 1-3 arbitrary amino acids
<220> FEATURE:
<221> NAME/KEY: MISC_FEATURE
<222> LOCATION: (8)..(8)
<223> OTHER INFORMATION: "Xaa" indicates Gly or Ser
<220> FEATURE:
<221> NAME/KEY: MISC_FEATURE
<222> LOCATION: (9)..(9)
<223> OTHER INFORMATION: "Xaa" indicates 3-5 arbitrary amino acids

<400> SEQUENCE: 100

Pro Xaa Xaa Xaa Xaa Leu Thr Xaa Xaa Pro
1               5                   10

<210> SEQ ID NO 101
<211> LENGTH: 17
<212> TYPE: PRT
<213> ORGANISM: Artificial
<220> FEATURE:
<223> OTHER INFORMATION: artificially synthesized sequence
<220> FEATURE:
<221> NAME/KEY: MISC_FEATURE
<222> LOCATION: (2)..(2)
<223> OTHER INFORMATION: "Xaa" indicates an arbitrary amino acid
<220> FEATURE:
<221> NAME/KEY: MISC_FEATURE
<222> LOCATION: (3)..(3)
<223> OTHER INFORMATION: "Xaa" indicates an arbitrary amino acid
<220> FEATURE:
<221> NAME/KEY: MISC_FEATURE
<222> LOCATION: (4)..(4)
<223> OTHER INFORMATION: "Xaa" indicates an arbitrary amino acid
<220> FEATURE:
<221> NAME/KEY: MISC_FEATURE
<222> LOCATION: (5)..(5)
<223> OTHER INFORMATION: "Xaa" indicates an arbitrary amino acid
<220> FEATURE:
<221> NAME/KEY: MISC_FEATURE
<222> LOCATION: (6)..(6)
<223> OTHER INFORMATION: "Xaa" indicates Cys or a basic amino acid
<220> FEATURE:
<221> NAME/KEY: MISC_FEATURE
<222> LOCATION: (7)..(7)
<223> OTHER INFORMATION: "Xaa" indicates Leu or Arg
<220> FEATURE:
<221> NAME/KEY: MISC_FEATURE
<222> LOCATION: (8)..(8)
<223> OTHER INFORMATION: "Xaa" indicates an arbitrary amino acid
<220> FEATURE:
<221> NAME/KEY: MISC_FEATURE
<222> LOCATION: (9)..(9)
<223> OTHER INFORMATION: "Xaa" indicates an arbitrary amino acid
<220> FEATURE:
<221> NAME/KEY: MISC_FEATURE
<222> LOCATION: (12)..(12)
<223> OTHER INFORMATION: "Xaa" indicates Gly or Ser
<220> FEATURE:
<221> NAME/KEY: MISC_FEATURE
<222> LOCATION: (13)..(13)
<223> OTHER INFORMATION: "Xaa" indicates an arbitrary amino acid
<220> FEATURE:
<221> NAME/KEY: MISC_FEATURE
<222> LOCATION: (14)..(14)
<223> OTHER INFORMATION: "Xaa" indicates an arbitrary amino acid
<220> FEATURE:
<221> NAME/KEY: MISC_FEATURE
<222> LOCATION: (15)..(15)
<223> OTHER INFORMATION: "Xaa" indicates an arbitrary amino acid
<220> FEATURE:
<221> NAME/KEY: MISC_FEATURE
```

```
<222> LOCATION: (16)..(16)
<223> OTHER INFORMATION: "Xaa" indicates an arbitrary amino acid

<400> SEQUENCE: 101

Pro Xaa Xaa Xaa Xaa Xaa Xaa Xaa Xaa Leu Thr Xaa Xaa Xaa Xaa Xaa Pro
1               5                   10                  15

<210> SEQ ID NO 102
<211> LENGTH: 17
<212> TYPE: PRT
<213> ORGANISM: Artificial
<220> FEATURE:
<223> OTHER INFORMATION: artificially synthesized sequence
<220> FEATURE:
<221> NAME/KEY: MISC_FEATURE
<222> LOCATION: (2)..(2)
<223> OTHER INFORMATION: "Xaa" indicates Arg, Ala, or a conservative
      substitution thereof
<220> FEATURE:
<221> NAME/KEY: MISC_FEATURE
<222> LOCATION: (3)..(3)
<223> OTHER INFORMATION: "Xaa" indicates Gly, Ala, or a conservative
      substitution thereof
<220> FEATURE:
<221> NAME/KEY: MISC_FEATURE
<222> LOCATION: (4)..(4)
<223> OTHER INFORMATION: "Xaa" indicates Phe, Ala, or a conservative
      sunstitution thereof
<220> FEATURE:
<221> NAME/KEY: MISC_FEATURE
<222> LOCATION: (5)..(5)
<223> OTHER INFORMATION: "Xaa" indicates Ser, Ala, or a conservative
      substitution thereof
<220> FEATURE:
<221> NAME/KEY: MISC_FEATURE
<222> LOCATION: (6)..(6)
<223> OTHER INFORMATION: "Xaa" indicates Cys or a basic amino acid
<220> FEATURE:
<221> NAME/KEY: MISC_FEATURE
<222> LOCATION: (7)..(7)
<223> OTHER INFORMATION: "Xaa" indicates Leu or Arg
<220> FEATURE:
<221> NAME/KEY: MISC_FEATURE
<222> LOCATION: (8)..(8)
<223> OTHER INFORMATION: "Xaa" indicates Leu, Ala, or a conservative
      substitution thereof
<220> FEATURE:
<221> NAME/KEY: MISC_FEATURE
<222> LOCATION: (9)..(9)
<223> OTHER INFORMATION: "Xaa" indicates Leu, Ala, or a conservative
      substitution thereof
<220> FEATURE:
<221> NAME/KEY: MISC_FEATURE
<222> LOCATION: (12)..(12)
<223> OTHER INFORMATION: "Xaa" indicates Gly or Ser
<220> FEATURE:
<221> NAME/KEY: MISC_FEATURE
<222> LOCATION: (13)..(13)
<223> OTHER INFORMATION: "Xaa" indicates Glu, Ala, or a conservative
      substitution thereof
<220> FEATURE:
<221> NAME/KEY: MISC_FEATURE
<222> LOCATION: (14)..(14)
<223> OTHER INFORMATION: "Xaa" indicates Ile, Ala, or a conservative
      substitution thereof
<220> FEATURE:
<221> NAME/KEY: MISC_FEATURE
<222> LOCATION: (15)..(15)
<223> OTHER INFORMATION: "Xaa" indicates Asp, Ala, or a conservative
      substitution thereof
<220> FEATURE:
<221> NAME/KEY: MISC_FEATURE
<222> LOCATION: (16)..(16)
<223> OTHER INFORMATION: "Xaa" indicates Leu, Ala, or a conservative
      substitution thereof

<400> SEQUENCE: 102
```

```
Pro Xaa Xaa Xaa Xaa Xaa Xaa Xaa Xaa Leu Thr Xaa Xaa Xaa Xaa Xaa Pro
1               5                   10                  15
```

HUMANIN, A POLYPEPTIDE SUPPRESSING NEURONAL DEATH

TECHNICAL FIELD

The present invention relates to polypeptides protecting neurons from cell death associated with Alzheimer's disease.

BACKGROUND ART

Alzheimer's disease (AD) is currently the most actively studied neurodegenerative disease. AD is clinically characterized by progressive amnesia and cognitive impairment, and pathlogically characterized by a wide range of neuronal loss, intraneuronal tangles, and extracellular senile plaques that have congophilic dense core. Effective treatment for AD still does not exist. It is generally accepted that not all, but many of the clinical manifestations of this disease are explained by progressive neuronal death. Elucidation of pathological mechanism of the onset of neuronal death in AD, to prevent AD is essential for developing novel effective treatments for AD.

Four different groups of mutant genes are known to cause early-onset familial AD (FAD): V642I/F/G APP (the number represents the position in $APP_{695}$, an APP consisting of 695 amino acids); K595N/M696L (NL-APP); presenilin (PS)-1 mutants; and PS-2 mutants (Shastry, B. S. and Giblin, F. J. (1999) Brain Res. Bull. 48, 121-127). Yamatsuji et al. suggested that these FAD genes might cause cell death of neurons, based on the observation on nerve cell line F11 wherein three V642 type mutant cDNA of APP was transiently expressed (Yamatsuji, T. et al. (1996) Science 272, 1349-1352). The result was also confirmed by experiments that used primary cultured neurons and other nerve cell lines (Zhao, B. et al. (1997) J. Neurosci. Res. 47, 253-263; Luo, J. J. et al. (1999) J. Neurosci. Res. 55, 629-42). Further, Wolozin et al. revealed that FAD-linked mutant N141I PS-2 significantly enhances cell mortality in PC12 cells, and that FAD-linked mutant PS-1 induces apoptosis of T lymphocytes (Wolozin, B. et al. (1996) Science 274, 1710-1713; Wolozin, B. et al. (1998) Neurobiol. Aging 19, S23-27). Furthermore, regarding PS-1, enhanced sensitivity to neuronal death induced by Aβ addition and/or trophic factor deficiency due to the expression of PS-1 mutant (Guo, Q. et al. (1996) Neuroreport 8, 379-83; Zhang, Z. et al. (1998) Nature 395, 698-702; Guo, Q. et al. (1999) Proc. Natl. Acad. Sci. U.S.A. 96., 4125-30); and enhanced sensitivity to neuronal death by trophic factor deficiency in cultured cortical neurons, derived from transgenic rats overexpressing wild-type PS-1, compared with those in non-transgenic controls (Czech, C. et al. (1998) Neuroscience 87, 325-36); and such have been repeatedly observed. Although it is controversial whether the mutant PS-1 is a stimulation factor of neuronal death or has no effect on neuronal death (Weihl, C. C. et al. (1999) J. Neurosci. 19, 5360-9; Bursztajn, S. et al. (1998) J. Neurosci. 18, 9790-9), it is highly possible that all of the four types of known FAD genes (V642-type mutant APP, NL-APP, PS-1 mutant, and PS-2 mutant) induce neuronal death or amplify the vulnerability of neurons to other cell death stimuli under certain conditions. Therefore, finding molecules that suppress AD gene-induced cell death observed in neurons in suggested to be the most important key for developing methods to treat AD.

DISCLOSURE OF THE INVENTION

An object of the present invention is to provide polypeptides that protect neurons from cell death associated with Alzheimer's disease, and use of the same.

The present inventor has previously established a nerve cell line (F11/EcR/V642I), which inductively expresses familial Alzheimer's disease-type mutant V642I amyloid precursor proteins (V642I APP) (see International Publication No. WO 00/14204). According to the system, V642I APP is expressed in F11 neurons in response to ecdysone treatment. Cell death occurred in almost all of the F11/EcR/V642I cells incubated with ecdysone for 2 to 3 days; whereas cell death occurred in only a few cells in the control incubation. The present inventor used the F11/EcR/V642I cells to search for genes that act as antagonists of V642I APP-induced neuronal death.

More specifically, a cDNA library was constructed from the brain of Alzheimer's disease (AD) patient, and was transfected into the F11/EcR/V642I cells mentioned above. Then a death trap screening operation was repeatedly performed to select cells that survived neuronal death induced by V642I APP. As a result, the present inventor succeeded in identifying a novel gene that protect cells against neuronal death induced by V642I APP. It was revealed that the clone, dubbed Humanin (HN) cDNA, encoding a novel polypeptide of 24-amino acids, suppresses neuronal death associated with AD. That is, the clone suppressed neuronal death induced by all of the known types of early-onset familial AD genes [V642I APP, K595N/M596L APP, M146L presenilin (PS)-1, and N141I PS-2] and by Aβ1-43. In contrast, the clone had no effect on neurotoxicity of polyglutamine repeat Q79, associated with Huntington's disease (HD)/spinocerebellar ataxia (SCA); and mutants of Cu/Zn-dependent superoxide dismutase (SOD1), associated with amyotrophic lateral sclerosis (ALS). HN mRNA was mainly produced in several organs other than the central nervous system. Transfection of HN cDNA into neurons led to transcription and production of expected peptides, which peptides were secreted into the culture medium up to a level of about 10 µM. The culture supernatant was enough active to demonstrate significant protection of cells from neuronal death induced by V642I APP. Synthetic HN polypeptide also showed neuroprotective action with similar dose-response properties against the four types of AD genes, and its suppression was maximal at 1 to 10 µM. Polypeptides expressed within neurons from a cDNA encoding an HN derivative, lacking secretion ability, failed to protect neurons from cell death. However, the same polypeptide synthesized and added to the culture medium showed protective action, which results indicate that the HN polypeptide acts from outside of the cell. Cys at position 8 and Ser at position 14 were found to be important according to an experiment detecting the activity of polypeptides with modified structure. C8A substitution completely deprived the polypeptide of the cell death rescue activity. On the other hand, S14G substitution remarkably enhanced the rescue activity of the polypeptide. S14G HN polypeptides (HNG) showed complete protective action against all of the four types of FAD genes at low nanomolar concentrations (1 to 10 nM). Anti-AD activity of HN was also observed in primary cultured cortical neurons. Specifically, µM levels of HN and nM levels of S14G derivatives (HNG) protected cells form cell death and cell damage caused by Aβ, whereas C8A (HNA) lacked such activity. Furthermore, upon analysis of detailed structure-function relationship, amino acids from Pro at position 3 to Pro at position 19 were identified to be important for neuroprotective function, and among them, seven residues were identified as essential residues for the activity. In addition, C8 amino acid of S14G HN polypeptide (HNG) could be substituted with basic amino acids, such as His, Arg, or Lys, while maintaining its anti-AD activity. Furthermore, the present inventor succeeded to further enhance the neuroprotective action by introducing two amino acid mutations to the S14G HN polypeptide. Based on these findings, it is possible to develop polypeptides that have higher activity and which are suited for biological administration. These polypeptides open a new path to develop therapeutic drugs for AD, and at the same time, are expected to contribute greatly to the development of AD therapy aiming at protection of neurons from cell death.

The present invention relates to novel polypeptides that protect cells from neuronal death associated with AD, and use of the same. More specifically, the present invention relates to:

(1) a polypeptide that suppresses neuronal death associated with Alzheimer's disease having an amino acid sequence of Formula (I):

Pro-$Xn_1$-(Cys/bXaa)-(Leu/Arg)-$Xn_2$-Leu-Thr-(Gly/Ser)-$Xn_3$-Pro (I) wherein "Cys/bXaa" indicates Cys or a basic amino acid; "(Leu/Arg)" indicates Leu or Arg; "(Gly/Ser)" indicates Gly or Ser; and $Xn_1$, $Xn_2$, and $Xn_3$ independently indicate arbitrary amino acid sequences not more than 10 residues in length, respectively;

(2) a polypeptide according to (a) or (b) shown below:
   (a) a polypeptide having an amino acid sequence selected from the group of SEQ ID NOs: 5 to 8, 10, 12, 13, 21 to 24, 26 to 29, 32, 33, 37 to 40, 46, 48, 54, and 60;
   (b) a polypeptide that suppresses neuronal death associated with Alzheimer's disease having an amino acid sequence selected from the group consisting of SEQ ID NOs: 5 to 8, 10, 12, 13, 21 to 24, 26 to 29, 32, 33, 37 to 40, 46, 48, 54, and 60, wherein one or more amino acids have been substituted, deleted, inserted, and/or added;

(3) the polypeptide of (2), which is used to suppress neuronal death;

(4) a fusion polypeptide comprising the polypeptide of any of (1) to (2) fused with other polypeptides;

(5) a DNA encoding the polypeptide of any one of (1) to (4);

(6) a vector into which the DNA of (5) is inserted;

(7) a host cell retaining the vector of (6);

(8) a method for producing the polypeptide of any one of (1) to (4), comprising the steps of culturing the host cell of (7), and recovering the expressed polypeptide from the host cell or culture supernatant thereof;

(9) a method for suppressing neuronal death comprising the step of contacting a neuron with the polypeptide of any one of (1) to (4);

(10) a method for detecting a cell death suppressing activity of the polypeptide of any one of (1) to (4), comprising the steps of:
   (a) inducing cell death in the presence of the polypeptide of any one of (1) to (4); and
   (b) detecting level of cell death;

(11) a method for detecting the effect of a chemical compound on neuronal death suppressing activity of a polypeptide of any one of (1) to (4), comprising the steps of:
   (a) inducing neuronal death in the presence of a test compound and the polypeptide of any one of (1) to (4); and
   (b) detecting the level of neuronal death;

(12) a method of screening for a chemical compound that regulates the neuronal death suppressing activity of the polypeptide of any one of (1) to (4), comprising the steps of:
   (a) inducing neuronal death in the presence of a test sample and the polypeptide of any one of (1) to (4);
   (b) detecting the level of neuronal death; and
   (c) selecting the compound that enhances or suppresses neuronal death;

(13) a pharmaceutical composition comprising as the effective component the polypeptide of any one of (1) to (4);

(14) the pharmaceutical composition of (13), wherein said composition is a neuronal death suppressant;

(15) the pharmaceutical composition of (13), which is used to prevent or treat diseases that are accompanied by neurodegeneration;

(16) the pharmaceutical composition of (13), which is used to prevent or treat Alzheimer's disease;

(17) an antibody that binds to the polypeptide of any one of (1) to (3);

(18) a DNA for detecting or manipulating DNA encoding the polypeptide of any one of (1) to (4), wherein the DNA comprises at least 15 nucleotides that are complementary to a DNA consisting of the nucleotide sequence of SEQ ID NO: 4 or to a complementary strand thereof; and

(19) a method of screening for a chemical compound that binds to the polypeptide of any one of (1) to (4), comprising the steps of:
   (a) contacting a test sample with the polypeptide of any one of (1) to (4);
   (b) detecting the binding activity between the test sample and the polypeptide; and
   (c) selecting the compound that has the activity to bind to the polypeptide.

The term "polypeptide" herein refers to a peptide or protein consisting of two or more amino acids or amino acid derivatives bound to each other. Peptide isosteres are included as polypeptides of the present invention. The term "polypeptide" normally includes short stranded polypeptides, such as peptides, oligopeptides, and oligomers. It also includes long stranded polypeptides such as proteins. The polypeptide may be naturally modified by post-translational modification and such. They may be also modified by artificial modifications. Modification includes modification of the peptide backbone, amino acid side chain, amino terminus, or carboxyl terminus. The polypeptide may be branched or cyclic. Modification includes acetylation; acylation; ADP ribosylation; amidation; covalent bonding with flavin, nucleotide, nucleotide derivative, lipid, lipid derivative, or phosphatidyl inositol, and such; cross link formulation; cyclization; disulfide bond formation; demethylation; pyroglutamylation; γ-carboxylation; glycosylation; hydroxylation; iodization; methylation; myristoylation; oxidation; phosphorylation; ubiquitination; and so on, but the present invention is not limited to these examples.

The present invention provides polypeptides which protect neurons from cell death associated with Alzheimer's disease. The amino acid sequence of Humanin (HN) polypeptide, isolated by the present inventor, is indicated in SEQ ID NO: 5, and the cDNA sequence of the open reading frame encoding the polypeptide is indicated in SEQ ID NO: 4. Humanin antagonizes neuronal death associated with AD, and shows a saturation activity at a concentration of about 10 μM. In addition, HNG (S14G) (SEQ ID NO: 8), which is a Humanin with an amino acid substitution, showed 100 to 1000 fold higher antagonizing effect compared to Humanin. Further, Cys at position 8 of HNG can be substituted with basic amino acids, such as His, Arg, and Lys, withoutd changes in the activity by the modification of the SH group of the polypeptide. Furthermore, AGA-HNG (SEQ ID NO: 60) which is a derivative of HNG demonstrated an activity several folds higher than that of HNG. The polypeptides of the present invention include Humanin, HNG, AGA-HNG, and substituted forms thereof wherein the Cys residue (referred to as C8) is substituted with a basic amino acid.

Further, the present invention demonstrated that addition of a FLAG tag (DYKDDDDK) (SEQ ID NO: 61) to the C-terminus of Humanin does not affect the neuroprotective action thereof (Example 3). Furthermore, even when the four C-terminal amino acids (KRRA) (SEQ ID NO: 62) of Humanin were substituted with other amino acids, a neuroprotective action equivalent to that of the original Humanin was present in the substituted polypeptide (Example 6). These facts demonstrate that polypeptides with equivalent or higher neuroprotective action to can be prepared by introducing mutations to the amino acid sequence of Humanin, HNG, AGA-HNG, and substituted forms thereof, wherein the C8 is substituted with a basic amino acid.

The present inventor performed further detailed analysis using deletion mutants of Humanin, and found that even a polypeptide, consisting of 17 amino acids from position 3 to 19 of Humanin (HN-17, SEQ ID NO: 21), is sufficient to protect neurons (Example 13). Furthermore, half or more of the amino acid residues of HNG can be substituted while retaining the activity according to the verification of the neuronal death suppression activity of polypeptides consisting of the 3rd Pro to the 19th Pro of HNG (HNG-17, SEQ ID NO: 24), wherein each amino acid residue of the polypeptide was substituted with another amino acid. This experiment elucidated that 7 amino acids in HNG-17 are essential for neuronal death suppression: Pro at position 1; Cys at position 6; Leu at position 7; Leu-Thr-Gly at positions 10 to 12; and Pro at position 17. Therefore, polypeptides having different amino acid sequences can be prepared by modification, such as substitution, deletion, and/or insertion, of residues other than those described above and retaining the residues above.

What is much more important, is that even the 7 amino acids, mentioned above as essential amino acids for the activity, may be also substituted with other amino acids. For example, the polypeptides retains the neuroprotective activity even when the Gly at position 12 of NHG-17 is Ser (that is NH-17. In addition, a synthetic polypeptide (HNR; SEQ ID NO: 7) wherein the position corresponding to the Leu at position 7 is substituted with Arg, demonstrated a neuroprotective activity similar to that of the synthetic HN (Example 12). Furthermore, as mentioned above, an HNG with basic amino acid, such as His, Arg, or Lys, for the Cys corresponding to position 6 of the HNG-17 shows neuroprotective activity. Particularly, the HNG mutant wherein the Cys is substituted with Arg or Lys demonstrated a neuroprotective activity equivalent to that of the original HNG (Example 14). According to these facts, preparation of polypeptides with equivalent or higher neuronal death suppression activity to the polypeptides, which activities were detected in the Examples of the present invention, are expected by mutating amino acids that are non-essential and/or essential for the activity of these polypeptides.

The polypeptide of the present invention includes polypeptides that suppress neuronal death associated with Alzheimer's disease (AD) and having an amino acid sequence consisting of Formula (I):

Pro-$Xn_1$-(Cys/bXaa)-(Leu/Arg)-$Xn_2$-Leu-Thr-(Gly/Ser)-$Xn_3$-Pro (1) (SEQ ID NO: 63).

Herein, "Cys/bXaa" indicates Cys or a basic amino acid; "(Leu/Arg)" indicates Leu or Arg; "(Gly/Ser)" indicates Gly or Ser; and $Xn_1$, $Xn_2$, and $Xn_3$ independently indicate arbitrary amino acids not more than 10 residues, respectively. A polypeptide that has the amino acid sequence as above may be also expressed as:

Pro-$(Xaa)_{1-10}$-(Cys/bXaa)-(Leu/Arg)-$(Xaa)_{1-10}$-Leu-Thr-(Gly/Ser)-$(Xaa)_{1-10}$Pro (SEQ ID NO: 64)    (II)

(wherein Xaa indicates an arbitrary amino acid; "$(Xaa)_{m-n}$" indicates m to n residues of arbitrary amino acids; "bXaa" indicates a basic amino acid; "Cys/bXaa" indicates Cys or a basic amino acid; "(Leu/Arg)" indicates Leu or Arg; and "(Gly/Ser)" indicates Gly or Ser).

Basic amino acids refer to amino acids in which its R group (side chain) is positively charged at pH7.0. Examples of natural basic amino acids include Arg, Lys, and His. The amino acid sequences of a polypeptide of this invention that has Arg, Lys, or His as the basic amino acids can be represented, for example, as:

Pro-$Xn_1$-(Cys/Arg/Lys/His)-(Leu/Arg)-$Xn_2$-Leu-Thr-(Gly/Ser)-$Xn_3$-Pro (SEQ ID NO: 65)    (III)

(wherein "(Cys/Arg/Lys/His)" indicates Cys, Arg, Lys, or His; "(Leu/Arg)" indicates Leu or Arg; "(Gly/Ser)" indicates Gly or Ser; and $Xn_1$, $Xn_2$, and $X_{n3}$ independently indicate arbitrary amino acids not more than 10 residues, respectively). Herein, Arg and Lys are particularly preferable as the basic amino acid at this position.

Preferably, $Xn_1$, $Xn_2$, and $Xn_3$ are independently arbitrary amino acids of 2 to 6, 0 to 4, and 2 to 6 residues, respectively (that is, $Xn_1=(Xaa)_{2-6}$, $Xn_2=(Xaa)_{0-4}$, and $Xn_3=(Xaa)_{2-6}$); more preferably 3 to 5, 1 to 3, and 3 to 5 residues, respectively (that is, $Xn_1=(Xaa)_{3-5}$, $Xn_2=(Xaa)_{1-3}$, and $Xn_3=(Xaa)_{3-5}$); and most preferably 4, 2, and 4 residues, respectively (that is, $Xn_1=(Xaa)_4$, $Xn_2=(Xaa)_2$, and $Xn_3=(Xaa)_4$). Added amino acids of about 6 residues sometimes forms an α-helix and behaves like a single amino acid residue. A polypeptide of the present invention may be a polypeptide wherein arbitrary amino acids with no more than 6 residues are added to all or any one of $Xn_1$, $Xn_2$, and $Xn_3$ consisting of arbitrary amino acids of 4 residues, 2 residues, and 4 residues, respectively.

Such polypeptide may be prepared according to known peptide synthesis techniques, and also by the expression of a DNA that encodes such polypeptides.

Preferably, the sequence of $Xn_1$ includes, for example, sequences consisting of (Arg/Ala)-(Gly/Ala)-(Phe/Ala)-(Ser/Ala) (SEQ ID NO: 66), and sequences with conservative substitution thereof. Herein, for example, "Arg/Ala" indicates Arg or Ala ("/" indicates that it is either one of the residues; the same is indicated throughout the description herein). Examples of such sequences include Arg-Gly-Phe-Ser (SEQ ID NO: 67), Ala-Gly-Phe-Ser (SEQ ID NO: 68), Arg-Ala-Phe-Ser (SEQ ID NO: 69), Arg-Gly-Ala-Ser (SEQ ID NO: 70), Arg-Gly-Phe-Ala (SEQ ID NO: 71), and so on. Other examples include Arg-Gly-Ala-Ala (SEQ ID NO: 72), Arg-Ala-Phe-Ala (SEQ ID NO: 73), Arg-Ala-Ala-Ser (SEQ ID NO: 74), Arg-Ala-Ala-Ala (SEQ ID NO: 75), Ala-Gly-Phe-Ala (SEQ ID NO: 76), Ala-Gly-Ala-Ser (SEQ ID NO: 77), Ala-Gly-Ala-Ala (SEQ ID NO: 78), Ala-Ala-Phe-Ser (SEQ ID NO: 79), Ala-Ala-Phe-Ala (SEQ ID NO: 80), Ala-Ala-Ala-Ser (SEQ ID NO: 81), Ala-Ala-Ala-Ala (SEQ ID NO: 82), and such. Conservative substitution can be exemplified by substitution within a group of amino acids, corresponding to conservative substitution, which will be described later. On the other hand, the sequence of $Xn_2$ preferably includes, for example, sequences consisting of (Leu/Ala)-(Leu/Ala), and sequences with conservative substitution thereof. Such sequences include Leu-Leu, Ala-Leu, Leu-Ala, and such. Ala-Ala can be also exemplified as such sequences. Furthermore, the sequence of $Xn_3$ preferably includes, for example, sequences consisting of (Glu/Ala)-(Ile/Ala)-(Asp/Ala)-(Leu/Ala) (SEQ ID NO: 83), and sequences with conservative substitution thereof. Such examples include Glu-Ile-Asp-Leu (SEQ ID NO: 84), Ala-Ile-Asp-Leu (SEQ ID NO: 85), Glu-Ala-Asp-Leu (SEQ ID NO: 86), Glu-Ile-Ala-Leu (SEQ ID NO: 87), Glu-Ile-Asp-Ala (SEQ ID NO: 88), and so on. Other examples are Glu-Ile-Ala-Ala (SEQ ID NO: 89), Glu-Ala-Asp-Ala (SEQ ID NO: 90), Glu-Ala-Ala-Leu (SEQ ID NO: 91), Glu-Ala-Ala-Ala (SEQ ID NO: 92), Ala-Ile-Asp-Ala (SEQ ID NO: 93), Ala-Ile-Ala-Leu (SEQ ID NO: 94), Ala-Ile-Ala-Ala (SEQ ID NO: 95), Ala-Ala-Asp-Leu (SEQ ID NO: 96), Ala-Ala-Asp-Ala (SEQ ID NO: 97), Ala-Ala-Ala-Leu (SEQ ID NO: 98), Ala-Ala-Ala-Ala (SEQ ID NO: 99), and so on. The sequences of $Xn_1$, $Xn_2$, and $Xn_3$ may be selected from arbitrary combinations.

Neuronal death associated with AD is induced by the expression of APP, PS-1, or PS-2 mutants (for example, V642I/F/G APP, NL-APP, M146L PS-1, and N141I PS-2) in established neuronal cell lines (for example, F11 cells) and primary neuronal cultures (for example, rat brain cortical primary culture); and also by the addition of Aβ (for example, Aβ1-43) to primary neuronal cultures. The term "suppression of neuronal death associated with Alzheimer's disease" herein defines to suppress at least one of the neuronal deaths associated with AD including those mentioned above. Specifically, the polypeptides of the present invention include those, that suppress at least any one of these neuronal deaths associated with AD. The suppression of cell death doesn't have to be a complete suppression so long as the suppression is significant. The activity of proteins to suppress neuronal death can be detected according to the method described in the Examples, or by other published methods (see for example, International Publication No. WO 00/14204).

More specifically, a method as follows can be exemplified: (1) transfect neurons (for example, F11 cells) with vectors expressing FAD genes, such as V642I/F/G APP, NL-APP, M146L PS-1, and N141I PS-2, alone or in combination with a vector expressing a polypeptide to be examined; (2) cultivating the cells for a defined period (for example, 72 hours); and (3) detecting level of cell death by trypan blue exclusion assay. Alternatively, a polypeptide to be examined is prepared in advance, and cell death may be measured upon transfection of FAD genes into cells in the presence or absence of the polypeptide. FAD genes may be also conditionally expressed using an inductive promoter. A polypeptide is determined to suppress neuronal death associated with AD, when the cell death under the existence of the protein is significantly decreased in comparison to those induced in the absence of the polypeptide to be examined. Additionally, other cells such as primary cultured neurons may be used, and induction of cell death can be also carried out by the addition of Aβ. Cell death can be measured by detecting morphological changes, LDH release, or apoptosis (morphological changes of the nucleus, fragmentation of DNA, and such) in addition to trypan blue exclusion.

Further, the polypeptides of the present invention include polypeptides having an amino acid sequence selected from the group of SEQ ID NOs: 5 to 8, 10, 12, 13, 21 to 24, 26 to 29, 32, 33, 37 to 40, 46, 48, 54, and 60; and polypeptides that suppress neuronal death associated with Alzheimer's disease (AD), wherein one or more amino acids of the polypeptide selected from the group of SEQ ID NOs: 5 to 8, 10, 12, 13, 21 to 24, 26, to 29, 32, 33, 37 to 40, 46, 48, 54, and 60 have been substituted, deleted, inserted, and/or added.

Although there are no particular limitations on the number of amino acid residues to be mutated, it is considered that the number of the residues to be mutated by substitution, deletion, and/or insertion in a amino acid sequence, is generally 15 residues or less, preferably 12 residues or less, more preferably 10 residues or less, and even more preferably 8 residues or less (for example, 5 residues or less). There is no limitation on the number of the amino acids to be added, so long as the activity to suppress neuronal death associated with AD is maintained. Artificially produced amino acid sequences and naturally occurring polypeptide sequences are included in the amino acid sequence wherein the amino acids have been substituted, deleted, inserted, and/or added.

The original activity of a polypeptide is expected to be retained by artificial substitution of amino acids between amino acids with similar characteristics. The polypeptides of the present invention include polypeptides that suppress neuronal death associated with AD, having an amino acid sequence selected from the group of SEQ ID NOs: 5 to 8, 10, 12, 13, 21 to 24, 26 to 29, 32, 33, 37 to 40, 46, 48, 54, and 60 with conservative substitution to the amino acids of the polypeptides. Conservative substitutions are considered to be important for substituting amino acids essential for suppressing neuronal death (for example, the 7 amino acids essential for HNG-17, mentioned above). Such conservative substitution of amino acids is well known to those skilled in the art. Group of amino acids between which conservative substitution can be exemplified by: (1) basic amino acids (for example, lysine, arginine, and histidine); (2) acidic amino acids (for example, aspartic acid, and glutamic acid); (3) uncharged polar amino acids (for example, glycine, asparagine, glutamine, serine, threonine, tyrosine, and cysteine); (4) non-polar amino acids (for example, alanine, valine, leucine, isoleucine, proline, phenylalanine, methionine, and tryptophan); (5) β branched amino acids (for example, threonine, valine, and isoleucine); (6) aromatic amino acids (for example, tyrosine, phenylalanine, tryptophan, and histidine), and such. Alternatively, the activity to suppress neuronal death, stability, tissue localization, and such of the polypeptide can be enhanced or decreased by non-conservative substitution.

The polypeptide of this invention may be produced as a synthetic polypeptide by known peptide synthesis techniques (Japanese Biochemical Society edition, "Shin Seikagaku Jikken Koza Tanpakushitu (New Course on Biochemistry Experiments, Proteins) VI," pp. 3-74, Tokyo Kagakudojin, 1992). The method for peptide synthesis may be either solid-phase synthesis or liquid-phase synthesis. Further, polypeptides with arbitrary amino acid mutations can be prepared through the introduction of mutation to Humanin cDNA (for example, SEQ ID NO: 4) by the production of synthetic DNA or by site directed mutagenesis; and then, expressing the mutated cDNA in a host cell. There are no limitations on the number and position of the amino acids to be modified so long as the obtained polypeptide suppresses neuronal death associated with AD.

Although there is no limitation regarding the number of amino acid residues in the polypeptides of this invention, however, for example, when the polypeptide is used as a pharmaceutical composition, polypeptides of smaller molecular size are generally preferred. Absence of portions (for example, amino acid residues or functional groups) unnecessary for the activity decreases antigenicity, and non-specific interactions with other molecules can be avoided which as a result is expected to reduce unfavorable side effects. The polypeptides of the present invention consist of preferably 500 amino acid residues or less, more preferably 100 residues or less, much more preferably 50 residues or less, and even more preferably 30 residues or less. The average molecular weight of the polypeptides is preferably 60 kDa or less, more preferably 15 kDa or less, more preferably 6 kDa or less, and even more preferably 4 kDa or less.

Furthermore, the present invention relates to fusion polypeptides of the above-mentioned polypeptides of the present invention with other polypeptides. A fusion polypeptide is a polypeptide in which at least two polypeptides that are not bound in nature are joined, and can be produced by peptide synthesis, or by expressing nucleic acids wherein the polypeptide encoding regions are ligated in frame. Examples of other polypeptides that is fused to the protein of this invention include arbitrary polypeptides comprising short peptides with few residues, such as tags, and long polypeptides, such as proteins. Specifically, such examples include His tag, HA tag, GFP, maltose binding protein, and glutathione S-transferase (GST). Additionally, antibody fragments (Fc fragment), and such may be also used. Other examples include leader sequence, secretion signal, and preprotein or proprotein sequences, but the present invention is not limited to these examples. Further, a group of polypeptides, that facilitates the polypeptide of this invention to effectively pass the blood-brain barrier, can be fused to the protein of the present invention.

Furthermore, the polypeptides of this invention include salts thereof. Such salts are derived from acids or bases of the polypeptides. Specifically, such salts can be exemplified by salts formed with inorganic acids (for example, hydrochloride, phosphate, hydrobromide, hydrosulfate, nitrate, etc.); salts formed with organic acids (for example, acetate, lactate, formate, butyrate, glycolate, propionate, fumarate, maleate, succinate, tartrate, citrate, malate, oxalate, benzoate, methane sulfonate, benzene sulfonate, etc.); and salts formed with bases (for example, ammonium salt, alkali metal salts such as sodium salt and potassium salt, alkaline earth metal salts such as calcium salt and magnesium salt, and salts formed with organic bases, and salts formed with amino acids such as arginine and lysine).

Furthermore, the polypeptide of the present invention includes derivatives thereof. Herein, the term "derivatives" refers to molecules that have a form, which has been altered by modification, addition, mutation, substitution, or deletion of functional groups of the polypeptide of this invention according to conventional methods. Such alterations of functional groups are carried out, for example, to protect functional groups of the polypeptides, to regulate the stability or histological localization of the polypeptides, or to regulate the activity of the polypeptides, and so on. The polypeptides of the present invention are exemplified by those polypeptides wherein any one of the N-terminus, C-terminus, and functional groups of the polypeptides constituting amino acid side chains are modified by substituents, such as protecting groups. The substituents include, for example, various alkyl groups, acyl groups, amide groups, phosphate groups, amino groups, carboxyl groups, and ester groups; however, the present invention is not limited to these examples.

Furthermore, the polypeptides of the present invention include polymers, such as dimers wherein the polypeptides are bound to each other; branched molecules; and cyclized molecules. Further, the polypeptides may be bound to a carrier. For example, the polypeptides of this invention may be bound to polyethylene glycol (PEG), dextran, other polymers, and so on.

Amino acids that constitute the polypeptides of the present invention may be in the L form and/or D form. The use of D amino acids is effective for lowering degradation by peptidases. Additionally, the amino acids are not limited to natural amino acids, and may be also unnatural amino acids. Unnatural amino acids are exemplified by homoserine, β-hydroxyvaline, 0-4-hydroxyphenyl tyrosine, α-t-butyl glycine, 2-amine butyrate, α-cyclohexyl glycine, α-phenyl glycine, and such. Further, the peptide bonds of the polypeptides may be appropriately substituted with covalent bonds other than peptide bonds. The sensitivity to peptidases of the polypeptides can be lowered by the substitution to non-peptide bonds, which enhances drug efficacy duration and which offers a wide selection of administration routes. The non-peptide bonds are exemplified by imino bonds, ester bonds, hydrazine bonds, semicarbazide bonds, and azo bonds, but the present invention is not limited to these examples.

Further, chemical compounds, that mimic the structure of the polypeptides of the present invention, may be designed. For example, based on the physical and chemical properties (which may be analyzed by conventional methods including active site modification, NMR, and X-ray crystallography) relating to the structure of the polypeptides of this invention a map of physical and chemical functions, that are important for neuroprotective action of the polypeptides, is constructed. Then, molecules that simulate these functions are designed and synthesized. Alternatively, the polypeptides of the present invention are expected to bind to a receptor due to its high activity, and thus, compounds that bind to the same receptor may be designed. Whether molecules derived in this manner possess a neuroprotective action or not can be assayed according to the method described in the Examples.

The present invention also provides DNA encoding a polypeptide of this invention. There is no particular limitation on the origin of the DNA of the present invention, and includes synthetic DNA, genomic DNA, cDNA, and such. The DNA of this invention includes a cDNA that encodes Humanin, described in SEQ ID NO: 4. A DNA having any nucleotide sequence based on the degeneracy of genetic code may be included so long as it encodes the amino acids described in SEQ ID NOs: 5 to 8, 10, 12, 13, 21 to 24, 26 to 29, 32, 33, 37 to 40, 46, 48, 54, or 60. In addition to the coding region, a DNA of the present invention may include non-coding sequences (including non-transcriptional sequence, non-translational sequence, promoter, enhancer, suppressor, transcription factor binding sequence, splicing sequence, poly(A) addition sequence, IRES, mRNA stabilizing/destabilizing sequence, and such) at the 5' and 3' ends.

The DNA of the present invention may be used to produce a polypeptide of this invention by inserting the DNA into a vector. Furthermore, it is also possible to use the DNA for application to gene therapy as described below.

The host to produce a polypeptide of the present invention is not limited in any way, and cells or unities such as *Escherichia coli,* yeast, mammalian cells, plant cells, insect cells, and so on may be used. The host-vector system may be, for example, the baculovirus-Sf cell line (Okamoto et al., J. Biol. Chem. 270: 4205-4208, 1995); the pcDNA-CHO cell line (Takahashi et al., J. Biol. Chem. 270:19041-19045, 1995); the CMV promoter plasmid-COS cell line (Yamatsuji et al., EMBO J. 15:498-509, 1996); and such, but are not limited thereto.

The polypeptides of the present invention may be secreted from host cells. As described in the Examples, Humanin, HNG, and such were secreted from cells, wherin the polypeptides were expressed to the extracellular region, and the secreted polypeptides antagonized neuronal death. When secreted to the cell exterior, the polypeptides of the present invention can be conveniently recovered from the culture supernatant of the host cells.

The polypeptides of the present invention or DNAs that encodes the polypeptides of the present invention can be made into reagents for suppressing neuronal death. A DNA of the present invention can be appropriately inserted into a vector, and the vector can be used as a reagent. In addition to using a polypeptide or DNA itself as the reagent, a reagent that includes a polypeptide of this invention or a DNA that encodes a polypeptide of this invention may be appropriately combined with sterilized water, saline solution, buffer, salts, stabilizers, preservatives, detergents, other proteins (BSA, etc.), transfection reagents (including lipofection reagent), and such. These may be mixed in advance, or may be kept separately until they are mixed before use.

Cell death of neurons can be suppressed by contacting a polypeptide of the present invention to the neuron. A polypeptide of this invention is contacted to the outside of a cell. Specifically, a polypeptide of the invention is added to the culture medium in a cell culture system. For use in vivo, a polypeptide of the invention is administered so that the polypeptide will be contacted to the cell, which is the target, to suppress cell death. Although the concentration of a polypeptide of the invention depends on the strength of the activity to suppress neuronal death and the purpose of the use thereof, the maximum activity of the polypeptide is reached at a concentration of about 10 µM or less if the polypeptide possesses an activity equivalent to that of HN, and at about 10 nM or less if the polypeptide possesses an activity equivalent to that of HNG. If the polypeptides are secretory polypeptides, the polypeptides will be secreted to the cell exterior, even when it is introduced or expressed intracellularly, and thus, cell death can be suppressed. For example, to suppress cell death with secretory polypeptides, a DNA encoding a polypeptide of the invention is expressed intracellularly. Cell death of neurons can be suppressed in cell culture systems or in vivo by introducing a vector that expresses a polypeptide of the present invention into a cell. Additionally, co-culturing with cells expressing a secretory polypeptide of this invention, or ex vivo administration of the secretory polypeptides enables to suppress cell death of surrounding cells.

Accordingly, a polypeptide of the present invention, a DNA encoding the polypeptide, and a vector containing the DNA may be used to suppress neuronal death. These act as neuronal death suppressant. Furthermore, the present invention provides use of the polypeptides of the invention, DNAs encoding the polypeptides, and vectors containing the DNAs for suppressing neuronal death.

The present invention also provides pharmaceutical compositions containing a polypeptide of this invention, or a vector, wherein a DNA encoding a polypeptide of this invention has been inserted, as its active ingredient. A polypeptide of the present invention can protect cells from neurodegeneration by adding the polypeptide extracellularly, or by intracellular expression of a secretory form of the polypeptide. Therefore, a polypeptide of this invention is useful as a pharmaceutical composition particularly active against diseases associated with neurodegeration.

As described in the Examples, chemically synthesized Humanin (HN) polypeptide suppresses neuronal death at a concentration of about 10 nM or more in the extracellular solution, and a maximum suppression is achieved at a concentration of 1 to 10 µM. On the other hand, HNG and AGA-HNG polypeptides showed significant or sufficient neuroprotective action at about 1 nM. The neuroprotective action is presented by introducing and expressing a DNA encoding the polypeptides in the cell. Therefore, a vector expressing a polypeptide of this invention as a medicament may be used to perform gene therapy. Secretor types of the polypeptides, or polypeptides, modified with secretion signal attachment, may be expressed for the gene therapy. Administration methods for the vectors include in vivo and ex vivo methods. Vector systems for gene therapy include: adenovirus vector; AAV (adenovirus-associated virus) vector; herpesvirus vector (all refer to Robbins and Ghivizzani, Pharmacol. Ther. 80:35-47, 1998); retrovirus vector (Engel and Kohn, Front. Biosci. 4:e26-33, 1999); lentivirus vector (Lundstrom, K., 1999, J. Recept. Signal. Transduct. Res. 19:673-686); and such, but are not limited thereto.

The target diseases to be prevented or treated using a polypeptide of the present invention, or using a vector that expresses the polypeptide is not limited in any way, so long as the used polypeptide of the present invention is effective for treating the disease. Examples of preferred target diseases include neuron-related diseases, in particular Alzheimer's disease. Previous studies having revealed that cell death of neurons occurs in Alzheimer's disease (T. Nishimoto et al., 1997, Adv. Pharmacol., 41:337-368). Some sort of activation of APP (I. Nishimoto et al., 1998, Neurobiol. Aging., 19:S33-S38) and presenilin (Nishimura et al., 1999, Clin. Genet. 55:219-225) are suggested to be associated with the cell death. Therefore, pharmaceutical compositions of this invention are expected to be applicable as medicament for protection against neurodegeneration that occurs in Alzheimer's disease. In addition to Alzheimer's disease, for example, diseases caused by cell death of neurons due to cerebral ischemia (T. Kirino, 1982, Brain Res., 239:57-69) can be prevented by the use of a pharmaceutical composition of the present invention. Further, Parkinson's disease that accompanies dementia (M. H. Polymeropoulos et al., 1997, Science, 276:2045-2047); diffuse Lewy bodies disease (M. G. Spillantini et al., 1998, Proc. Natl. Acad. Sci. USA, 95:6469-6473); dementia that accompanies Down's disease; and such are also targets of the treatment and prevention using a protein of the invention. Furthermore, since APLP1, which is an APP analogue, is said to be the causative gene for congenital nephrotic syndrome (Lenkkeri, U. et al., 1998, Hum. Genet. 102:192-196), renal diseases, such as nephrotic syndrome, is also the target for the treatment and prevention.

In addition to the direct administration of the active ingredient to a patient, a pharmaceutical composition of this invention may be formulated following conventional drug implementations. For example, the composition may be administered after appropriately formulating it with pharmacologically acceptable carriers or medium, specifically, sterilized water or saline, vegetable oils, emulsifiers, suspending agents, detergents, stabilizers, sustained-release preparations, and such. A pharmaceutical composition of this invention may be in the form of an aqueous solution, tablet, capsule, troche, buccal tablet, elixir, suspension, syrup, nasal drop, inhalant solution, and such. The content of the polypeptide in these preparations makes a suitable dosage acquirable.

Administration to patients may be carried out depending on the properties of the used active ingredient. Example of suitable administration methods include percutaneous, intranasal, transbronchial, intramuscular, intraperitoneal, intravenous, intraspinal, intracerebroventricular, or oral administrations, but are not limited thereto. When using the pharmaceutical composition in the treatment of cerebral neurodegenerative diseases, it is preferable to introduce the pharmaceutical composition to the central nervous system by an appropriate arbitrary route including a intravenous, intraspinal, intracerebroventricular, or intradural injection. The dosage varies according to the age, body weight, condition of a patient, method of administration, and such, but one skilled in the art can suitably select them. The dosage and administration method varies depending on the histological localization of the active ingredient of the pharmaceutical composition of the present invention, therapeutic purpose, body weight, age, and condition of a patient, and such, but can be selected suitably by those skilled in the art.

For example, to protect cerebral neurons against degeneration in Alzheimer's disease treatment, it is preferable to administer a polypeptide of the present invention so that the concentration around the target cells is sufficient to effectively suppress neurodegeneration. Specifically, Humanin polypeptide or compounds, that have equivalent protective action against neuronal death with Humanin, should be administered at a concentration of at least 1 nM or more, preferably 10 nM or more, more preferably 100 nM or more, and much more preferably 1 µM or more. HNG or comounds, that have equivalent protective action against neuronal death with HNG, should be administered at a concentration of at least 1 pM or more, preferably 10 pM or more, more preferably 100 pM or more, and much more preferably 1 nM or more. On the other hand, a comparable effect with HNG can be expected by the use of AGA-HNG, at a concentration of a tenth of the HNG concentration. The dosage to achieve these concentrations can be appropriately determined taking the administration route into consideration.

The present invention also provides antibodies binding to a polypeptide of the invention. The antibodies of this invention include polyclonal antibodies and monoclonal antibodies. Polyclonal antibodies can be prepared, for example, as follows: a polypeptide of the invention, such as HN and HNG, or partial peptides thereof are prepared; rabbit, goat, sheep, and such are sensitized with these peptides as the antigen. Antigenic peptides can be bound to other proteins according to needs. For example, they can be bound with carrier proteins, such as key-hole limpet hemocyanin and albumin for immunization. Monoclonal antibodies can be prepared using splenocytes of immunized mice and rats to obtain hybridomas that produce monoclonal antibodies. Production of antibodies can be carried out according to conventional methods (Ed. Harlow and David Lane, Antibodies: A Laboratory Manual, Cold Spring Harbor Laboratory, 1988).

Using conventional biochemical techniques, such as ammonium sulfate fractionation, protein G sepharose column, and affinity column with immobilized antigens, polyclonal antibodies can be purified from serum, and monoclonal antibodies can be purified from hybridoma culture supernatant or from ascites of animals inoculated with hybridoma.

Additionally to the use of the antibodies prepared in this manner to absorb the polypeptide of this invention, the antibodies may be utilized, for example, to test and diagnose structural alterations of a polypeptide of this invention, and to detect the expression level of a polypeptide of this invention.

Decrease in blood or interstitial concentration of Humanin or Humanin-like peptide, including concentration in the nerve tissue, may be used to diagnose or prognosticate degenerative diseases of the nerves, including AD, and degenerative diseases of other organs. For example, it is possible that the progress of the disease of AD patients with low HN activity in blood is faster with bad prognosis compared to patients of the same kind of AD with high HN activity. Conceivable methods for testing are exemplified by measuring the concentrations of a pepetide of the invention in the blood or tissue samples by RIA using anti-Humanin antibody, or by testing biopsy samples by immunohistological staining. Furthermore, for example, the polypeptide level can be monitored during the treatment which includes administration of a polypeptide of this invention.

The antibodies of the present invention may be antibody fragments thereof, so long as it binds to a protein of the invention. For example, the antibody fragment may be Fab, $F(ab')_2$, Fv, or modified antibodies thereof. Additionally, humanized antibodies or human antibodies, and such are also included in the antibodies of the present invention. An antibody of the present invention can be used as "a test reagent for a polypeptide of this invention", and additionally, it can be appropriately combined with sterilized water, saline solution, buffer, salts, stabilizers, preservatives, detergents, other proteins (BSA, etc.), and such. These may be mixed in advance or may be kept separately until they are mixed at the time of use.

The present invention also provides a DNA comprising at least 15 nucleotides, which is a complementary to a DNA (SEQ ID NO: 4) encoding Humanin or complementary strand thereof, and are used to detect or manipulate a gene encoding a polypeptide of this invention. The term "detection of a gene" refers to a detection based on a gene including the detection of the existence, mutations, expression, and such of a gene. The term "manipulation of a gene" refers to gene manipulations, such as introduction of mutation(s) to a gene; amplification of a gene; and inhibition of the expression of a gene. The term "detection or manipulation of a gene" includes detection and regulation of the expression of a gene. Herein, the term "complementary strand" is defined as one strand of a double strand DNA composed of A:T and G:C base pair to the other strand. Also, "complementary" is defined as not only those completely matching within a continuous region of at least 15 nucleotides, but also those having a homology of 70% or more, preferably 50% or more, more preferably 80% or more, even more preferably 90% or more (for example, 95% ore more) within that region. The homology may be determined, for example, according to a method described in the literature (Altschul, S. F. et al., 1990, J. Mol. Biol. 215:403-410).

Such DNA includes, probes and primer for detecting or amplifying DNAs or RNAs encoding a peptide of the invention; as well as nucleotide and nucleotide derivatives (for example, antisense oligonucleotides, DNAs encoding ribozymes, and such) for suppressing the expression of a polypeptide of this invention. When used as a primer, such a DNA is complementary at the 3'-end, and restriction enzyme recognition sequences or tags can be added to the 5'-end.

Further, the present invention provides a method for detecting the activity of a polypeptide of this invention to suppress cell death. The method comprises: (a) inducing cell death in the presence of a polypeptide of this invention; and (b) detecting level of cell death. Specific manipulation of the method can be carried out according to the method described herein. The method may be used to determine whether a polypeptide of the invention has the effect to suppress cell death in various cells, and to quantify the suppressive effect. There are no particular limitations on the cells to be used in the method, and various cells that may encounter cell death can be used. Further, induction of cell death can be carried out using cell death induction system for respective cells known in the art. Neurons may be used to detect the effect of a polypeptide of the invention on various conditions, such as neuronal death-inducing stimuli, environmental changes, and gene expression. The detection method can also detect differences of sensitivity against a polypeptide of the invention in neuronal death existing among biological species or subspecies, and between individuals. This enables to analyze the effectiveness of a polypeptide of the invention, for example, among ethnic groups, race, or individuals. According to the method, for example, detailed analysis of conditions for clinical application of a polypeptide of the invention can be carried out.

Further, the present invention provides a method for detecting the effect of chemical compounds on the suppression of neuronal death by a polypeptide of the invention. The method comprises the steps of: (a) inducing neuronal death in the presence of a polypeptide of the present invention and a test compound; and (b) detecting the level of neuronal death. The method may be used to assay chemical compounds that enhance or suppress neuronal death by a polypeptide of the invention. A polypeptide of the present invention is suggested to exhibit a cell death suppressing effect by acting to the neuronal surface. The action of a candidate compound that inhibits, or on the contrary enhances contact of a polypeptide of the invention to the cell surface can be investigated according to the method. Alternatively, the use of the detection method enables screening of chemical compounds that regulate the suppression of neuronal death by a polypeptide of the invention. The method comprises the steps of: (a) inducing neuronal death in the presence of a test compound and a polypeptide of the present invention; (b) detecting the level of neuronal death; and (c) selecting the chemical compound that enhances or suppresses neuronal death. In step (c), the result can be compared to that with arbitrary control. More specifically, for example, one can select in step (c) the chemical compound that enhances or suppresses neuronal death in the presence of a test sample compared to those detected in the absence of a test sample. Chemical compounds that enhance neuronal death serve as candidate compounds, inhibiting the suppression of neuronal death by a polypeptide of the invention; whereas chemical compounds that suppress neuronal death serve as candidate compounds, further enhancing the suppression of neuronal death by a polypeptide of the invention. Alternatively, a different compound other than the test sample can be used as a control in the above-mentioned screening method. Specifically, cell death are detected using compounds, other than the test sample, that regulate the suppression of neuronal death by a polypeptide of the invention; selecting in step (c) the chemical compounds from the test samples in step (a), which compounds suppresses or enhances neuronal death compared to the result obtained with the other compound. According to the screening method, chemical compounds having stronger effects compared to existing compounds can be screened with respect to their ability to regulate the suppression of neuronal death by a polypeptide of the invention.

Test samples for the screening include, for example, purified proteins (including antibodies); expression products of gene libraries; synthetic peptide libraries; cell extracts; cell culture supernatants; libraries of low-molecular weight synthetic compounds; natural materials, such as soil; solutions containing substances released from bacteria such as Actinomyces broth; and so on, but are not limited thereto.

Induction on neuronal death and administration of a polypeptide of the invention can be carried out according to the Examples. There is no particular limitation on the timing of the application of a test sample to cells, and they may be applied before, after, or simultaneously with the application of a polypeptide of the invention. Further, there is no limitation on the method for the application of a test sample, and for example, the sample is added to the medium of a cultured cell line. If the sample is a nucleic acid, it can be introduced into a cell. In addition to the methods above, the test sample can be applied by arbitrary administration methods.

Chemical compounds evaluated by the action of the compounds in the above-mentioned test, or compounds obtained by the screening serve as candidate compounds that regulate the activity of a polypeptide of the invention. These compounds may be applied to prevent or treat diseases associated with Alzheimer's disease.

Further, the present invention provides a method of screening for compounds that bind to a polypeptide of the invention. Such screening can be performed by a method comprising the steps of: (a) contacting a polypeptide of the present invention with a test sample; (b) detecting the binding activity between the polypeptide of the invention and the test sample; and (c) selecting the sample that bind to the polypeptide of this invention.

Depending on the screening method, a polypeptide of the invention may be used in the screening as a soluble polypeptide, or in a form bound to a support. A polypeptide of the invention may be labeled. Examples of labeling include labeling by radioactive isotopes, fluorescent substances, and biotin or digoxigenin; tag sequence addition; and such.

Test samples for the screening may be, for example, purified proteins (including antibodies); expression products of gene libraries; synthetic peptide libraries; cell extracts; cell culture supernatants; libraries of low-molecular weight synthetic compounds; natural materials, such as soil; solutions containing substances released from bacteria, such as Actinomyces broth; and so on, but are not limited thereto. Test samples to be used in the screening may be appropriately labeled according to needs. The labels include, for example, radioactive labels, fluorescent labels, and such, but are not limited thereto.

For example, screening for proteins, that bind to a polypeptide of the present invention, can be carried out by applying cell extract of tissues or cells, expected to express proteins that bind to a polypeptide of this invention, to an affinity column to which a polypeptide of this invention is immobilized; and purifying the proteins that specifically bind to the column.

Alternatively, a cDNA library is prepared from tissues or cells, expected to express proteins that bind to a polypeptide of the invention (for example, brain cortical tissue; and neurons, such as F11) using phage vectors; then plaques are formed on agarose; and screening by Western blotting is carried out using labeled polypeptides of this invention. The screening can be also conducted by a "two hybrid system", and so on. Specifically, a method utilizing a "two hybrid system" is conducted as follows: (1) a DNA-binding peptide, such as GAL4 DNA-binding region, and a transcription activating peptide, such as GAL4 transcription activation region, is expressed as a fusion protein with a polypeptide of the present invention and a test protein, respectively; and (2) the binding of the protein of the present invention and the test protein is detected as the expression of a reporter gene attached downstream of a promoter, having a binding sequence of the DNA binding peptide.

Furthermore, receptors of a polypeptide of the present invention can be cloned by the screening method of this invention. In case of screening receptors, it is preferable to prepare the test samples from tissues or cells, expected to express receptors (for example, brain cortical tissue, nerve cell line, neuroblastoma cells, and teratocarcinoma cells). Examples of nerve cell lines include F11 cells; PC12 cells (L. A. Green and A. S. Tischler, 1976, Proc. Natl. Acad. Sci. USA, 73:2424-2428); NTERA2 cells (J. Skowronski and M. F. Singer, 1985, Proc. Natl. Acad. Sci. USA, 82:6050-6054); SH-SY5Y cells (L. Odelstad et al., 1981, Brain Res., 224: 69-82); and so on.

Alternatively, molecules binding to a polypeptide of the present invention can be screened by contacting synthetic compounds; natural product bank; and random phage peptide display libraries to an immobilized polypeptide of the invention. Further, screening by detecting the binding utilizing surface plasmon resonance imaging (for example, manufactured by BIAcore) is possible. These screening methods may be performed by high-throughput screening utilizing combinatorial chemistry techniques.

Compounds, that bind to a polypeptide of the present invention, obtained according to the screening method of this invention, serve as candidate compounds, regulating the activity of a polypeptide of the invention. Thus, these compounds are applicable to prevent or treat diseases associated with Alzheimer's disease.

DNA fragments were aligned with respect to the longest sequence (from −934 to 600); the number 1 nucleotide corresponds to the first nucleotide of Humanin ORF, and the nucleotide adjacent to it is numbered −1). Activities of the fragments against F11/EcR cell death induced by V642I APP are indicated under the item "rescue activity". F11/EcR cells were transfected for 3 hours with pIND (1 μg), encoding V642I APP, and 1 μg of either pEF-BOS or pEF-BOS encoding each of the DNA fragments; and then, were treated with ecdysone for 72 hours. Cell death was measured by trypan blue exclusion assay. A DNA fragment was determined to antagonize cell death (described as "Y" under the item "rescue activity") when the mortality of cells transfected with the DNA fragment showed a statistically significant difference with that of cells transfected with pEF-BOS. "N" indicates the absence of such a significant antagonizing activity.

Figure 1:
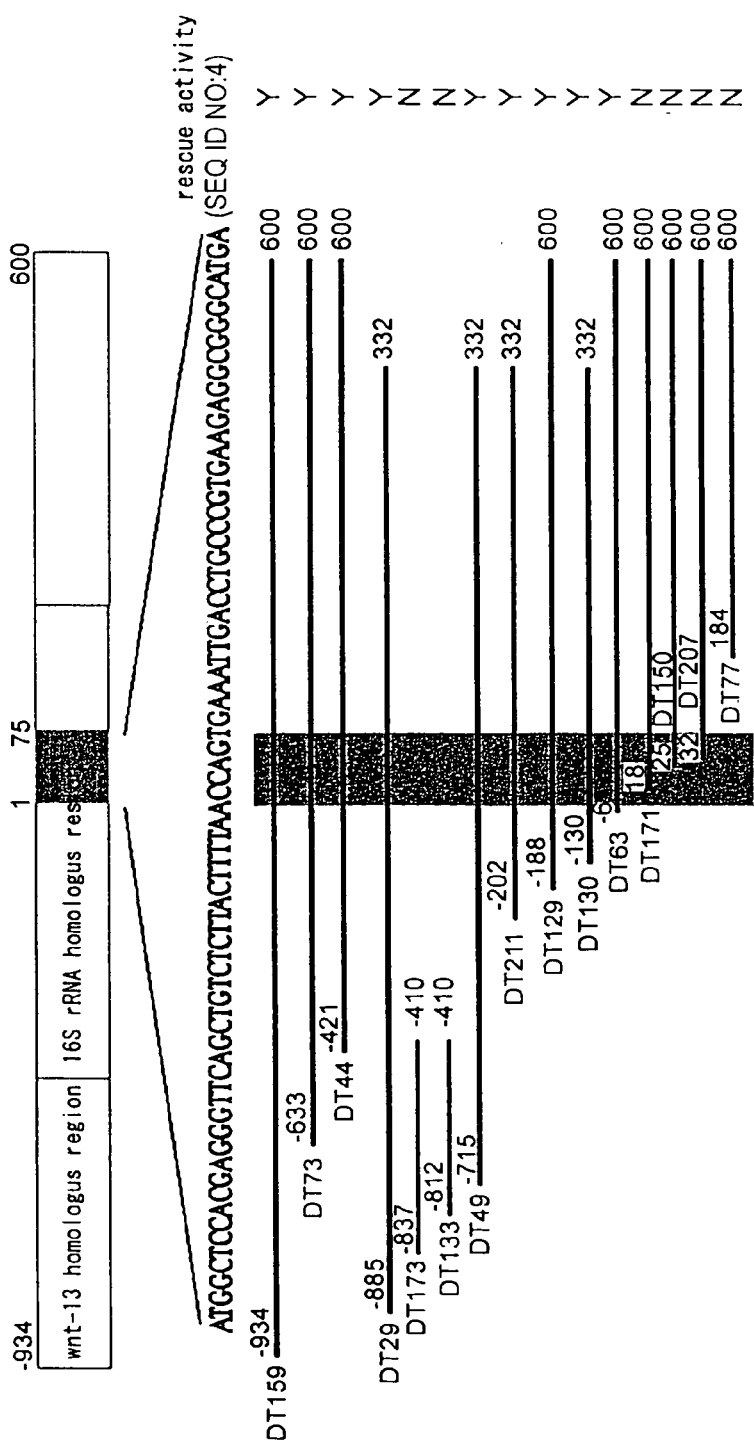
FIG. 1 depicts a schematic illustration of the region in Humanin cDNA clone (SEQ ID NO: 4) that encodes a polypeptide that antagonizes cell death caused by V642I APP.
Figure 2:
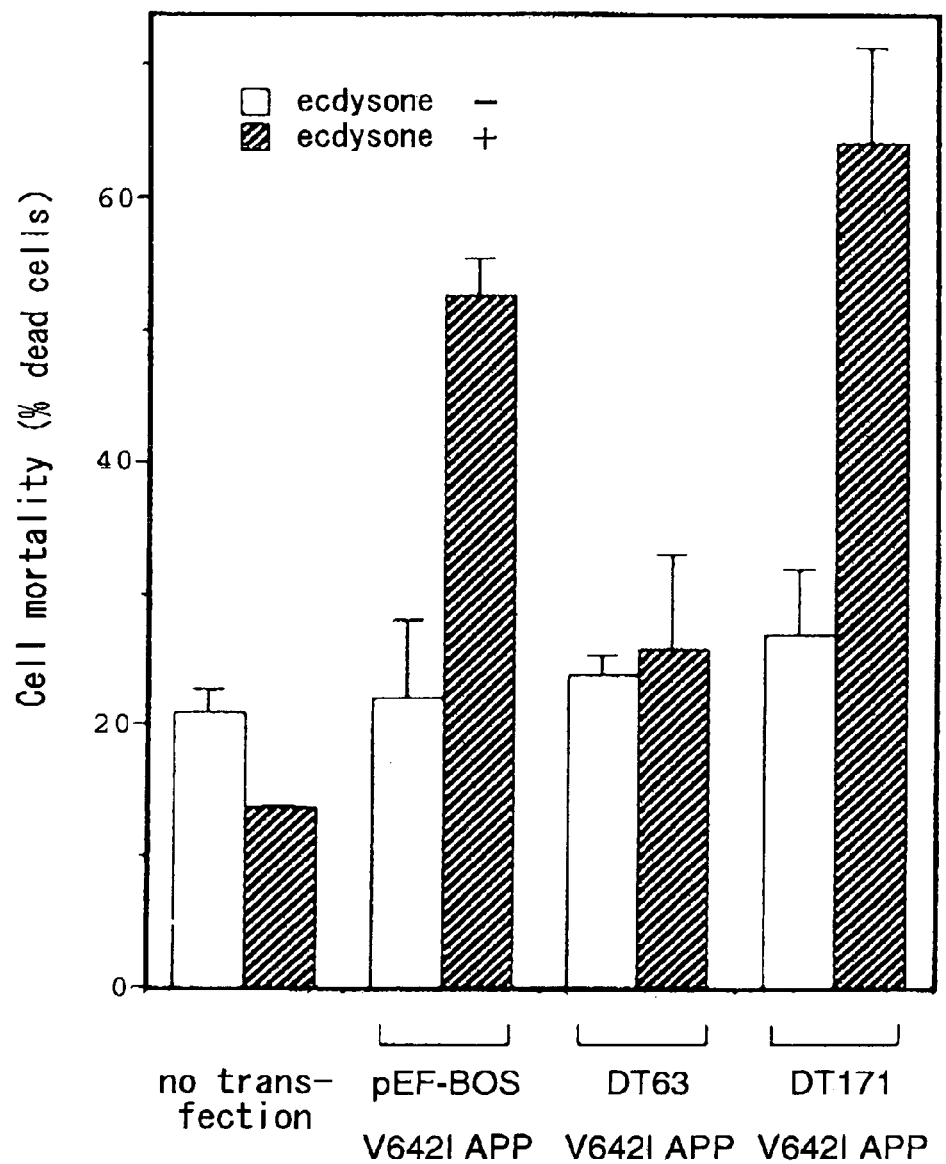

FIG. 2 depicts a graph demonstrating the effects of DT63 clone and DT171 clone on neuronal death caused by V642I APP. F11/EcR cells were transfected with ecdysone-inducible V642I APP plasmid, and any one of pEF-BOS, DT63, or DT171 (DT63 and DT171 were cloned in pEF-BOS), and were treated with Ponasterone (ecdysone). A group without ecdysone treatment was also set up. 72 hours after ecdysone treatment, cell death was measured by trypan blue exclusion assay. Cell death of the group without ecdysone treatment was measured similarly. The values with error bars in the graph represent mean ±S.D. values of three independent transfection experiments. DT63 and DT171 are shown in FIG. 1.

Figure 3:
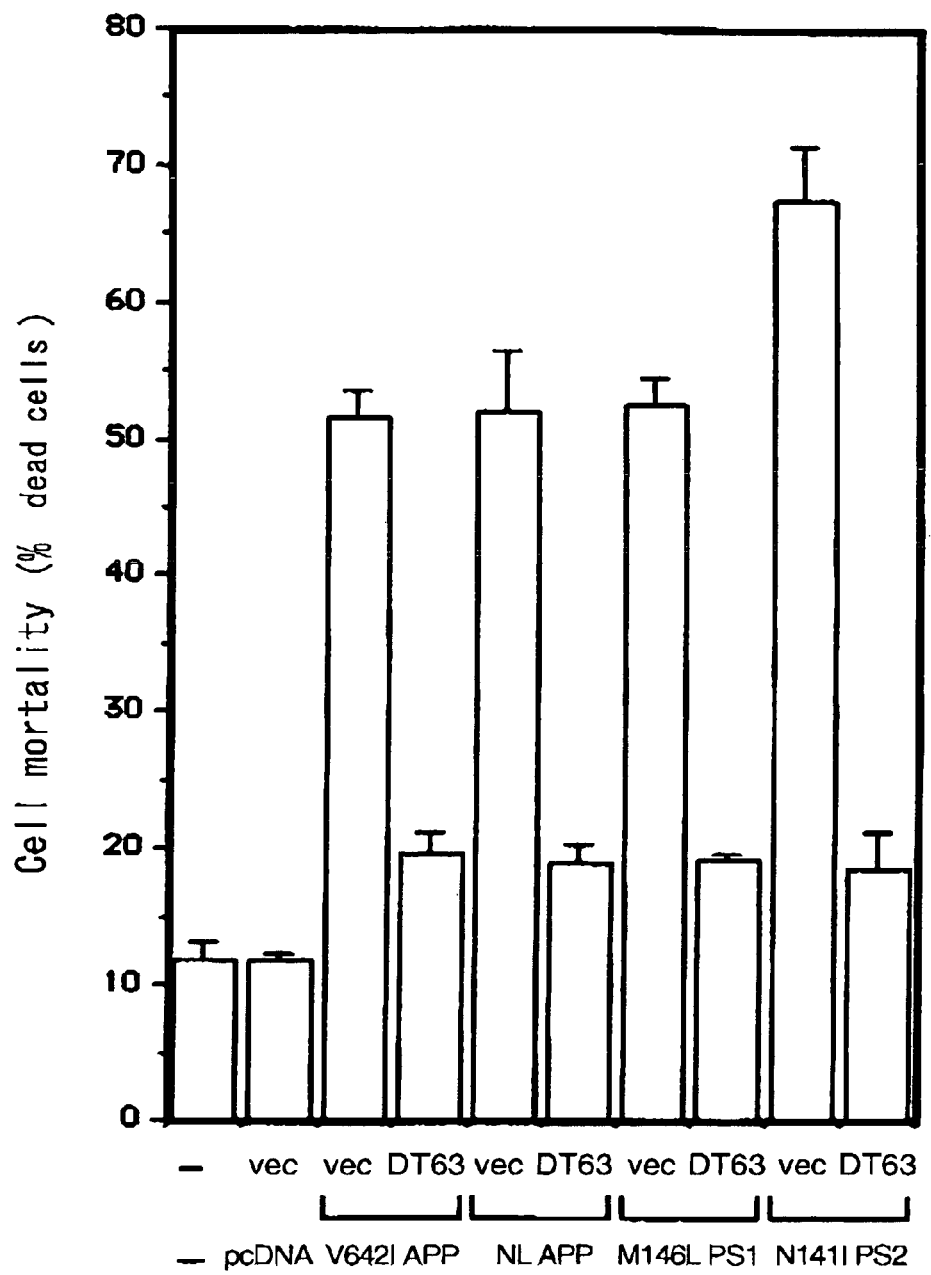

FIG. 3 depicts a graph demonstrating the effect of DT63 clone on neuronal death induced by the expression of the FAD gene. F11 cells were transfected with pcDNA; or pcDNA encoding V642I APP, NL-APP, M146L PS-1, or N141I PS-2; and pEF-BOS (vec); or pEF-BOS encoding DT63; and were cultured for 72 hours. Cell death was measured by trypan blue exclusion assay. The values with error bars in the graph indicate the mean ±S.D. values of three independent transfection experiments.

Figure 4:
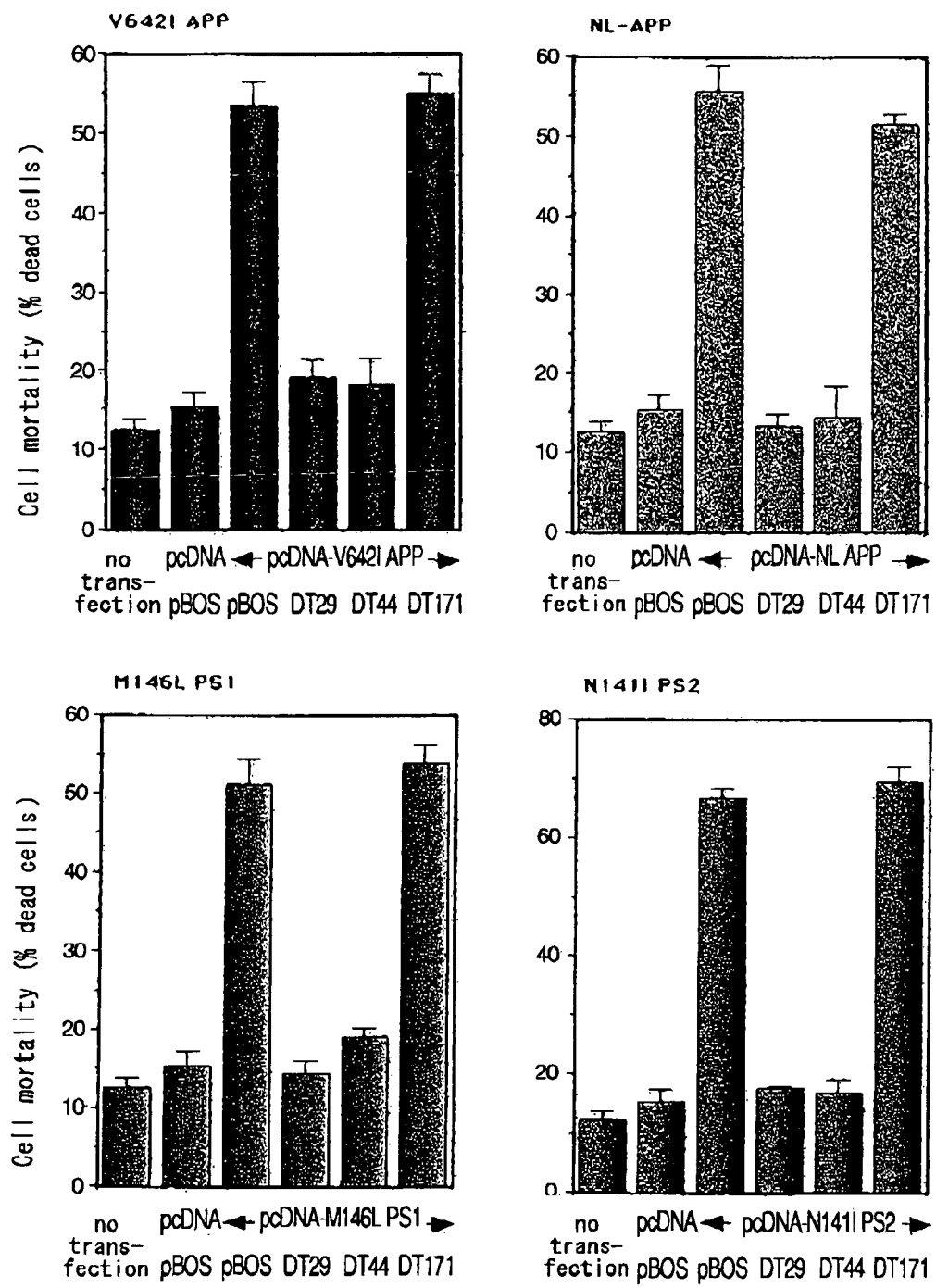

FIG. 4 depicts graphs indicating the effects of DT29, DT44, and DT171 clones of F11 cell death caused by FAD gene transfection. Similarly to FIG. 3, F11 cells were transfected with pcDNA; or pcDNA encoding either V642I APP, NL-APP, M146L PS-1, or N141I PS-2; and pEF-BOS (pBOS); or pEF-BOS encoding DT clone; and were cultured for 72 hours. Cell death was measured by trypan blue exclusion assay. DT29 and DT44 are shown in FIG. 1. Basal cell mortality (no transfection, pcDNA+pBOS) was concordant in the three experiments performed simultaneously. Similar experiments were performed at least three times. The values with error bars in the graph indicate the mean ±S.D values.

Figure 5:
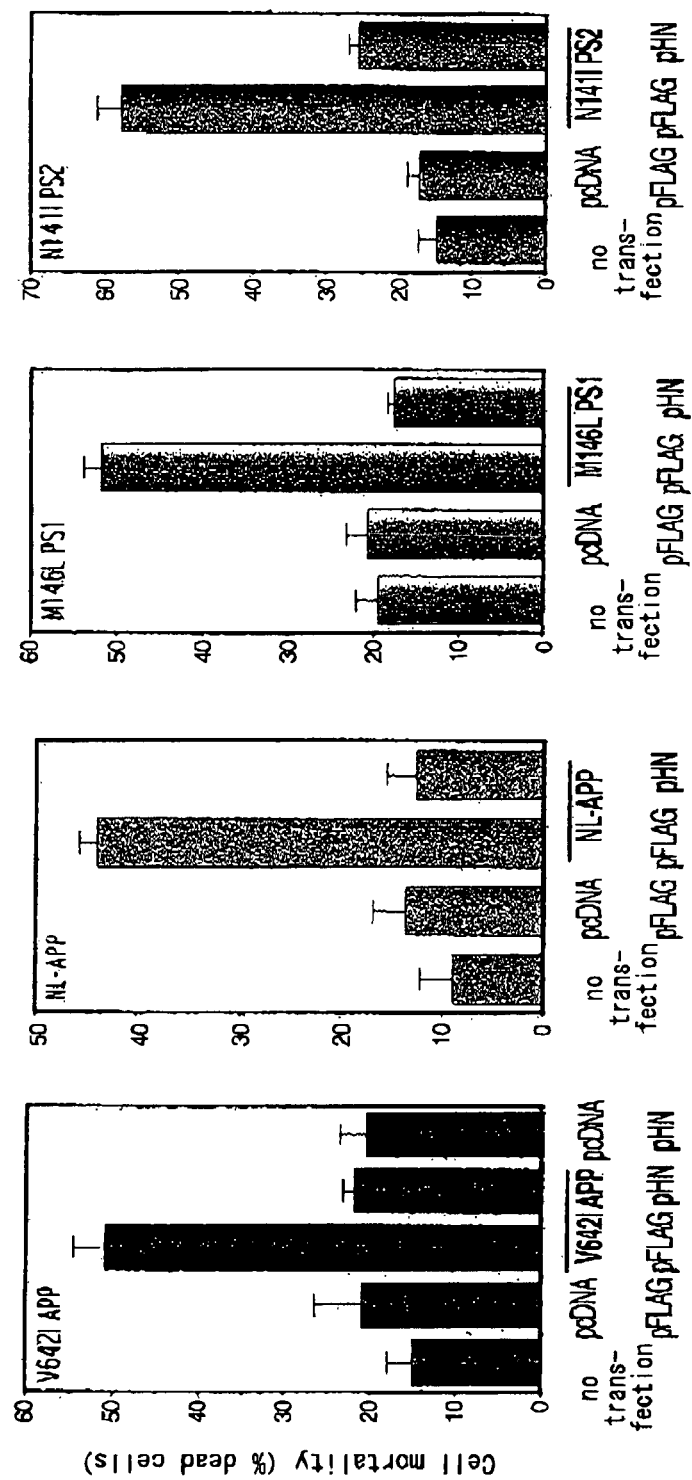

FIG. 5 depicts graphs demonstrating the effect of Humanin-encoding plasmid pHN on neuronal death induced by expression of a FAD gene. F11 cells were transfected with an empty vector (pcDNA); or pcDNA encoding V642I APP, NL-APP, M146L PS-1, or N141I PS-2; and pFLAG; or pFLAG encoding HN (pHN); and were cultured for 72 hours. Cell death was measured by trypan blue exclusion assay. The values are mean ±S.D. values obtained by three independent experiments.

Figure 6:
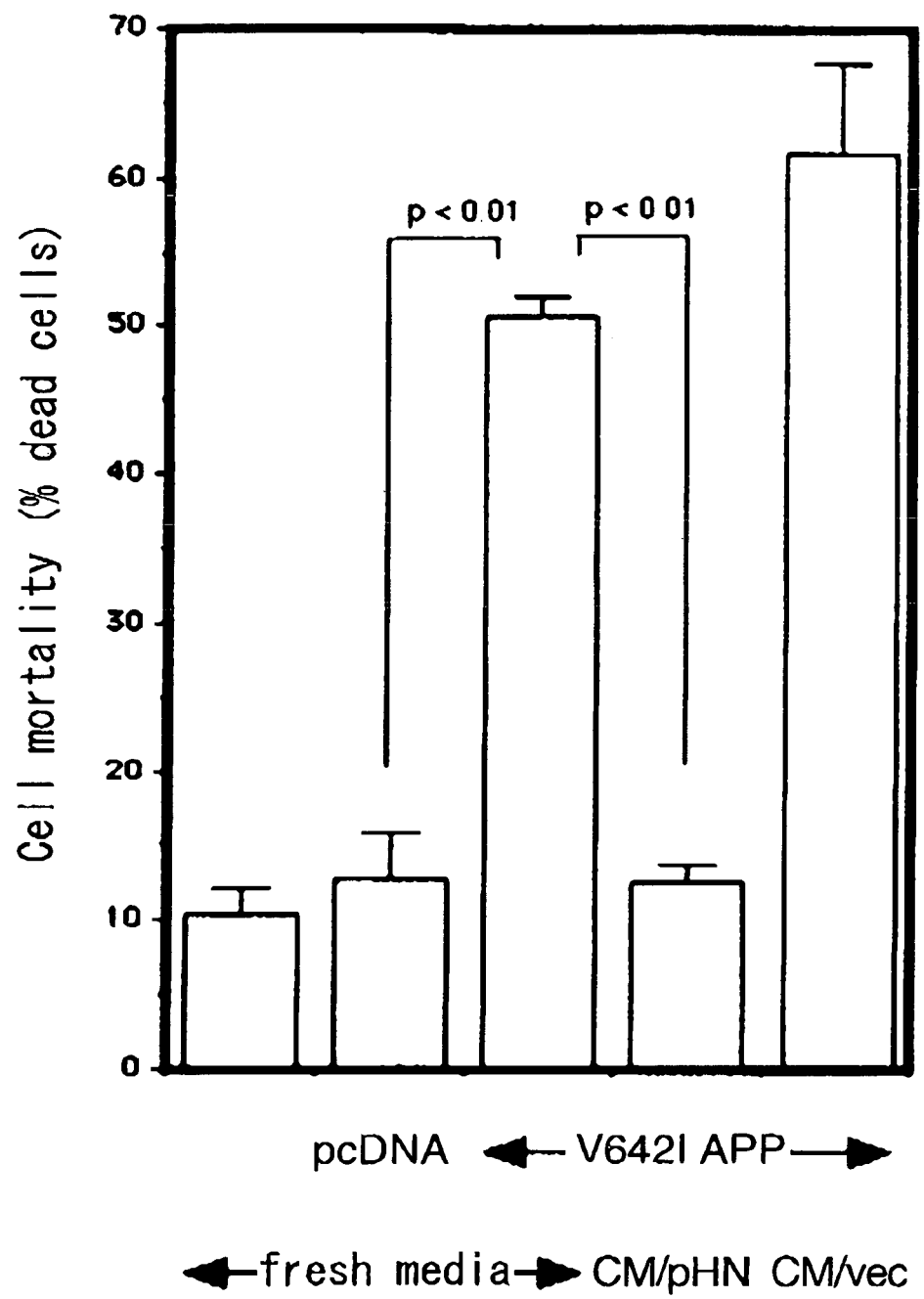

FIG. 6 depicts a graph demonstrating the suppressive effect of a culture supernatant from pHN-transfected F11 cells on neuronal death induced by V642I APP. F11 cells were transfected for 3 hours with either pcDNA or pcDNA encoding V642I APP, in the absence of serum; cultured in HamF-12 containing 18% FBS for 2 hours; and cultured in CM/F11-pHN (CM/pHN), CM/F11-vec (CM/vec), or fresh media (fresh HamF-12 containing 18% FBS) for 67 hours. 72 hours after the transfection, cell death was measured by trypan blue exclusion assay. The values are indicated as mean ±S.D. values of three independent experiments. $p<0.01$; according to a Student's t test.

Figure 7:
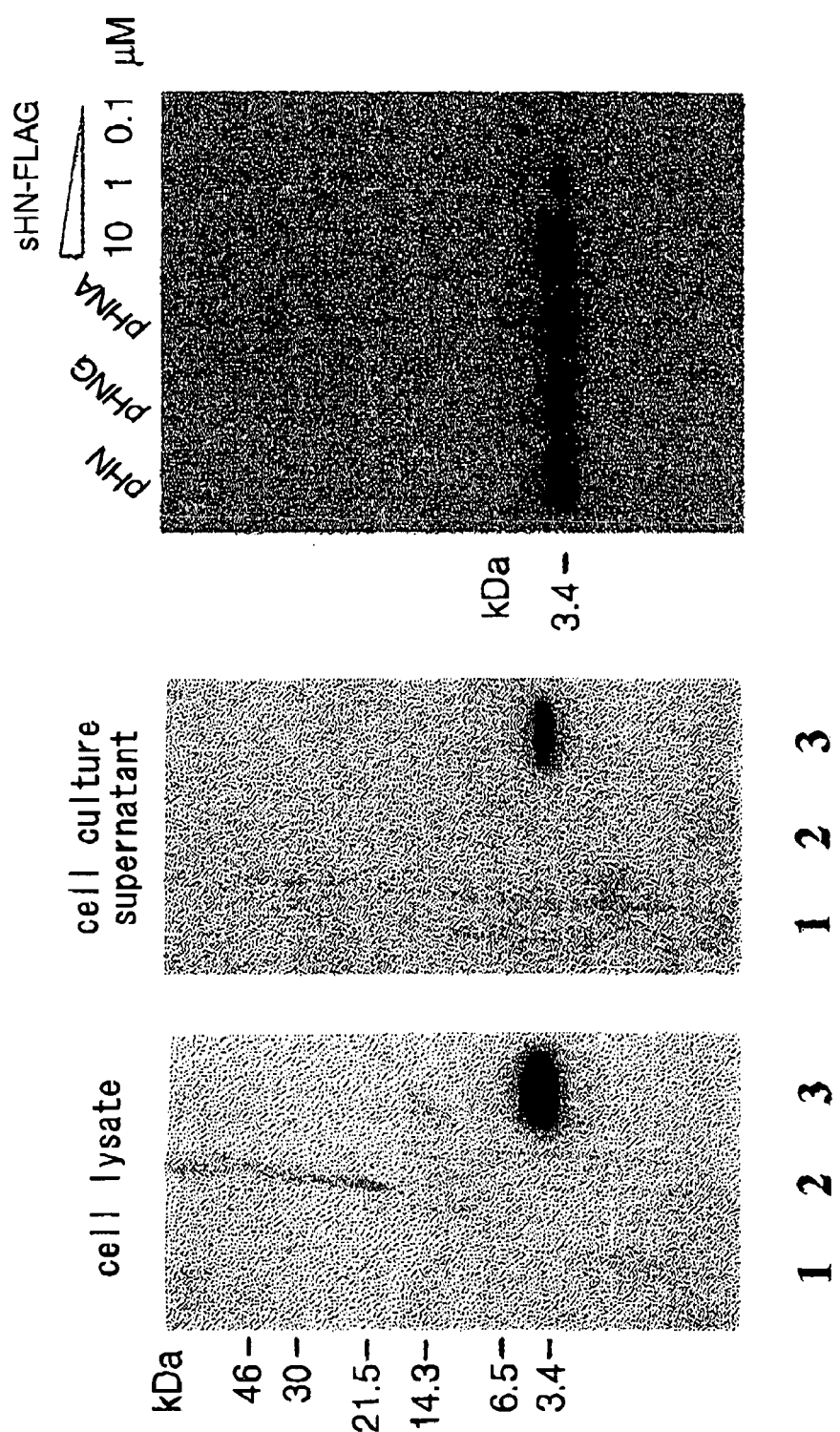

FIG. 7 depicts photographs demonstrating the immunoreactivity of HN polypeptides contained in the culture supernatant of F11 cells transfected with pHN. The left and middle panels demonstrate the result of immunoblotting using anti-FLAG antibody on cell extracts (30 μg protein) and culture supernatant (20 μl) following Tris/Tricine gel electrophoresis (lane 1: cells with no transfection; lane 2: pFLAG-transfected cells; lane 3: pHN-transfected cells). The right panel demonstrates the result of a similar analysis on the culture supernatant of cells transfected with pHN, pHNG, or pHNA. The 3 lanes on the right demonstrate the results of immunoblotting on sHN-FLAG (MAPRGFS-CLLLLTSEIDLPVKRRAGTDYKDDDDK: the underlined region is a FLAG tag) (SEQ ID NO: 6) with indicated concentrations, to determine the titer of HN polypeptides contained in the culture supernatant. Similar experiments were repeated 4 times or more.

Figure 8:
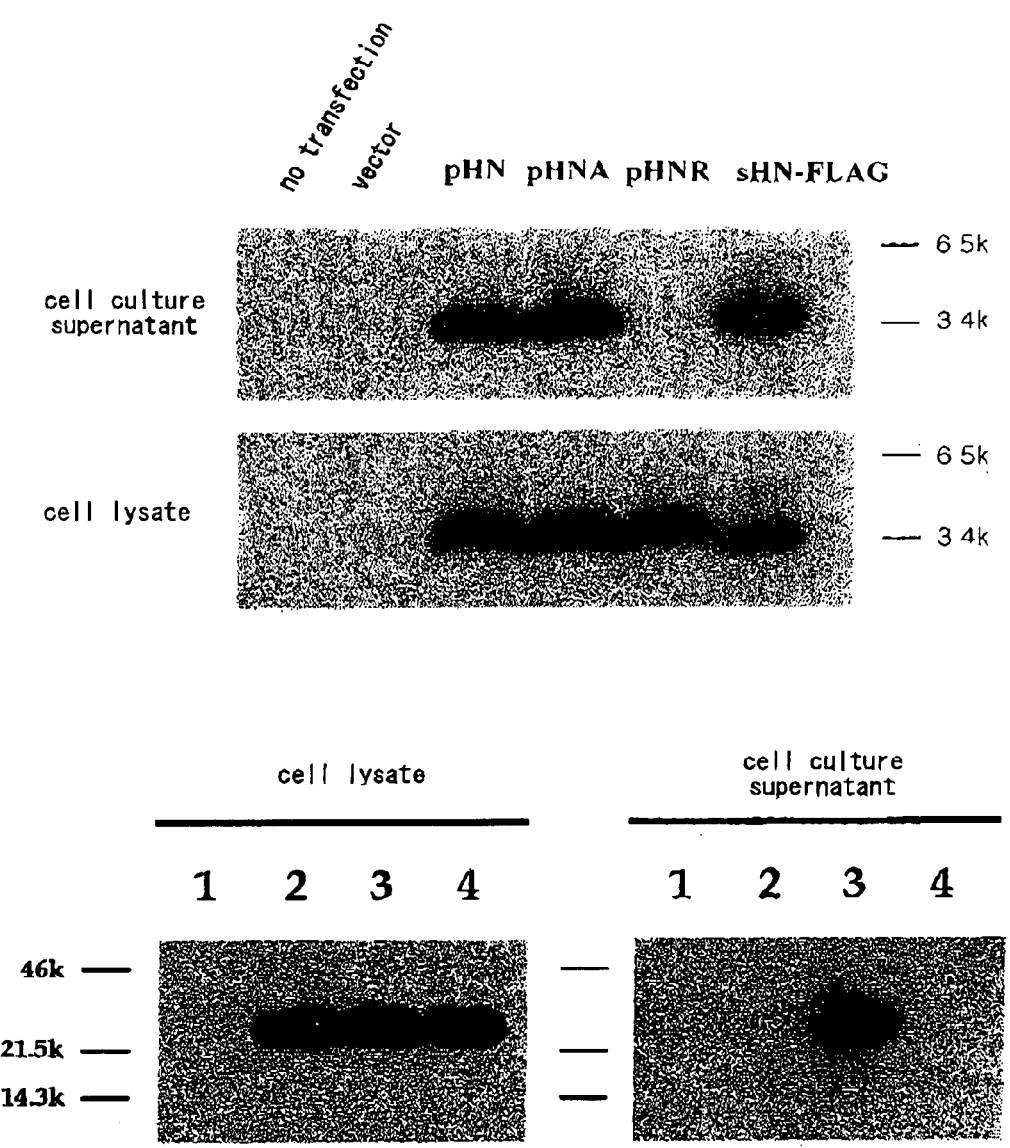

FIG. 8 depicts photographs demonstrating the result of analysis on cellular secretion of HN polypeptide and mutants thereof. Top panel: photographs demonstrating that extracellular secretion of HN is inhibited due to the L9R mutation. F11 cells were transfected with pHN, pHNA, or pHNR (pFLAG that encodes L9R HN); then 72 hours later, the cell extracts and culture supernatant were collected and analyzed by anti-FLAG antibody, similarly to FIG. 7.

Lower panel: photographs demonstrating signal sequence-like secretion activity of HN. F11 cells were transfected with EGFP cDNA (lane 2), HN-EGFP fusion cDNA (lane 3), or HNR-EGFP cDNA (lane 4); after 72 hours, cell extracts (lower left panel, 10 μg/lane) or culture supernatant (lower right panel, 20 μg/lane) were analyzed by immunoblotting with anti-EGFP polyclonal antibody (1/2000) and HRP-conjugated anti-rabbit IgG antibody (1/5000). Samples derived from untransfected F11 cells were blotted on lane 1 of both panels. The left bar indicates molecular weights in Daltons.

Figure 9:
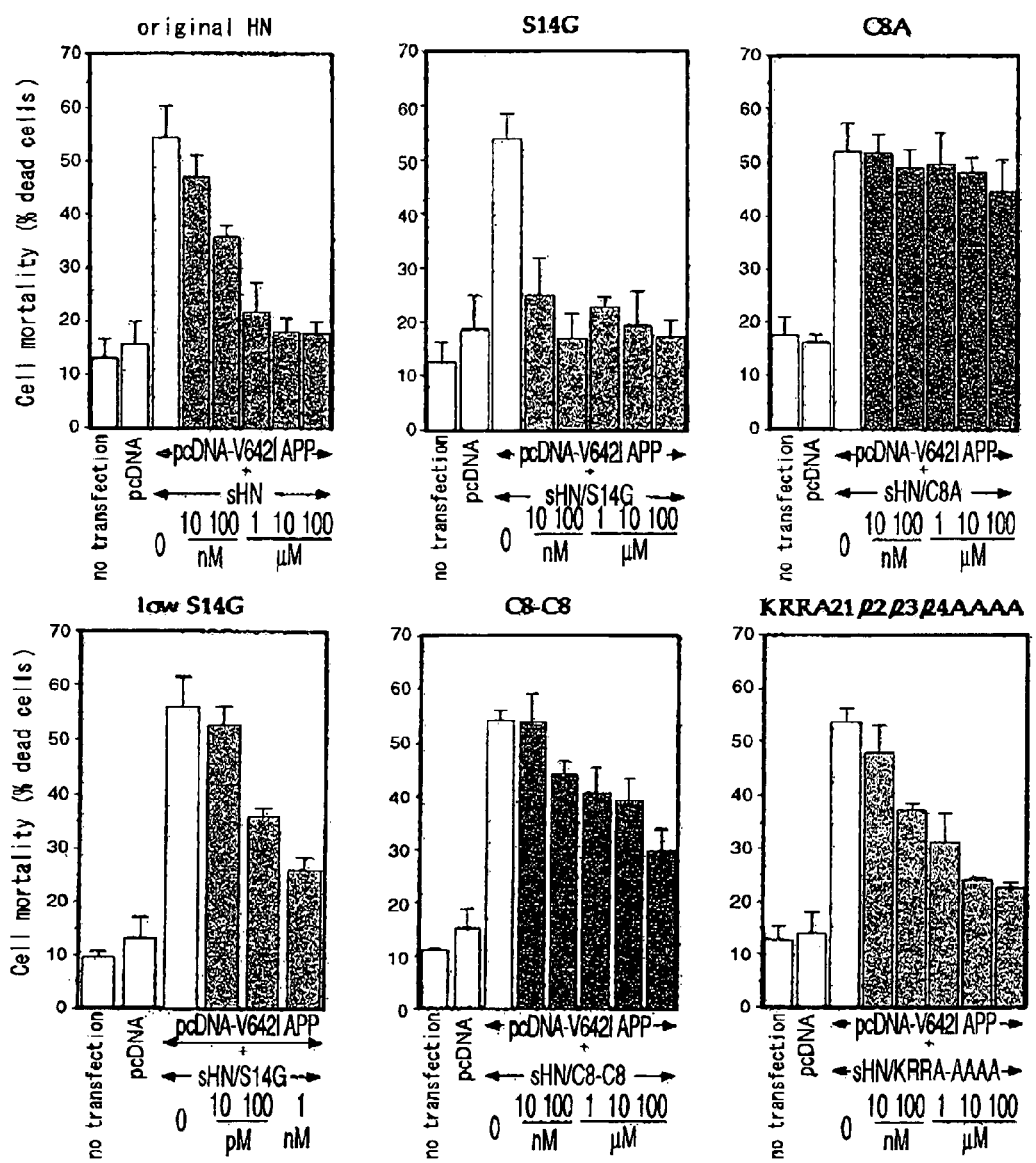

FIG. 9 depicts graphs demonstrating the effect of synthetic HN (sHN) and structural derivatives thereof on neuronal death induced by V642I APP. F11 cells were transfected with pcDNA encoding V642I APP; and were treated with various concentrations of sHN (Authentic HN) (SEQ ID NO: 5), sHNG (S14G) (SEQ ID NO: 8), sHNA (C8A) (SEQ ID NO: 9), dimer form of sHN through C8 (C8-C8), and sHN in which the C-terminal KRRA was replaced with AAAA (KRRA21/22/23/24AAAA) (SEQ ID NO: 10). 72 hours after the transfection, cell death was measured by trypan blue exclusion assay. Mean ±S.D. values of three independent experiments are indicated.

Figure 10:
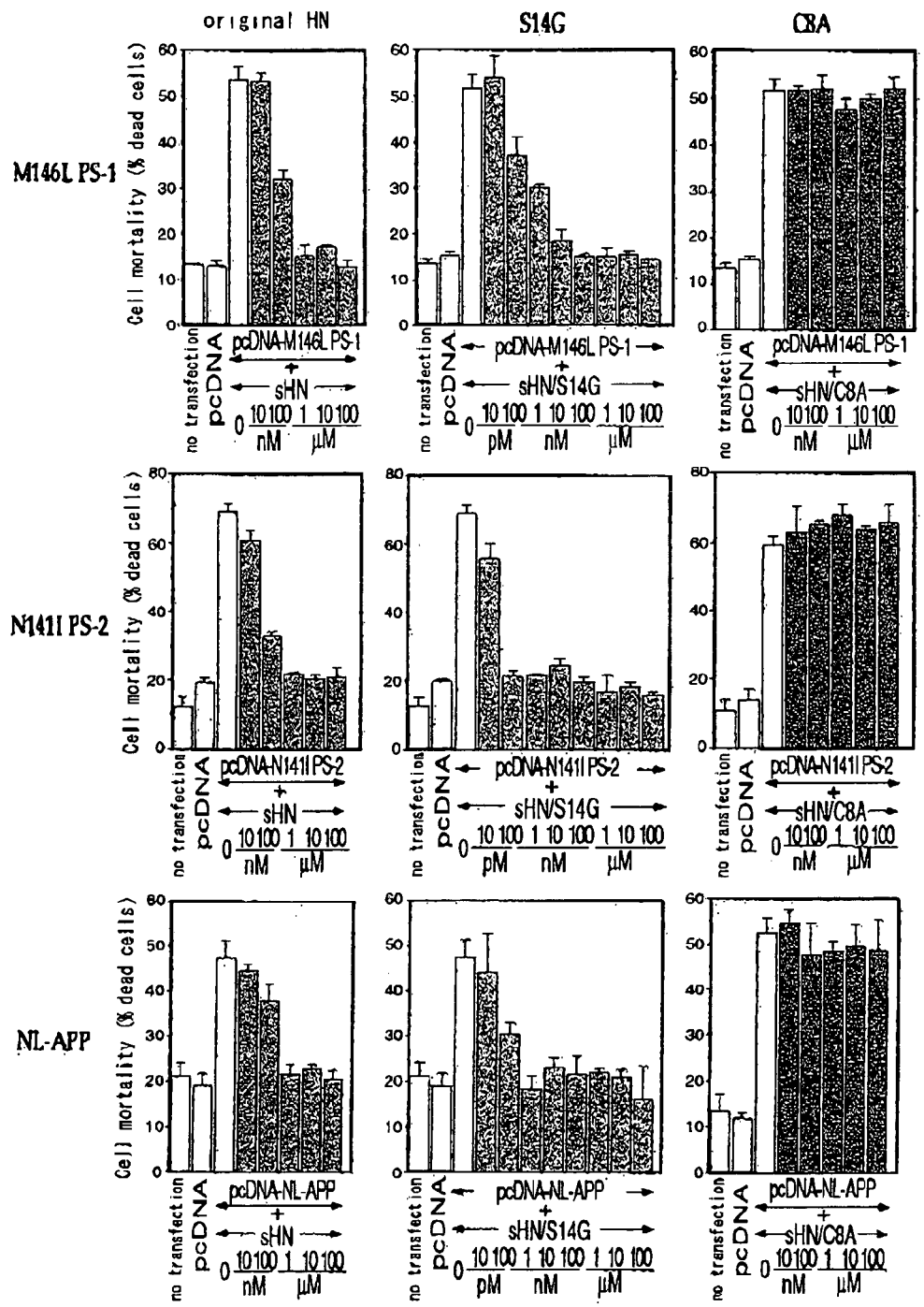

FIG. 10 depicts graphs demonstrating the effect of sHN, sHNG, or sHNA on neuronal death induced by M146L PS-1, N141I PS-2, or NL-APP. Similarly to FIG. 9, F11 cells were transfected with M146L PS-1, N141I PS-2, or NL-APP cDNA; and were treated with various concentrations of sHN (Authentic HN), sHNG (S14G), or sHNA (C8A). 72 hours after the transfection, cell death was measured by trypan blue exclusion assay. Mean ±S.D. values of three independent experiments are indicated.

Figure 11:
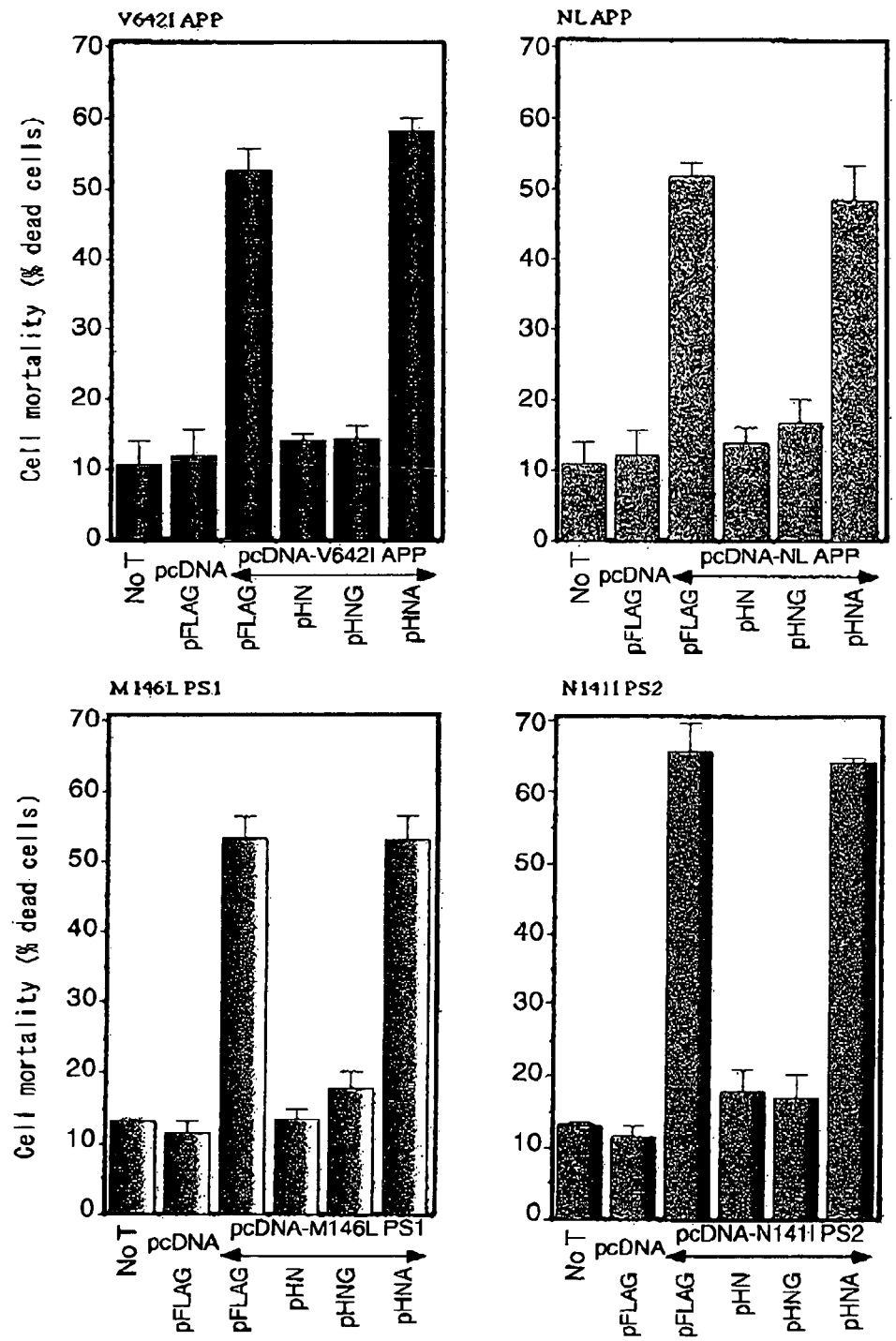

FIG. 11 depicts bar graphs demonstrating the effect of pHN, pHNG, or pHNA on neuronal death induced by the expression of FAD genes. F11 cells were transfected with empty vector (pcDNA) or pcDNA encoding V642I APP, NL-APP, M146L PS-1, or N141I PS-2, and pFLAG or pFLAG encoding HN (pHN, pHNG, or pHNA); and were cultured for 72 hours. Cell death was measured by trypan blue exclusion assay. Mean ±S.D. values of three independent experiments are indicated.

FIGS. 12A-12D depict graphs demonstrating the lack of effect of HN and structural derivatives thereof on neuronal death induced by polyglutamine repeat Q79. Mean ±S.D. values of three independent experiments are indicated in the graphs.

Figure 12A:
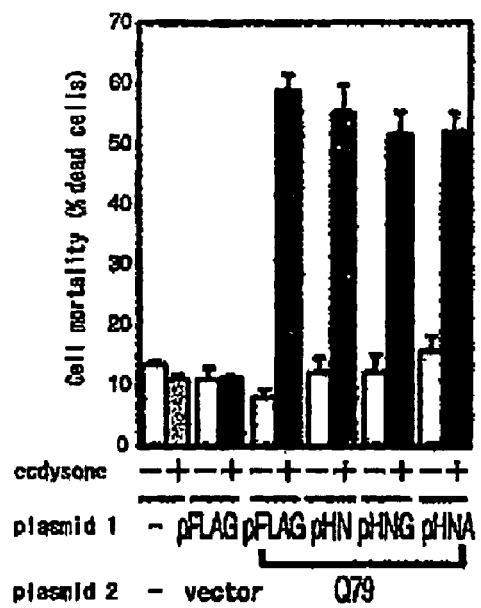

FIG. 12A demonstrates the lack of the effect of pHN, pHNG, or pHNA on neuronal death caused by the expression of Q79 induced by ecdysone. F11/EcR cells were transfected with ecdysone-inducible type Q79 expression plasmid, and empty vector (pFLAG), pHN, pHNG, or pHNA, and were cultured for 72 hours in the presence (+) or absence (-) of ecdysone. Cell death was measured by trypan blue exclusion assay.

Figure 12B:
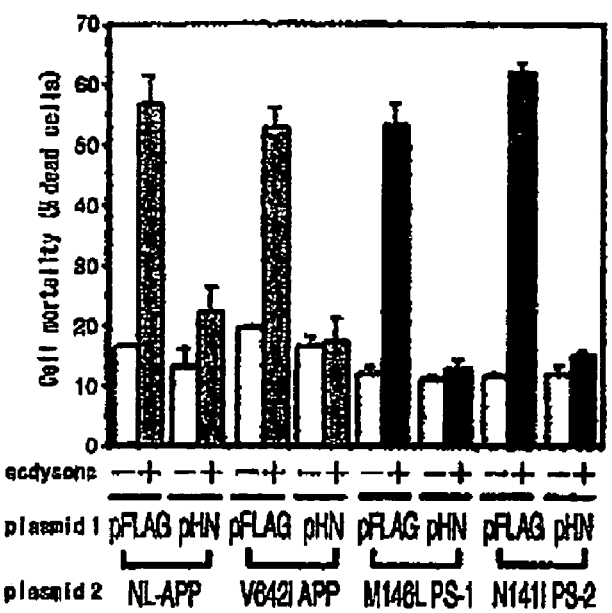

FIG. 12B demonstrates a significant suppressive effect by pHN co-transfection on neuronal death caused by ecdysone-induced expression of NL-APP, V642I APP, M146L PS-1, or N141I PS-2. Under the same conditions as in FIG. 12A, F11/EcR cells were transfected with ecdysone-inducible FAD gene plasmid, and pFLAG or pHN, and then, were cultured for 72 hours in the presence (+) or absence (-) of ecdysone. Cell death was measured by trypan blue exclusion assay.

Figure 12C:
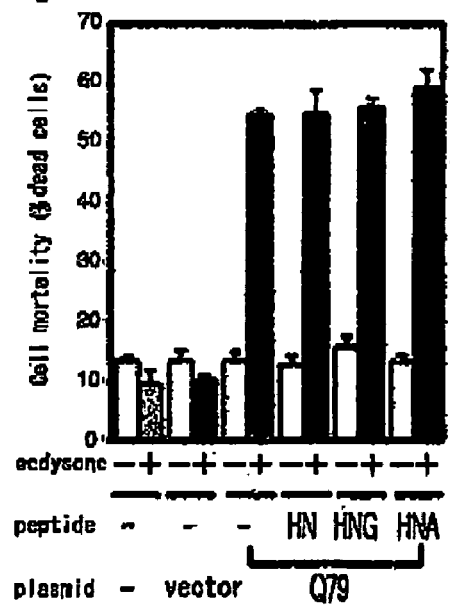

FIG. 12C demonstrates the lack of effects of sHN, sHNG, or sHNA on neuronal death induced by ecdysone-inducible expression of Q79. F11/EcR cells were transfected with ecdysone-inducible Q79 plasmids; treated with 1 μM sHN, sHNG, or sHNA; and then, were cultured in the presence (+) or absence (-) of ecdysone. 72 hours after the initiation of the exdysone treatment, cell death was measured by trypan blue exclusion assay.

Figure 12D:
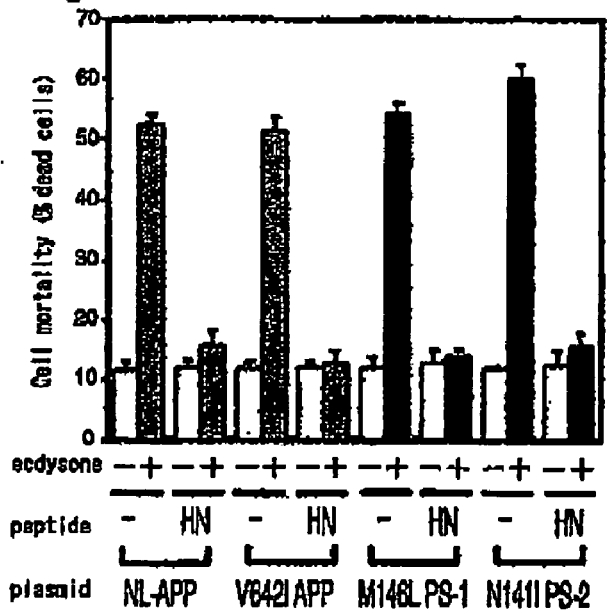

FIG. 12D demonstrates a significant suppressive effect by sHN on neuronal death caused by ecdysone-induced expression of NL-APP, V642I APP, M146L PS-1, or N141I PS-2. Under the same conditions as in FIG. 12C, F11/EcR cells were transfected with ecdysone-inducible FAD gene plasmid; treated with 1 μM sHN; and then, were cultured in the presence (+) or absence (-) of ecdysone. 72 hours after the initiation of the ecdysone treatment, cell death was measured by trypan blue exclusion assay.

Figure 13A:
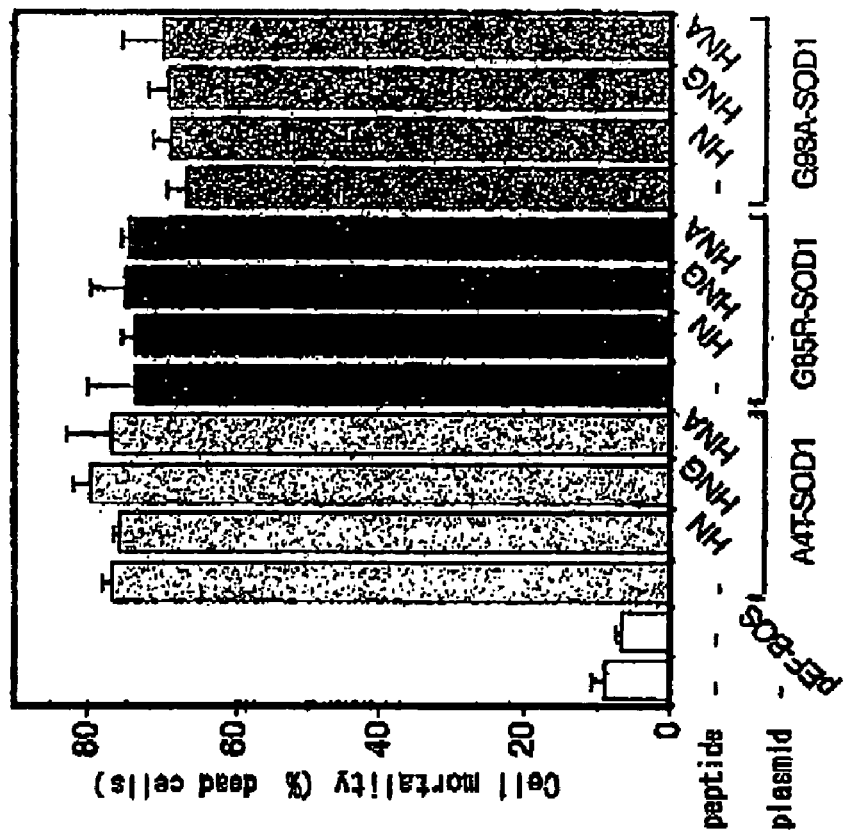
Figure 13B:
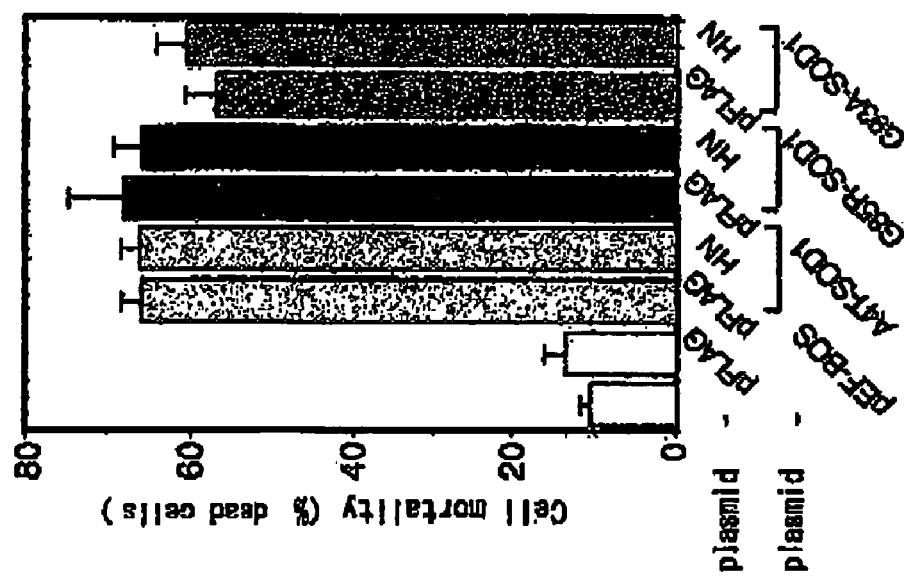

FIGS. 13A-13B depict graphs demonstrating the lack of the effect of HN and structural derivatives thereof on neuronal death induced by the ALS-associated SOD1 mutants. Mean ±S.D. values of three independent experiments are indicated in the graphs.

FIG. 13A demonstrates the lack of the effect of pHN co-transfection on neuronal death induced by the expression of the ALS-related SOD1 mutants. F11 cells were transfected with pEF-BOS encoding the ALS-associated mutant SOD1 (A4T, G85R, or G93A mutants' of SOD1) and empty vector (pFLAG) or pHN. Cell death was measured by trypan blue exclusion assay.

FIG. 13B demonstrates the lack of the effect of sHN, sHNG, or sHNA on neuronal death induced by the expression of the ALS-associated SOD1 mutants. F11 cells were transfected with pEF-BOS encoding A4T, G85R, or G93A SOD1, and were treated with 100 μM sHN, sHNG, or sHNA. Cell death was then measured by trypan blue exclusion assay.

Figure 14:
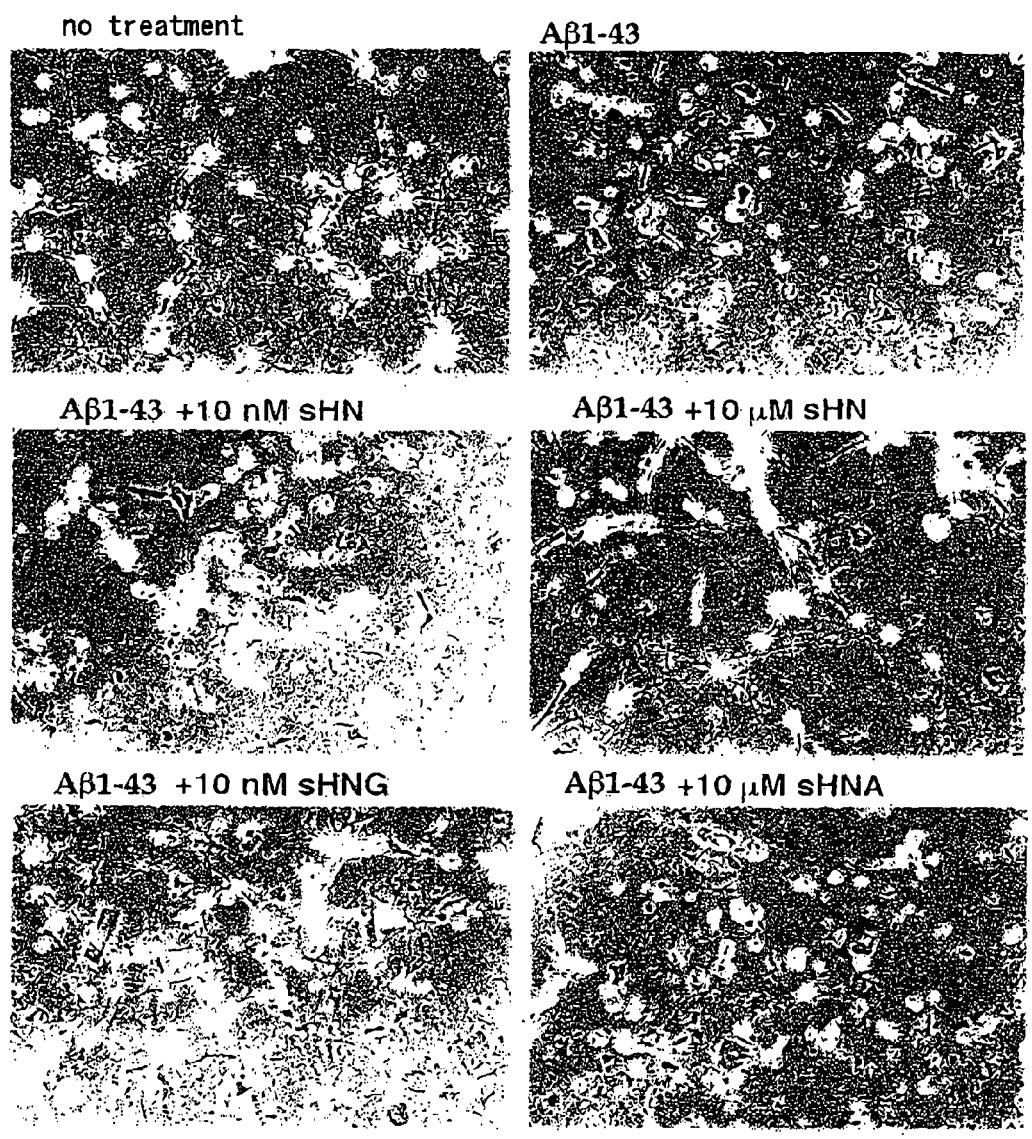

FIG. 14 depicts phase-contrast photomicrographs demonstrating the effect of HN on Aβ-induced cell death of primary cultured neurons. Representative photomicrographs are shown. Primary cultured cortical neurons were treated for 72 hours with 25 μM Aβ1-43 in the presence or absence of sHN (10 nM, 10 μM), 10 nM sHNG, or 10 μM sHNA. HN polypeptide was added 16 hours before the initiation of Aβ1-43 treatment so that the final concentrations of the polypeptides were those indicated in the figure. Addition of Aβ1-43 was performed by initially removing half of the media, and then supplementing with equal amounts of fresh media, containing 50 μM Aβ1-43 and sHN or sHNA at a concentration mentioned above. Untreated cells (no treatment), which were not treated with Aβ, were also observed. Similar experiments were performed at least 3 times, and reproducible results were obtained.

Figure 15:
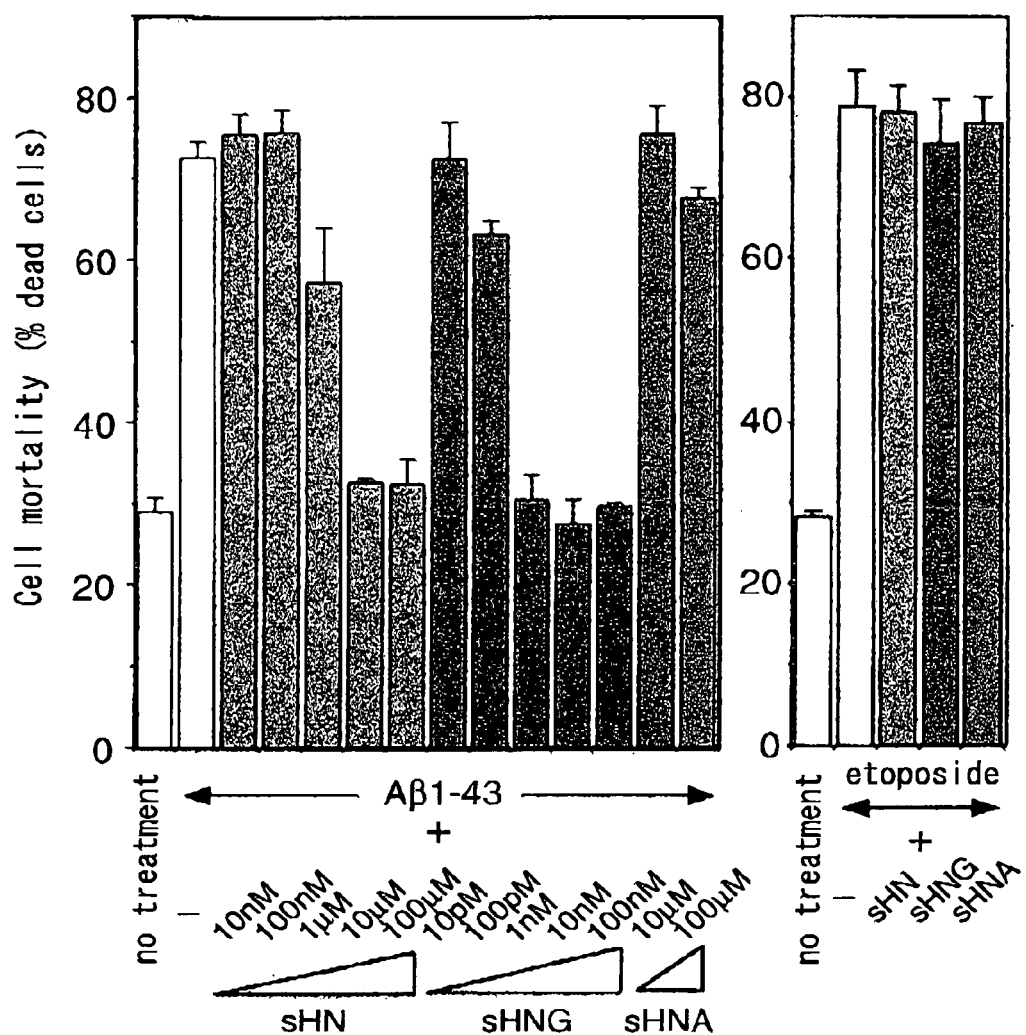

FIG. 15 depicts graphs demonstrating the effect of HN on Aβ-induced cell death of primary cultured neurons. 25 μM Aβ1-43 was added to primary cultured cortical neurons in the presence (at indicated concentrations) or absence of sHN, sHNG, or sHNA. Addition of HN polypeptides was performed similarly to that described in FIG. 14. 72 hours after the initiation of Aβ treatment, cell death was measured by trypan blue exclusion assay. Primary cultured neurons treated similarly for 72 hours with 20 μM etoposide in the presence or absence of 10 μM sHN or HN derivatives were used as the positive controls in these experiments. Similar experiments were performed at least three times, and reproducible results were obtained. Mean ±S.D. values of three independent experiments are indicated in the graphs.

Figure 16:
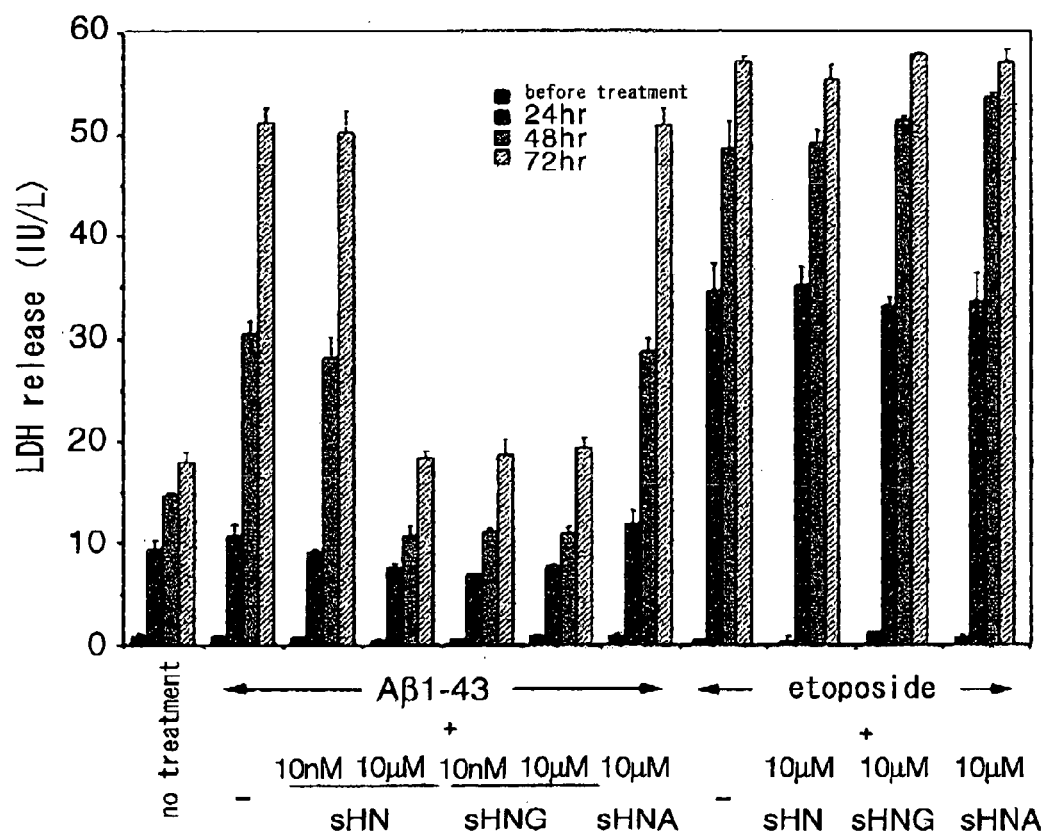

FIG. 16 depicts a graph demonstrating the effect of HN on Aβ-induced cell death of primary cultured neurons. Cell damage was monitored as the amount of LDH released into the culture media. 25 μM Aβ1-43 was added to primary cultured cortical neurons in the presence (at indicated concentrations) or absence of sHN, sHNG, or sHNA. Addition of HN polypeptides was performed similarly to that described in FIG. 14. 24, 48, or 72 hours after the initiation of Aβ treatment, the amount of LDH in the culture media was measured. LDH release from neurons treated with 20 μM etoposide in the presence or absence of HN polypeptides was also measured. Similar experiments were performed at least three times, and reproducible results were obtained. Mean ±S.D. values of three independent experiments are indicated in the graph.

Figure 17:
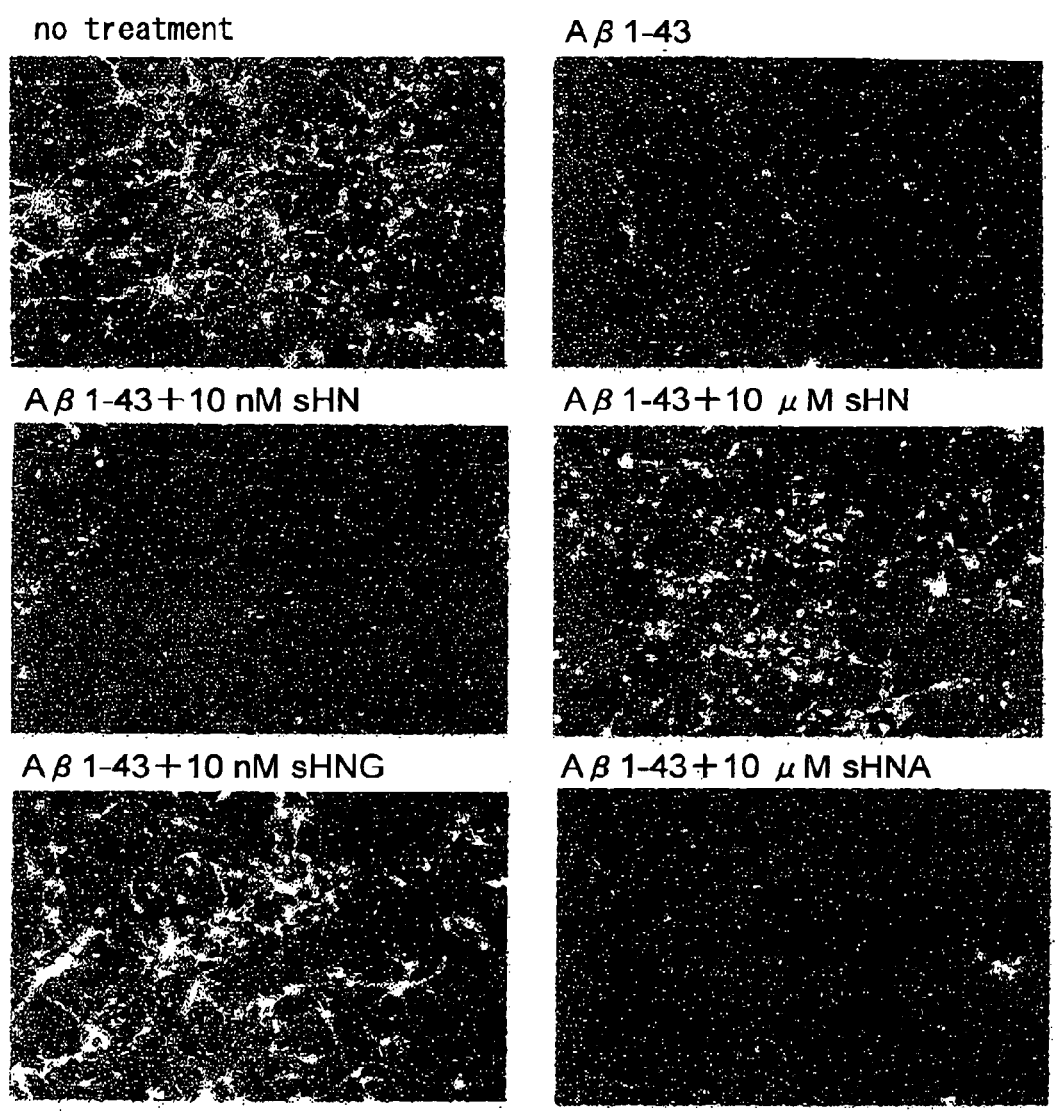

FIG. 17 depicts photographs demonstrating the effect of HN on Aβ1-43-induced cell death of primary cultured neurons. The result of Calcein-AM staining is demonstrated as fluorescence photomicrographs. 25 μM Aβ1-43 was added to primary cultured cortical neurons in the presence (at indicated final concentrations) or absence of HN polypeptides. Addition of HN polypeptides was performed similarly to that described in FIG. 14. 72 hours after Aβ1-43 treatment, calcein-AM staining was performed. Untreated cells (no treatment), that were not treated with Aβ, were also observed. Cytoplasmic fluorescence indicates cell viability. Similar experiments were performed at least three times, and reproducible results were obtained. Representative results are demonstrated in the figure.

Figure 18:
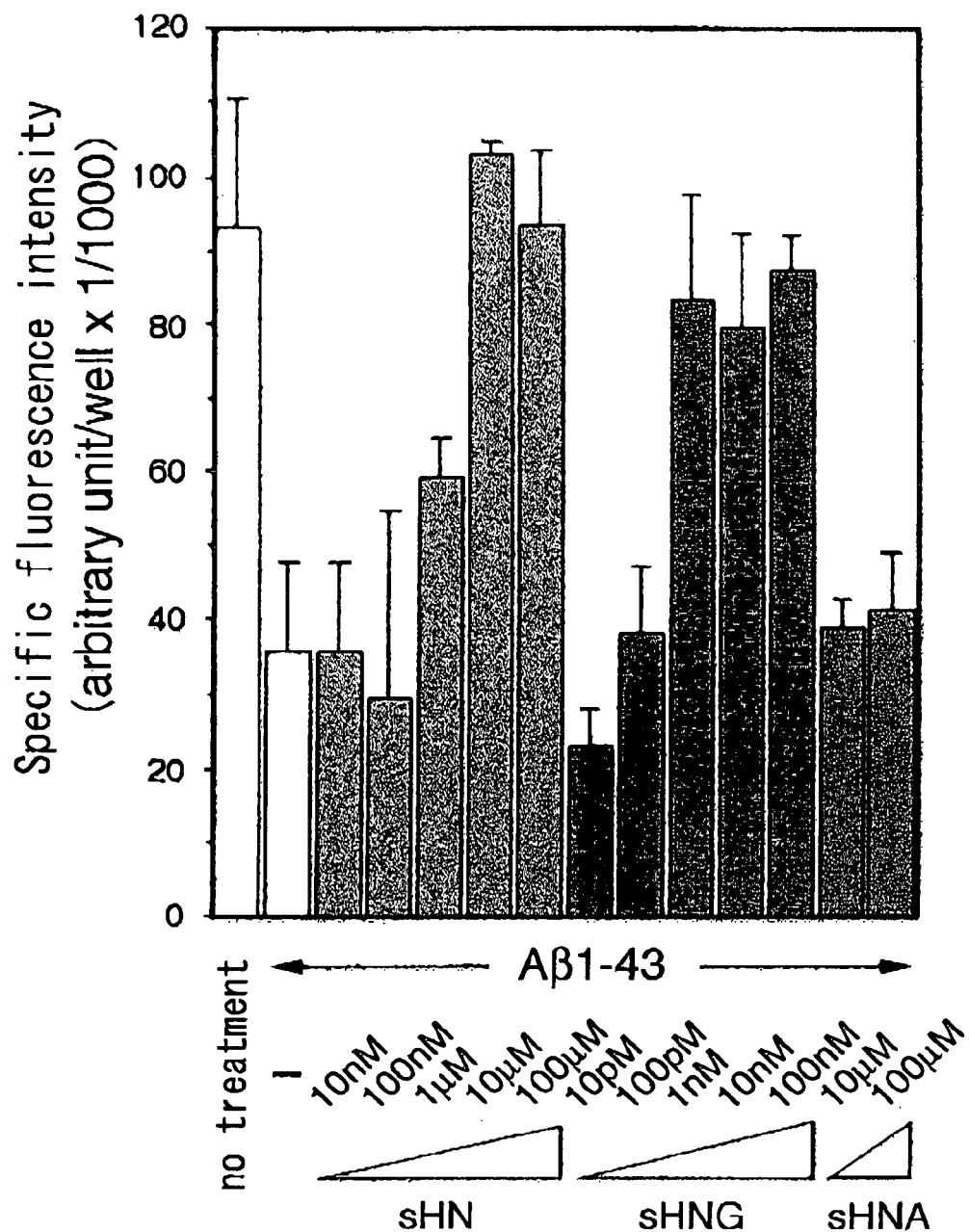

FIG. 18 depicts a graph demonstrating the result of fluorescence measurements of Calcein-AM staining. 25 μM Aβ1-43 was added to primary cultured cortical neurons in the presence (at indicated final concentrations) or absence of HN polypeptides. Addition of HN polypeptides was performed similarly to that described in FIG. 14. Calcein-AM staining was performed after 72 hours from the Aβ1-43 treatment, and fluorescence intensity of each well was measured. The basal fluorescence intensity was calculated as 36960 (unit/well), and this was substracted from the values measured for each well. Similar experiments were performed at least three times, and reproducible results were obtained. Mean ±S.D. values of three independent experiments are indicated in the graph.

FIGS. 19A-19D depict photographs demonstrating the expression of HN mRNA in various human tissues. Radiolabeled antisense HN (panel a), 19 mer encoding the 5' region (panel b), or DT77 (panel C) was hybridized as a probe to the sheet blotted with human tissue polyA-RNA (lane 1: brain; lane 2: heart; lane 3: skeletal muscles; lane 4: large intestine; lane 5: thymus; lane 6: spleen; lane 7: kidney; lane 8: liver; lane 9: small intestine; lane 10: pancreas; lane 11: lung; lane 12: peripheral leukocytes). The result of Northern blotting on the same sheet using β-actin as the probe is shown in panel d. The numbers on the left indicate molecular sizes. Similar experiments were performed at least three times, and similar results were obtained.

Figure 20:
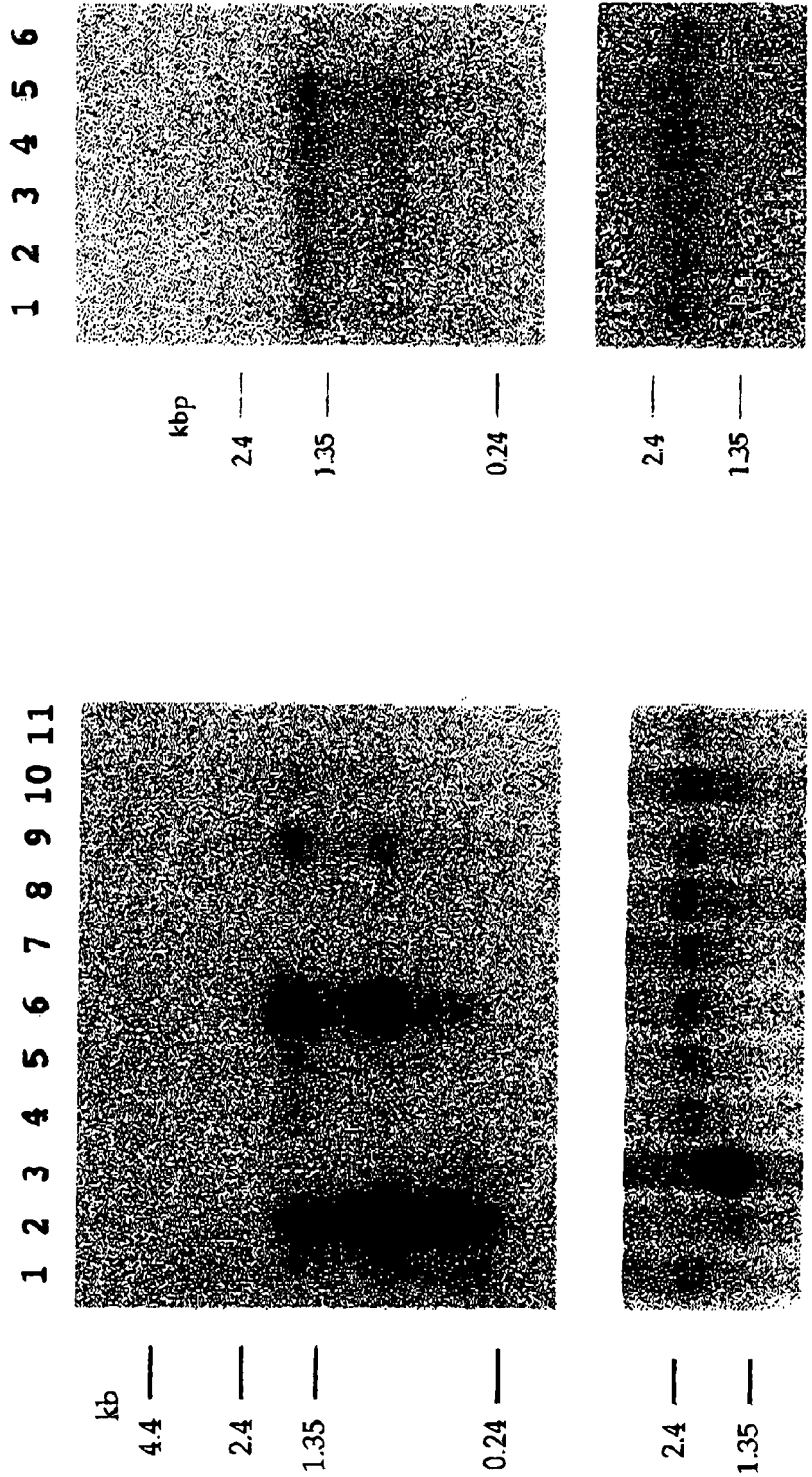

FIG. 20 depicts photographs demonstrating the expression of HN mRNA in mouse issues. PolyA-RNA (2 μg/lane) extracted from various mouse organs was submitted to 1.2% agarose gel electrophoresis, and after blotting, hybridization was performed using labeled antisense HN (top left) or β-actin (lower left) as probes (lane 1: brain; lane 2: heart; lane 3: skeletal muscles; lane 4: thymus; lane 5: spleen; lane 6: kidney; lane 7: liver; lane 8: small intestine; lane 9: stomach; lane 10: skin; lane 11: lung).

The right panel demonstrates the HN mRNA expression region in mouse brain. Labeled antisense HN (top panel on the right) or β-actin probe (lower panel on the right) were hybridized to the sheet blotted with polyA-RNA derived from various regions of the mouse brain (lane 1: frontal lobe; lane 2: temporal lobe; lane 3: parietal lobe; lane 4: occipital lobe; lane 5: cerebellum; lane 6: lung). For quantitative comparison among the sheets, the same amount of lung-derived polyA-RNA as in the left panel was electrophoresed in lane 6 for the hybridization.

FIG. 21 depicts bar graphs demonstrating the result of a detailed analysis of the structure/function relationship regarding the protective activity of HN. The effect of HN-truncated derivatives on V642I APP-induced neuronal death is demonstrated. As indicated in FIG. 9, F11 cells were transfected with V642I APP cDNA in the presence or absence of each of the synthetic HN derivatives; and 72 hours later, cell death was measured by trypan blue exclusion assay. The top panel on the left demonstrates the result of examination on the N-terminus truncated HNs (SEQ ID NOS: 5, and 12-19), which sequences are indicated in the panel below. The top panel on the right demonstrates the result of examination on the C-terminus truncated polypeptides of ΔN2 HN (SEQ ID NOS: 20-23), which sequences are indicated in the panel below. Mean ±S.D. values of three independent experiments are indicated. The results obtained in the experiments indicated in the panel are summarized in the lower panel.

Figure 22:
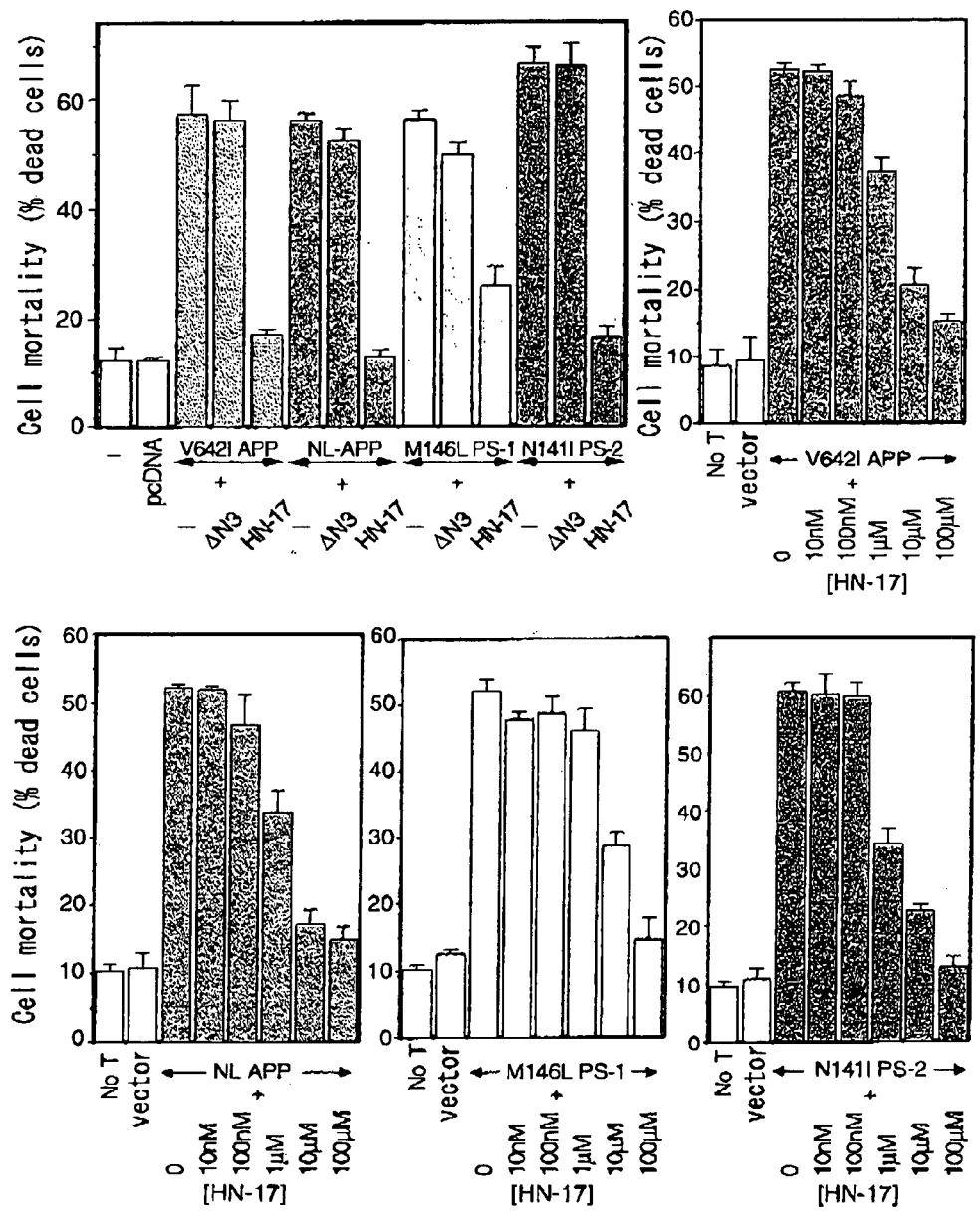

FIG. 22 depicts bar graphs demonstrating the effect of ΔN3HN and HN-17 on neuronal death induced by four different types of FAD genes. F11 cells were transfected with V642I APP, NL-APP, M146L PS-1 or N141I PS-2 cDNA in the presence or absence of 10 μM ΔN3 HN or HN-17; and 72 hours later, cell death was measured by trypan blue exclusion assay (top left panel). The top panel on the right and lower panels indicate dosage-response curves of the effect of HN-17 on neuronal death suppression by the FAD genes. F11 cells were transfected with respective FAD gene (V642I APP, NL-APP, M146L PS-1, or N141I PS-2 cDNA) in a similar manner in the absence or presence of gradually increasing concentrations as shown in the figure of synthetic HN-17. 72 hours later, cell death was measured by trypan blue exclusion assay. The result of cells untransfected with FAD genes is indicated as "no Tx". Mean ±S.D. values of three independent experiments are indicated in the graphs.

Figure 23:
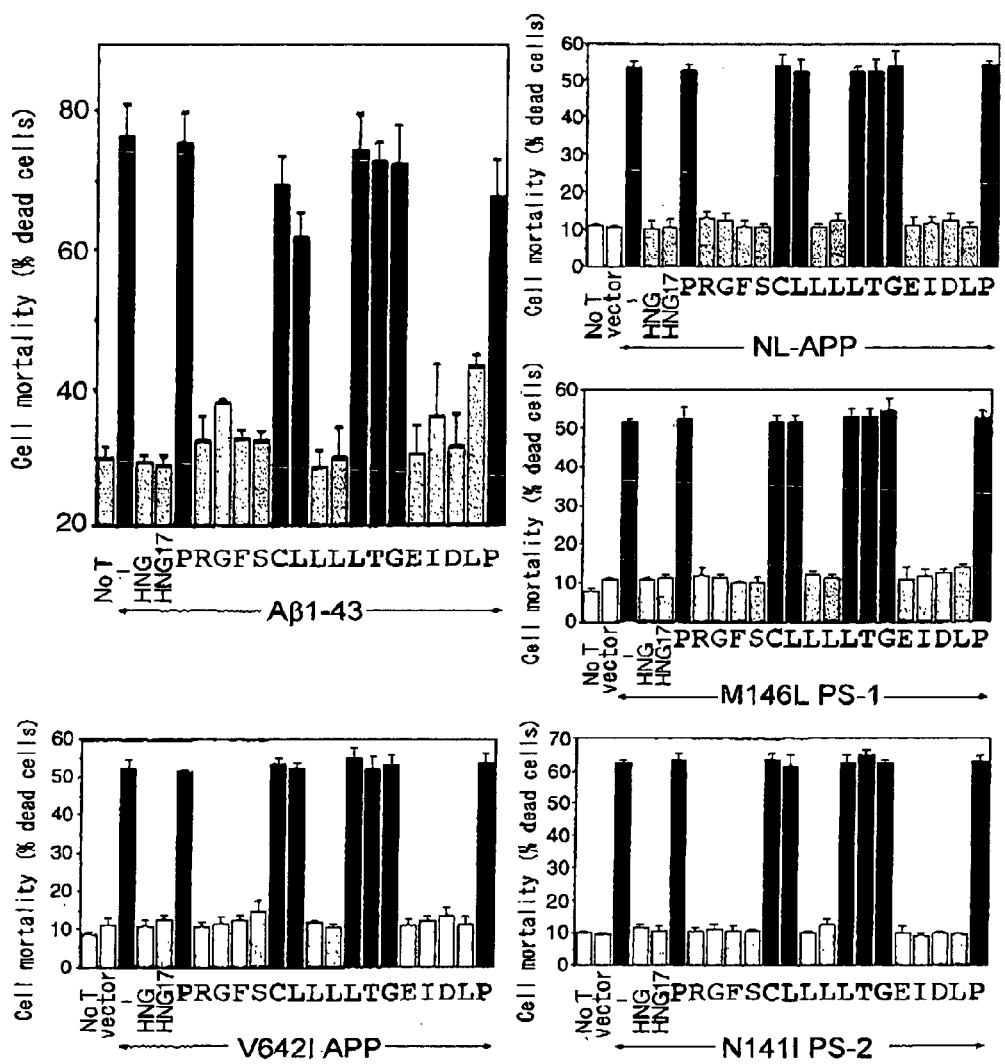

FIG. 23 depicts bar graphs demonstrating the effect of Ala-substituted (Ala-scanned) HNG-17 (SEQ ID NO: 24) on neuronal death caused by four different types of FAD genes and Aβ1-43. Primary cultured neurons were treated with 25 μM Aβ1-43 (top panel on the left), or F11 cells were transfected with V642I APP, NL-APP, M146L PS-1 or N141I PS-2 cDNA (other panels) in the presence or absence of 10 nM Ala-substituted HNG-17; and 72 hours later, cell death was measured by trypan blue exclusion assay. Cell death antagonizing effect of each Ala-substituted HNG-17 was determined. Substituted residues are indicated at the bottom of the graphs. Amino acid sequences of each Ala-substituted form are indicated in order from SEQ ID NO: 25 to 41. For example, in the top panel on the left, the primary cultured neurons incubated for 72 hours with 25 μM Aβ1-43 in the presence of 10 nM ARGFSCLLLLTGEIDLP (the underlined A is substituted from P) (SEQ ID NO: 25) showed a cell mortality of 75.3±4.4% (mean ±S.D. of three independent experiments), which was comparable to the cell mortality of neurons incubated with Aβ1-43 (76.1±4.7%).

When neurons were incubated with 25 µM Aβ1-43 in the presence of 10 nM HNG or HNG-17, cell mortality was 29.3±0.9% or 28.8±2.3% respectively, which was comparable to the basal cell mortality (30.0±1.6%). The results indicated as "no T" are results of cells untransfected with FAD genes; "vec" of cells transfected with an empty vector; and "no" of cells untreated with polypeptides. Mean ±S.D. values of three independent experiments are indicated in the graphs.

Figure 24:
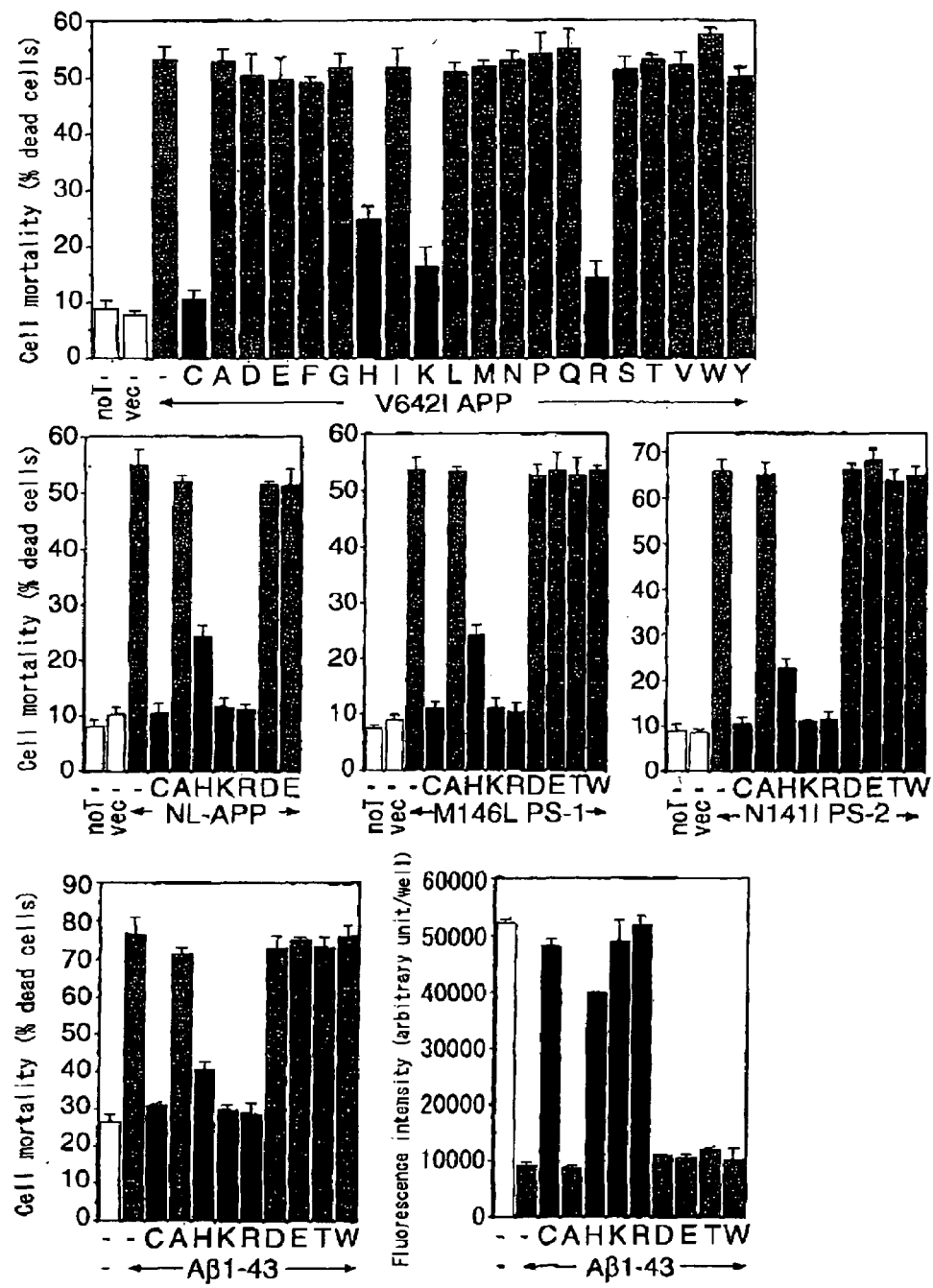
Figure 25A:
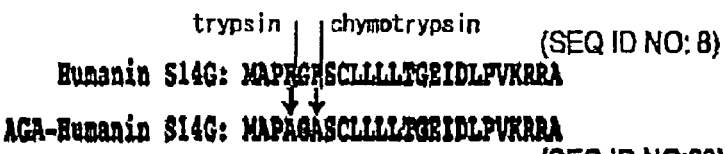
Figure 25B:
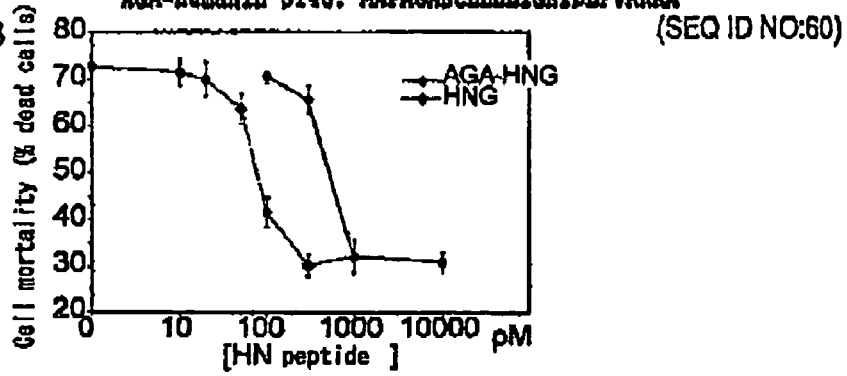
Figure 25C:
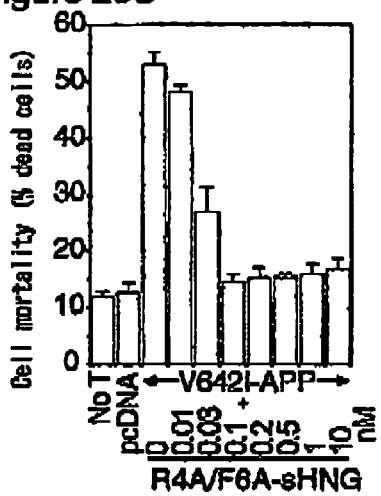
Figure 25D:
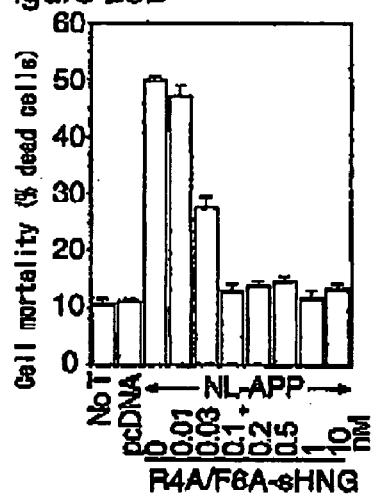
Figure 25E:
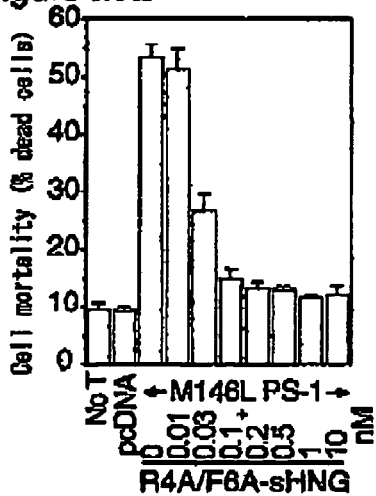
Figure 25F:
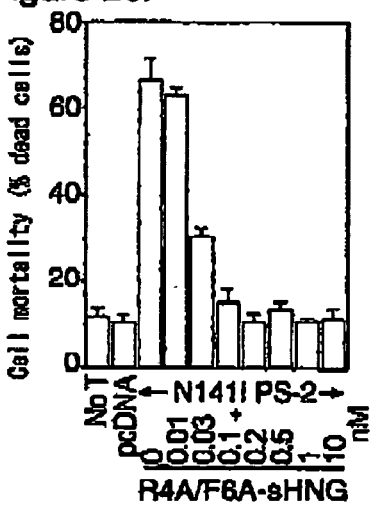

FIG. 24 depicts bar graphs demonstrating the effect of mutated HNG polypeptides, wherein Cys at position 8 of HNG is substituted with other amino acids, to suppress cell death.

Top panel: F11 cells in their original form, or F11 cells transfected with V642I-APP cDNA (1 µg) were treated with any one of the mutated HNG polypeptides (10 nM) wherein C8 is substituted with any one of the 19 possible amino acid residues (indicated by a one-letter code in the figure). 72 hours after the initiation of the transfection, cell mortality was measured by trypan blue exclusion assay. The results of no polypeptide treatment are indicated as "no T"; and "vec" for transfection with an empty pcDNA vector. "C" indicates the original HNG (SEQ ID NO: 8). "A" is HNA (SEQ ID NO: 9). The amino acid sequences of polypeptides "D" to "Y" are indicated in order from SEQ ID NO: 42 to 59. Cell mortality is indicated as mean ±S.D. values of three independent experiments. The proportion of dead cells among all cells (% dead cells) is indicated.

Center panels: F11 cells in their original form, or F11 cells transfected with 1 µg of FAD genes (left panel: K595N/M596L-APP; center panel: M146L-PS-1; right panel: N141I-PS-2) were treated with any one of the mutated HNG polypeptides (10 nM) wherein C8 is substituted with the indicated amino acid residue. 72 hours after the initiation of the transfection, cell mortality was measured by trypan blue exclusion assay. The results of no polypeptide treatment are indicated as "no T"; and "vec" for transfection with an empty pcDNA vector. The values are indicated as mean ±S.D. values of three independent experiments.

Lower panel: Primary cultured cortical neurons were treated with 25 µM Aβ1-43 in the presence of any one of the mutated HNG polypeptides (10 nM) wherein C8 is substituted with the indicated amino acid residue. Cell mortality was measured by trypan blue exclusion assay 72 hours after the initiation of the Aβ treatment (left panel); and cell viability assay was performed by Calcein staining (right panel). The values are indicated as mean ±S.D. values of three independent experiments.

FIGS. 25A-25F depict graphs demonstrating the effect of AGA-HNG (SEQ ID NO: 60) on neuronal death induced by the four different types of FAD genes and Aβ1-43. Priamry cultured neurons were treated with 25 µM Aβ1-43 in the absence or presence at various concentrations of AGA-HNG (panel B), or F11 cells were transfected with V642I APP, NL-APP, M146L PS-1, or N141I PS-2 cDNA (panels C to F); and 72 hours later, cell death was measured by trypan blue exclusion assay. In the primary cultured neuron experiment using Aβ, various concentrations of HNG were used to perform similar experiments as controls. The result of untransfected cells is indicated as "no T"; and the result of cells transfected with the empty vector as "pcDNA". Mean: ±S.D. values of three independent experiments are indicated in the graphs.

BEST MODE FOR CARRYING OUT THE INVENTION

The present invention will be described in detail using Examples below, but the invention is not to be construed as being limited to these Examples. The experimental procedures described in these Examples are as follows:

V642I APP cDNA has been described previously (Yamatsuji, T. et al. (1996) Science 272, 1349-1352). The M146L mutant of PS-1 cDNA and the N141I mutant of PS-2 cDNA were gifts from Dr. Peter St. George-Hyslop (Sherrington, R. et al. (1995) Nature 375, 754-760) and Dr. Luciano D'Admio (Wolozin, B. et al. (1996) Science 274, 1710-1713), respectively. All of the FAD genes used in the Examples were encoded in pcDNA vectors (Funk, C. D. et al. (1990) Proc. Natl. Acad. Sci. USA, 87:5638-5642). The ALS-associated mutant of SOD1 cDNA (A4T, G85R, G93A) (Takahashi, H. et al. (1994) Acta Neuropathol. 88, 185-8), and pDN-E/G5H-Q79 were gifts from Dr. Shoji Tsuji, (Niigata University School of Medicine, Niigata, Japan), and Dr. Akira Kakizuka (Osaka Biomedical Research Center, Osaka, Japan), respectively.

The pHN plasmids encoding Humanin were constructed by inserting HN cDNAs into the polycloning site of pFLAG-CMV-5a vectors (pFLAG) (Eastman Kodak). More specifically, pFLAG-CMV-5a plasmids were digested with EcoRI and KpnI, and the HN-encoding sense oligonucleotide (5'-AATTCACCATGGCTCCACGAGGGT-TCAGCTGTCTCTTACTTTTAACCAGTGAAATTGACC TGCCCGTGAAGAGGCGGGCAGGTAC-3'/SEQ ID NO: 1) and antisense oligonucleotide (5'-CTGCCCGCCTCT-TCACGGGCAGGTCAATTTCACTGGT-TAAAAGTAAGAGACAGCTGAACC CTCGTGGAGC-CATGGTG-3'/SEQ ID NO: 2) were ligated. The plasmid expresses Humanin polypeptide fused with FLAG tag (DYKDDDDK) to the C-terminus.

The pFLAG plasmids (pHNG and pHNA), encoding mutant HN, were constructed from pHN using Quick Change Site-directed Mutagenesis Kit (Stratagene). The sequence was confirmed by direct sequencing. To construct the HN-EGFP plasmid, first HN-encoding sense and antisense oligonucleotides were phosphorylated; and after annealing at 95° C. for 3 minutes, the oligonucleotide was subcloned into the EcoRI-KpnI site of pEGFP-N3 vector (Clotech laboratories) using T4 DNA ligase. Synthetic HN polypeptides (sHN) and structurally modified synthetic polypeptides purified to 95% or higher purity were used. Synthetic HN (sHN) and several other synthetic HN-derived polypeptides were obtained from two independent sources, to obtain essentially the same results. Anti-FLAG antibody was purchased from Eastman Kodak (M2 monoclonal antibody, Cat. #IB13010). Aβ1-43 was purchased from BACHEM (Cat. #H-1586). Other reagents were all commercially available.

The expression cDNA library encoded in pEF-BOS was constructed from poly(A) $^+$RNA extracted from brain sample (occipital cortex) of a patient with sporadic AD, confirmed by biopsy according to institute guidelines. The poly(A) $^+$RNA was reversely transcribed using a modified oligo-dT primer containing a NotI site. Double-stranded cDNA was ligated with EcorRI-BstXI adapter primers (5'-pGAA TTC ACC ACA-3' and 3'-CTT AAG GTGp-5'), and was cleaved with NotI. After removing low molecular weight DNAs, the cDNA was ligated with BstXI-NotI fragment of pEF-BOS, and was transformed into XL1 Blue MRF' strain by electroporation. The primary library size and the mean insert size were $3.2\times10^6$ cfu/16 ml and 0.9 kb, respectively.

F11 cells (Platika, D. et al. (1985) Proc. Natl. Acad. Sci. U.S.A. 82, 3499-3503; Yamatsuji, T. et al. (1996) Science 272, 1349-1352) were cultured in HamF-12 media containing 18% fetal bovine serum (FBS) and antibiotics. $7\times10^4$/well of F11 cells were seeded into a 6-well plate; cultured in HamF-12 containing 18% FBS for 12 to 16 hours; transfected 3 hours with plasmids encoding FAD genes and plasmids encoding HN (pHN, and such) by lipofection in the absence of serum (1 µg of FAD cDNA expression plasmid, 1 µg of HN cDNA expression plasmid, 4 µl of LipofectAMINE, 8 µl of Plus reagent); and then, were cultured for 2 hours in HamF-12 media containing 18% FBS. Then, culture media were exchanged with HamF-12 media containing 10% FBS; and the cells were cultured for additional 67 hours. 72 hours after transfection, cell death was measured by trypan blue exclusion assay. Experiments using synthetic HN polypeptides were conducted as follows: F11 cells (at $7\times10^4$/well in a 6-well plate) were transfected 3 hours with FAD genes in the absence of serum, as mentioned above; after cultivation for 2 hours in HamF-12 media containing 18% FBS, the cells were cultured for 67 hours in HamF-12 media containing 10% FBS with various concentrations of HN polypeptides; and cell death was measured by trypan blue exclusion assay. ALS-associated mutant cDNAs of SOD1 were also similarly transfected, and examined for their neurotoxicity.

To obtain the culture supernatant of F11 cells transfected with pHN (CM/F11-pHN), F11 cells were transfected with pHN in the absence of serum by lipofection for 3 hours (1 µg of pHN, 2 µl of LipofectAMINE, 4 µl of Plus reagent); and were cultured for 2 hours in HamF-12 media containing 18% FBS. Thereafter, the media was exchanged with HamF-12 media containing 10% FBS; and the cells were additionally cultured for 67 hours. CM/F11-pHN was obtained by freeze-thawing the culture media once. CM/F11-vec was similarly prepared from pFLAG-transfected F11 cells. For immunoblot analysis of CM/F11-pHN, CM/F11-pHNG, and CM/F11-pHNA, protease inhibitor cocktail (Boehringer Mannheim, Cat. #1697498; one tablet was dissolved in 2 ml of distilled water, and a volume 1/25 to that of the sample was added to the sample) was added to the culture media that had not been freeze-thawed. For immunoblot analysis using cell lysates, the cells were washed twice with PBS, and were suspended in 30 µl of homogenizing buffer [10 mM tris/HCl (pH7.5), 1 mM EDTA, 1% Triton X-100, and 1 tablet/50 ml of protease inhibitor cocktail]. After two freeze-thawing cycles, the cell homogenate was centrifuged at 15,000 rpm for 10 minutes at 4° C., and the supernatant was submitted to immunoblot analysis with Tris/Tricine gel electrophoresis. Tris/Tricine gel electrophoresis was performed according to the litearture (Schagger, H. and von Jagow, G. (1987) Analytical Biochemistry 166, 168-179).

F11/EcR/V642I cells were established using ecdysone-inducible V642I APP expression plasmid. First, the co-expression vector pVgRXR was transfected into F11 cells (Invitrogen) and cells were subjected to Zeocin selection to establish F11 cells (F11/EcR cells) that stably overexpress both ecdysone receptor EcR and the retinoid X receptor RXR. V642I APP cDNA was inserted into pIND vector (Invitrogen), having multiple copies of ecdysone responsive sequences; and after transfection of the vector into F11/EcR cells, G418 selection was performed. F11/EcR/V642I cells were cloned by limiting dilution. F11/EcR/V642I cells were cultured in HamF-12 media containing 18% FBS and antibiotics. Before ecdysone treatment, the cells were cultured for 24 hours in the presence of 10% FBS. Then, ecdysone (40 µM Ponasteron; Invitrogen Cat. #H101-01) was added to the cell culture media in the presence of 10% FBS. Cell death occurred to each F11/EcR/V642I cell, in response to ecdysone treatment; and the cell mortality 72 hours after treatment in all cells was 60 to 70%, which reached 80 to 90% after 96 hours from the treatment. A more detailed analysis of F11/EcR/V642I cells is described elsewhere (see International Application No. WO 00/14204).

F11/EcR cell experiment using ecdysone was conducted as follows: F11/EcR cells were seeded at $7\times10^4$/well into a 6-well plate; cultured for 12 to 16 hours in HamF-12 media containing 18% FBS; and were similarly transfected in the absence of serum for 3 hours with 1 µg of ecdysone-inducible plasmid alone, or with 1 µg of HN-encoding plasmid, as mentioned above. After culturing for 12 to 16 hours in HamF-12 media containing 18% FBS, the cells were cultured for 2 hours in HamF-12 media containing 10% FBS, then ecdysone (Ponasterone) was added to the media (final concentration of 40 µM). Cell death was measured 72 hours after ecdysone treatment. Experiments using synthetic HN polypeptides were conducted as follows: cells were similarly transfected for 3 hours with FAD genes in the absence of serum; cultured for 12 to 16 hours in HamF-12 media containing 18% FBS; cultured for 2 hours in HamF-12 media containing 10% FBS and various concentrations of HN polypeptide; and then, 40 µM Ponasterone was added to the media. Cell death was measured by trypan blue exclusion assay after 72 hours from the ecdysone treatment. HD/SCA-associated Q79 cDNAs were also similarly transfected, and the neurotoxicity was tested.

Primary culture of mouse cortical neurons was performed in poly-D-lysine-coated 24-well plates (Sumitomo Bakelite) in the absence of serum and in the presence of N2 supplement, as described in literature (Ecksioglu, Y. Z. et al. (1994) Brain Res. 644, 282-90). The purity of neurons prepared according to the method was >98%. The prepared neurons ($1.25\times10^5$/well, 250 µl media/well) were preincubated in the absence or presence of 10 nM or 10 µM sHN polypeptides for 16 hours; and were treated with 25 µM Aβ1-43 in the absence or presence of sHN polypeptides at the same concentrations for 24 to 72 hours. Since primary cultured neurons are damaged even by temporary dryness during medium exchange, treatment of the cells by Aβ1-43 was performed as follows. First, half of the volume of the old medium (125 µl) was discarded. Then, 125 µl of pre-warmed fresh medium containing 50 µM Aβ1-43 and sHN with a concentration indicated above were added to the culture.

Trypan blue exclusion assay was performed as follows. Without prewashing, the cells were suspended with gentle pipetting into a serum-free media. 50 µl of 0.4% trypan blue solution (Sigma, Cat. #T-8154) were added (final concentration of 0.08%) to 200 µl cell suspension, and the suspension was mixed at room temperature. Within 3 minutes of the trypan blue solution addition, stained cells were counted. Cell mortality was determined [100-cell survival rate (%)] based on the stained cell count. LDH assay was performed using a kit (LDH-Cytotoxic Test; Wako Pure Chemical Industries, Cat. #299-50601) by sampling 6 µl of media in which neurons were cultured. Calcein staining was performed as described in literature (Bozyczko-Coyne, D. et al. (1993) Journal of Neuroscience Methods 50, 205-216). Specifically, 6 µM Calcein-AM (3', 6'-Di-(O-acetyl)-2'-7'-bis[N,N-bis(carboxymethyl)aminomethyl]fluorescein, tetraacetoxymethyl ester; Dojindo, Cat. #349-07201) was added to the neurons; and 30 minutes or longer after Calcein-AM treatment, fluorescence (ex=490 nm, em=515 nm) was observed by fluorescence microscopy, and measured by a spectrometer. Specific fluorescence was calculated by subtracting basal fluorescence from total fluorescence. Basal fluorescence was assigned to be the value calculated from linear trypan blue positivity-fluorescence intensity relationship, corresponding to 100% trypan blue positivity.

The assay was performed at least three times by repeating independent transfection or treatment. Student's t test was performed as the statistical analysis.

Radiolabeling of oligonucleotides for Northern blot analysis was performed using Renaissance 3' end labeling system (NEN) with terminal deoxynucleotidyl transferase (TdT). More specifically, 75 pmol of the probe oligonucleotide, 100 pmol of 3'-[$^{32}$p]-dATP (185 TBq/nmol, NEN), and 36 units of TdT were incubated at 37° C. for 30 minutes; and then, the labeled oligonucleotides were separated by gel filtration. $1 \times 10^6$ to $5 \times 10^6$ cpm/μl labeled probes were obatained according to the procedure. 5'-CTG CCC GCC TCT TCA CGG GCA GGT CAA TTT CAC TGG TTA AAA GTA AGA GAC AGC TGA ACC CTC GTG GAG CCA TGT GGT G-3' (SEQ ID NO: 3) was used as the antisense HN. The cDNA fragment was radiolabeled using Ready-To-Go random labeling system (Amersham Pharmacia). Specifically, after incubation of 50 to 500 ng of denatured DNA fragments and 1.85 MBq[α-$^{32}$p]dCTP for 30 minutes at 37° C.; the labeled DNA fragments were separated by gel filtration. About $5 \times 10^7$ cpm/μg DNA of labeled probes were obtained by the procedure. Northern blot analysis was performed using ExpressHyb (Clontech). More specifically, after prehybridization, membranes blotted with tissue polyA$^+$-RNA (human tissue membranes obtained from Clontech; mouse tissue membranes obtained from Origene) were soaked with radiolabeled probes (2 to $5 \times 10^7$ cpm) for 18 hours. After washing the membrane by two steps according to the directions, the membranes were exposed to X-ray films at −70° C. using two intensifying screens.

Example 1

Identification of Humanin

The F11 cell, established by fusing E17.5 rat primary cultured neurons and mouse neuroblastoma NTG18, is an immortalized cell model of primary cultured neurons (Platika, D. et al. (1985) Proc. Natl. Acad. Sci. U.S.A. 82, 3499-3503). Without a differentiation stimulus, the cell maintains typical characteristics of primary cultured neurons, such as the production of an activation potential (Platika, D. et al. (1985) Proc. Natl. Acad. Sci. U.S.A. 82, 3499-3503). The present inventor discovered that upon transfection of F11 cells with cDNA encoding V642I/F/G APP, i.e. three kinds of FAD causative genes, transient expression of V642 mutant APP causes cell death (Yamatsuji, T. et al. (1996) Science 272, 1349-1352). Accordingly, the present inventor used the recently developed ecdysone-inducible system (No, D. et al. (1996) Proc. Natl. Acad. Sci. U.S.A. 93, 3346-51) to construct F11 clones wherein the V642I APP is inducible. F11 cells wherein the expression of V642I APP can be induced were established as follows: first, F11 clones (F11/EcR) that overexpress both ecdysone receptor and RXR were established; and then, the cells were stably transfected with pIND-V642I APP, which encodes V642I APP cDNA that is expressed by an HSV promoter placed under the control of ecdysone responsive sequences. In their original form, F11/EcR/V642I clone cells established as above hardly expresses V642I APP. However, conditional overexpression of V642I APP from the cells due to ecdysone treatment was confirmed. Furthermore, in response to ecdysone treatment, cell death was induced in all of the F11/EcR/V642I cells; and cell mortality in all F11/EcR/V642I cells reached 60 to 70% after 72 hours from the treatment, and 80 to 90% after 96 hours from the treatment.

Using these cells, and basically following the method developed by D'Adamio et al. (D'Adamio, L. et al. (1997) Semin. Immunol. 9, 17-23), "death trap screening" was performed using a modified version of the method of D'Adamio et al. In the originally described "death trap screening", Vito et al. transfected Jurkat cells with normal T-cell cDNA library; induced cell death by stimulating T-cell receptors; and collected genes that antagonize cell death. The present inventor performed death trap screening in order to screen genes that antagonize cell death induced by AD genes. First, F11/EcR/V642I cells were transfected with mammalian expression cDNA library [cDNA was prepared from brain samples (occipital cortex) of Alzheimer patients; and the library was constructed using mammalian cell expression vector pEF-BOS, having the elongation factor promoter] (Mizushima and Nagata, 1990, Nucleic Acids Res. 18:5322); the cells were treated with ecdysone for 72 hours; and plasmids were collected from surviving cells. The procedure was repeated 3 times, and ultimately, plasmids of about 250 clones were obtained. The clones were categorized into 36 groups that cross hybridize to each other by dot blot hybridization using respective plasmids. The largest group comprised 28 clones.

Focusing on this group of cDNAs, the present inventor sequenced all the clones. As a result, clones belonging to this group generally consisted of a cDNA having a fused sequence of 1535 bp; specifically, 5' sequence homologous to the non-coding region of Wnt-13, a 3' sequence homologous to the mitochondrial 16S ribosomal RNA, and a poly(A) region at the C-terminus. The entire sequence was novel (FIG. 1). After sequencing each clone, whether the transient transfection of respective clones significantly suppresses cell death induced by ecdysone in F11/EcR cells co-transfected with pIND-V642I APP was assayed. As a result of comparing the sequences which demonstrated a cell death suppression activity, an antagonizing activity against cell death induced by V642I APP was found to be encoded by a 75 bp open reading frame (ORF) (5'-ATGGCTCCAC-GAGGGTTCAGCTGTCTCTTACTTTTAAC-CAGTGAAATTGACCTGCCCGTG AAGAG-GCGGGCATGA-3'/SEQ ID NO: 4) encoding a novel 24-amino acid polypeptide "MAPRGFSCLLLLT-SEIDLPVKRRA" (SEQ ID NO: 5). The present inventor dubbed the molecule Humanin (HN).

Example 2

Suppressive Effect of Respective Clones on Cell Death Induced by FAD Genes

FIGS. 2 to 4 demonstrate the effects of co-transfection of respective clones belonging to this group. When F11/EcR cells (F11 clone stably expressing EcR and RXR, wherein the expression of genes encoded by pIND plasmid are induced by ecdysone) were transiently transfected with pIND encoding V642I APP in the absence of ecdysone (non-V642I APP inducing conditions), 72 hours later, cell death occurred in about 20% of the cells, whereas cell death occurred in a significantly high proportion (50 to 50%) of cells in the presence of ecdysone (V642I APP inducing conditions) (FIG. 2). F11/EcR cells transfected with DT63-encoding pEF-BOS, in addition to V642I APP-encoding pIND, demonstrated no significant increase of cell death induced by ecdysone even in the presence of ecdysone. On the other hand, cells transfected with pEF-BOS or pEF-BOS encoding DT171, demonstrated significant increase in cell death in response to ecdysone. FIG. 3 demonstrates the result confirming the effect of DT63 on neuronal death induced by the four FAD genes (V642I APP, NL APP, M146L PS-1, and N141I PS-2), respectively, using simple transient transfection. When F11 cells were co-transfected with empty pEF-BOS in addition to the pcDNA encoding any one of FAD genes (V642I APP, NL APP, M146L PS-1, or N141I PS-2), incubation for 72 hours lead to cell death in 50 to 70% of the cells. The transfection efficiency under this condition was about 60 to 70%, which indicates that cell death occurred after 72 hours from transfection in most of the cells expressing one of the FAD genes. Increase in cell death was dramatically suppressed by transfecting F11 cells with DT63-encoding pEF-BOS in addition to one of the FAD genes. This indicates that, DT63 cDNA antagonizes cell death induced by the four AD genes with a high efficiency. FIG. 4 demonstrates the effect of other DT clones that contain the entire HN sequence, and other DT clones that do not contain the entire sequence (DT29, DT44, and DT171 cDNA). Although marked suppression of cell death induced by each of the FAD genes was demonstrated with DT29 and DT44, which are clones encoding the entire HN sequence, action of antagonizing cell death could not be confirmed with DT171 lacking the first ATG codon of HN. These data indicate that the ORF encoded by HN protects neurons from cell death caused by all four FAD genes.

Therefore, the present inventor subcloned HN cDNA into the pFLAG vector (pHN), and directly investigated the effect of pHN towards neuronal death caused by each of the FAD genes, V642I APP, NL-APP, M146L PS-1, and N141I PS-2. As expected, transfection of pHN into F11 cells hardly showed toxicity, and furthermore, detoxified the toxicity by the FAD genes (FIG. 5). The antagonizing activity is not the result of suppression of the expression of respective FAD genes by pHN. This is verified by the fact that co-transfected pHN doesn't change the expression of FAD genes expressed from the CMV promoter, which was indicated from the finding that pHN co-transfection didn't change the expression of EGFP expressed from the CMV promoter (data not shown. Furthermore, immunoblotting of V642I APP, NL-APP, and N141I PS-2 confirmed that co-transfection of pHN hardly has any effect on the expression of these genes (data not shown).

Example 3

Extracellular Secretion of HN

In the course of experiments, the culture supernatant of F11 cells transfected with pHN (CM/F11-pHN) was demonstrated to significantly suppress cell death induced by FAD genes encompassing V642I APP. Cell death was induced at high rates in F11 cells transfected with V642I APP cDNA under the presence of fresh media or culture supernatant of F11 cells transfected with empty pFLAG vector (CM/F11-vec), but in contrast, under the presence of CM/F11-pHN, cell death decreased dramatically in F11 cells transfected with V642I APP cDNA (FIG. 6). Similar results were obtained with DT clones. Complete suppression of V642I APP-induced cell death of F11 cells was observed with CM/DT29 and CM/DT63, but not with CM/DT171.

The result indicates that HN polypeptides transcribed from HN or cDNA encoding HN are secreted into the culture media to suppress cell death induced by V642I APP. FIG. 7 demonstrates the result of investigation on immunoreactivity of HN in CM/F11-pHN using anti-FLAG antibodies. CM/F11-pHN and the lysate of cells transfected with pHN showed a single band at 3 to 4 kDa, indicating immunoreactivity of HN, the size of wishich concordant with the expected molecular weight for FLAG-fused HN (3837 Da; FIG. 7, left and center panels). Concentration determination using synthetic FLAG-fused HN polypeptide (MAPRGFS-CLLLLTSEIDLPVKRRAGT<u>DYKDDDDK</u>: Flag tag is underlined) (SEQ ID NO: 6) demonstrated HN is present in CM/F11-pHN at a concentration of 8 to 9 μM (FIG. 7, right panel). These finding indicate that HN is transcribed from pHN and is secreted into the culture supernatant.

Example 4

HN Encodes Signal Sequence-like Activity 23 to 24 N-terminal residues of the entire 24 amino acids of the HN sequence satisfy the requirements necessary as a signal sequence (Nielsen, H. et al., 1999, Protein Eng. 12, 3-9; determination program provided at the SignalP World Wide Web server (CBS, the Technical University of Denmark)). The fact that intracellularly expressed HN is secreted into the culture media at micromolar concentrations suggests that HN has not a signal sequence activity itself, but has an activity similar to that of a signal sequence. Since the flag tag is positioned at the C-terminus, and the secreted HN polypeptide has a molecular weight concordant with the size expected for FLAG-fused HN, the entire HN sequence is suggested to encode a signal sequence-like secretion activity.

To confirm the hypothesis, the effect of L9R mutation, which should lead to loss of the signal sequence properties of the HN sequence, on HN secretion was investigated. As expected, the L9R mutant HN (HNR) (SEQ ID NO: 7) was expressed inside the cell transfected with the cDNA encoding the mutant, and secretion into the culture supernatant couldn't be observed (FIG. 8, top panel). The result demonstrates that the secretion activity of the signal sequence-like HN sequence is coded on the primary structure of HN. According to another investigation, the signal sequence activity of HN was investigated directly by fusing HN sequence to the N-terminus of EGFP (HN-EGFP). EGFP having HN fused to the N-terminus was secreted into the culture supernatant of transfected cells, but the original EGFP was not secreted at all to the outside the cell (FIG. 8, bottom panel). Similarly to EGFP, EGFP having HNR fused to the N-terminus was not secreted at all. These data demonstrate that HN itself encodes a signal sequence-like activity. This shows that HN is a unique secretory protein that encodes a signal sequence-like secretory activity and a biological activity at the same time.

Example 5

Suppressive Effect of Synthetic HN Polypeptide on Cell Death Induced by V642I APP Next, the present inventor synthesized a synthetic HN polypeptide MAPRGFSCLLLLTSETDLPVKRRA (SEQ ID NO: 5), and investigated its action on neuronal death induced by V642I APP by adding the polypeptide extracellularly. Cell death induced by V642I APP was dramatically suppressed by transfecting F11 cells with V642I APP cDNA and culturing the cells in the presence of 10 µM synthetic HN polypeptide (sHN) (FIG. 9). Only an extremely weak suppression was indicated at 10 nM sHN. The suppressive action was dependent on the concentration of sHN addded, and at the level of 1 to 10 µM polypeptide, complete suppression could be achieved. $IC_{50}$ value was about 100 nM. The dose-dependent curve agrees with the fact that HN secreted at a level of about 10 µM into CM/F11-pHN effectively suppressed cell death induced by V642I APP.

Example 6

Suppressive Effect of HN Polypeptide and Structural Derivatives Thereof on Cell Death Induced by V642I APP The present inventor further examined whether the cell death suppressive action of sHN is dependent on the specific primary structure (FIG. 9). A complete antagonizing effect on cell death induced by V642I APP could be observed at a concentration of 10 nM or less with S14G (MAPRGFS-CLLLLTGEIDLPVKRRA: the underlined G replaces S; called HNG) (SEQ ID NO: 8) as the polypeptide, and $IC_{50}$ of the polypeptide was about 100 pM. In contrast, C8A HN polypeptide (MAPRGFSALLLLTSEIDLPVKRRA: underlined A replaces C; called HNA) (SEQ ID NO: 9) did not significantly suppress cell death induced by V642I APP at concentrations up to 100 µM. The importance of Cys at position 8 was also suggested from the result obtained using an HN dimer (C8-C8 HN), bound through Cys at position 8. The antagonizing action level of C8-C8 HN was in between those of the original HN and HNA. On the contrary, a derivative wherein the HN C-terminal KRRA (residues 21-24 of SEQ ID NO: 9) was substituted with AAAA (residues 21-24 of SEQ ID NO: 10) indicated similar functional activity to the original HN polypeptide. These results indicate that the primary structure has a fundamental role in the suppression activity of HN, and that particular amino acid residues have a predetermined role.

Example 7

Suppressive Effect of HN Polypeptides and Structural Derivatives Thereof on Cell Death Induced by FAD Genes Next, the effect of sHN, synthetic HNG (sHNG), and synthetic HNA (sHNA) on cell death induced by other FAD genes, more specifically, those induced by NL-APP, M146L PS-1, and N141I PS-2 was investigated. As indicated in FIG. 10, the original sHN demonstrated similar dose-responsiveness on cell death induced by any of the three FAD genes, and blocked neuronal death induced by the FAD genes at a concentration of 1 µM. Up to a concentration of 100 µM, sHNA did not antagonize cell death by any of the FAD genes. In contrast, sHNG completely suppressed cell death caused by any of the FAD genes at a concentration of 10 nM or less. This indicates that the action of HN is enhanced 100 to 1000 fold by S14G substitution. Taking the action of sHNG on cell death induced by V642I APP (FIG. 9) together, sHNG at a concentration of 10 nM or less, completely antagonizes neuronal death induced by all of the four different types of FAD genes.

Example 8

Cell Death Suppressive Effect by the Transfection of Vectors Expressing HN and Structural Derivative Thereof Next, cell death suppressive effect of HNG or HNA-encoding plasmid (pHNG or pHNA, respectively) compared to pHN was investigated to confirm the data obtained from synthetic polypeptides. As demonstrated in FIG. 11, similarly to the case with pHN, co-transfection of pHNG completely suppressed cell death induced by all of the 4 types of FAD genes. In contrast, even though HNA polypeptides were produced and secreted into the media by pHNA co-transfection (FIG. 7), similarly to the cases with pHN and pHNG, suppression of cell death caused by any of the FAD genes couldn't be observed. These data obtained from each of the plasmids not only support the result of the previously mentioned polypeptide analysis, but also suggests that HNG concentration within CM/F11-pHNG (culture supernatant of F11 cells transfected with pHNG) exceeds 10 nM. Concordant with the result, according to the immunoblot analysis, the culture supernatant of F11 cells transfected with pHNG (CM/F11-pHNG) contained about 10 µM of HNG polypeptide (FIG. 7, right panle). These data indicate that the cell death suppression activity of HN is determined by its specific amino acid structure, and that the cell death suppression action caused by extracellularly adding HN polypeptides may be also caused by intracellularly expressing HN cDNA.

Example 9

Specificity of the Cell Death Suppressive Effect of HN

To elucidate the specificity of HN action, the ability of HN cDNA or HN polypeptide to antagonize cell death induced by causative genes of other neurodegenerative diseases was investigated. Polyglutamine Q79, having 72 repeats, is considered to be the cause of Huntington's disease (HD) and certain types of spinocerebellar ataxia (SCA) (Ikeda, H. et al. (1996) Nat. Genet. 13, 196-202; Kakizuka, A. (1997) Curro Opin. Neurol. 10, 28S-90). In accordance with the report that Q79 expression causes neuronal death, F11 cells underwent cell death due to the expression of Q79 (FIGS. 12A-12D). Examination of neurotoxicity was carried out in the presence or absence of ecdysone by transfecting F11/EcR cells with Q79 plasmid, the expression of which is induced by ecdysone (pDN-E/GSH-Q79). In this system, cell mortality markedly increased in response to ecdysone treatment when F11/EcR cells were transfected with pDN-E/GSH-Q79 together with the empty vector (pFLAG) (FIG. 12A). Similarly, high proportions of cell death of F11/EcR cells, transfected with pDN-E/GSH-Q79 together with pHN, pHNG, or pHNA, were induced by ecdysone treatment. Further, F11/EcR cell death caused by ecdysone-induced expression of any of the FAD gene was effectively suppressed by the co-transfection of pHN (FIG. 12B). Cell death induced by Q79 was not suppressed in the experiment using sHN (FIG. 12C). Extensive cell death was caused by ecdysone when F11/EcR cells were transfected with pDN-E/GSH-Q79, even in the presence of sHN, sHNG, or sHNA at a concentration of sHN or sHNG that enables complete suppression of F11/EcR cell death caused by anyone of the 4 types of FAD genes, just as in the absence of sHN, sHNG, or sHNA (FIG. 12D).

Additionally, the present inventor investigated the effect of HN on neuronal death induced by mutants of Cu/Zn-dependent superoxide dismutase (SOD1), i.e. A4T, G85R, or G93A, associated with familial amyotrophic lateral sclerosis (familial ALS). In accordance with previous reports reporting that expression of familial ALS-associated SOD1 mutants cause cell death of mammalian neurons (Rabizadeh, S. et al. (1995) Proc. Natl. Acad. Sci. U.S.A. 92, 3024-8; Ghadge, G. D. et al. (1997) J. Neurosci. 17, 8756-66), significant cell death was induced with all of the mutants by transfecting F11 cells with a cDNA that expresses one of the mutants. Further, a similar high cell mortality was induced when F11 cells were co-transfected with pHN in addition to each SOD1 mutant gene (FIG. 13A). As demonstrated in FIG. 13B, cell death caused by one of the familial ALS-associated SOD1 mutants couldn't be suppressed with 100 µM of any of sHN, sHNG, or sHNA. These data suggest that HN activates the intracellular mechanism for suppressing the cell death execution mechanism triggered by the FAD genes, but does not function on cell death caused by other neurodegenerative disease genes, and verify that the antagonizing effects on HN cDNA and HN polypeptides are common and specific to neuronal death associated with AD.

Example 10

Suppressive Effect of HN on Cell Death of Primary Neuronal Culture

The present inventor examined the protection of primary cultured neurons by HN from damages associated with AD. Aβ is the major peptide component of senile plaque and an extracellular deposit that pathologically characterizes an AD brain, and is suggested to be associated with the pathological mechanism of AD (Selkoe, D. J. (1994) J. Neuropathol. Exp. Neurol. 53, 438-47; Cummings, J. L. et al. (1998) Neurology 51, S2-17; discussion S65-67). Aβ treatment has been reported to induce cell death of primary cultured neurons (Loo, D. T. et al. (1993) Proc. Natl. Acad. Sci. U.S.A. 90, 7951-7955; Gschwind, M. and Huber, G. (1995) J. Neurochem. 65, 292-300). As demonstrated in FIG. 14, extensive cell death accompanied by dystrophic neuritic changes of the axon was induced in primary cultured cortical neurons treated with 25 µM Aβ1-43 for 48 to 72 hours in the presence or absence of N2 supplement. Cell death induced by Aβ, as well as dystrophic neuritic changes of the axon were dramatically suppressed in primary cultured neurons pre-treated with 10 µM sHN. Cell death (measured by trypan blue exclusion; FIG. 15, left panel) and cell damage (measured by LDH released from the cells; FIG. 16) was observed by the treatment with Aβ1-43. These indices of cell survival (i.e., cell death and cell damage) were completely restored to a level observed under basal conditions by the treatment with 10 µM sHN. Under the same conditions, 100 ng/ml of NGF did not show effects to antagonize increased LDH release and cell death of neurons induced by Aβ (data not shown). In spite of the fact that sHN demonstrated a dramatic effect in antagonizing neuronal death induced by Aβ, similar treatment of neurons with 10 µM sHN could not prevent the toxic effect of 20 µM etoposide on primary cultured neurons (FIG. 15, right panel; and FIG. 16). Etoposide is an anticancer agent and has been reported to induce cell death of primary cultured neurons (Nakajima, M. et al. (1994) Brain Res. 641, 350-2). These findings support the idea that HN antagonizes neuronal death induced by Aβ1-43 by a selective mechanism. As indicated in the experiment of FAD genes using F11 cells, 10 nM sHNG completely protected cells from cell death and dystrophic neuritic changes of the axon caused by Aβ1-43, but 10 nM sHN or 10 µM sHNA both did not show any effect against neurotoxicity of Aβ (FIG. 14). The result was confirmed not only by the LDH release assay (FIG. 16), which is an assay of cell damage, and by trypan blue exclusion assay (FIG. 15), but also by Calcein staining assay (FIGS. 17 and 18), which is an assay of viable cells. Thus, HN was shown to have similar effects on primary cultured neurons as on cloned neurons. Furthermore, these data suggest the existence of a receptor (group of receptors) that specifically recognizes the HN structure, common between F11 cells and primary cultured neurons.

Example 11

Expression of HN mRNA

Using β-actin mRNA as a positive control, expression of HN mRNA in various tissues were examined. From Northern blot analysis of human tissues, remarkable HN mRNA expression was detected in the heart, skeletal muscles, kidneys, and liver (FIG. 19a). Although less than in those tissues above, a significant expression was detected in the brain and in the gastrointestinal tract. In the immune system, including the thymus, spleen and peripheral leukocytes, mRNA was hardly detected. The size of the mainly expressed mRNA was about 1.6 kb which corresponds to the size expected for the longest DT cDNA comprising HN. Additionally, mRNAs of different sizes of about 3 kb and about 1 kb were also detected. Similar results as those mentioned above were obtained and all of the bands were detected when DT77, encoding the 3' region of HN but not the HN (see FIG. 11, or an antisense primer (GGGTGT-TGAGCTTGAACGC/SEQ ID NO: 11) against the 5' region, −440 to −422, of HN was used as a probe. Thus, the mRNAs are expected to be full length HN mRNA and splicing variants thereof. The present inventor isolated several cDNAs from human heart cDNA library. The size of the isolated cDNAs exceeded 1 kbp, and the positions of the cDNAs were substantially the same as those of DT44. Similar results, except for the differences mentioned below, were obtained in mouse tissues (FIG. 20). A difference was that the skeletal muscle and liver of mouse had lower levels of HN mRNA compared to human tissues. However, quantitative differences seemed to be affected by conditions of the individuals, since the HN mRNA level was higher in skeletal muscles and liver of other mice (data not shown). Another difference was that the small 1 kb mRNA was expressed at an amount comparable or greater to the amount of the 1.6 kb mRNA in mouse heart and kidneys. Further, an additional mRNA of about 0.4 kb was specifically expressed in mouse brain, heart, and skeletal muscles. Detailed analysis of the expression regions in the brain revealed that comparatively large amounts of mRNA were expressed in the cerebellum and in the occipital lobe among the brain regions. These results indicate that HN mRNA is mainly produced in organs other than the central nervous system. Therefore, HN is possibly secreted into the blood stream, and is transported to the cranial nerves. Alternatively, locally synthesized HN in the brain may exhibit a protective action. It is interesting to note that most of the HN mRNA is synthesized in the cerebellum and occipital lobe, which are regions demonstrating strongest resistance against neuronal death in AD brains.

Example 12

Effect of Secretion-defective Mutant of HN

It is clear from the data above that extracellularly added HN polypeptides act from outside of the cell. However, the possibility that HN polypeptides taken in from the cell surface exhibit effects inside the cell cannot be denied. HN may act inside ER as reported for the cell death of a primary cultured neurons caused by Aβ1-40, which is mediated by caspase-12, the main caspase existing in the endoplasmic reticulum (ER) (Nakagawa, T. et al. (2000) Nature 403, 98-103). When HN acts inside ER, HN synthesized in ER should be able to produce protective signals in situ. Accordingly, secretion-defective mutant L9R HN was used to verify the hypothesis.

F11 cells transfected with V621I APP cDNA and L9R HN (HNR) cDNA demonstrated high cell mortality, similar to that in cells transfected with V621I APP cDNA alone (Table 1, right column). Cell death of cells transfected with V621I APP cDNA and HNR cDNA was completely suppressed when sHN was present in the culture media, which confirmed the lack of protective activity of intracellularly expressed HNR. In contrast, it was demonstrated that transfection with V642I APP cDNA under the same conditions doesn't induce cell death when sHNR is added extracellularly (Table 1, left column). HNR translated from HNR cDNA in ER is not secreted into the culture media (FIG. 8, top panel). Thus, HN polypeptide has to exist outside and not inside of the cell to exert the function of HN to rescue cells. These data show that HN can only exhibit its effect by acting from outside of the cell.

TABLE 1

| | | | |
|---|---|---|---|
| no transfection | 13.2 ± 0.7 | pcDNA + pFLAG | 10.3 ± 2.0 |
| pcDNA | 11.5 ± 0.6 | V642I APP + pFLAG | 52.2 ± 1.5* |
| V642I APP | 53.7 ± 2.3 | V642I APP + pHN | 17.6 ± 2.2 |
| V642I APP + sHN | 14.4 ± 1.2* | V642I APP + pHNA | 53.2 ± 0.6 |
| V642I APP + sHNA | 52.5 ± 3.0 | V642I APP + pHNR | 52.0 ± 2.1** |
| V642I APP + sHNR | 17.7 ± 2.2* | V642I APP + pHNR + sHN | 15.3 ± 2.0* |

(F11 cells transfected with pcDNA or V642I APP cDNA, were simultaneously co-transfection with pFLAG or pHN plasmid (right), or were treated with 10 μM sHN polypeptides (left). 72 hours after cultivation, cell mortality (%) was measured by trypan blue exclusion assay. The values are indicated as mean ±S.D. values of three independent transfections and treatments.
*significant suppression on cell death induced by V642I APP ($p < 0.01$);
**no significant suppression on cell death induced by V642I APP)

Example 13

Detailed Structure/Function Relationship of the Protective Activity of HN

Detailed relationship between the primary structure and protective activity of HN was investigated. FIG. 21 demonstrates the result of analysis examining whether a truncated HN polypeptide antagonizes V642I APP. F11 cells were transfected with V642I APP cDNA and were cultured in the presence of 10 μM HN derivative. Hardly any effect on cell protective activity was observed by the deletion of two N-terminal residues from the HN polypeptide in the system. On the other hand, activity of HN disappeared by a deletion of three residues from its N-terminus. This suggests that although Met-Ala at the N-terminal end is not necessary, the third Pro is essential for the activity. According to a similar experiments on the deletion of the C-terminus, as demonstrated in FIG. 21, Val-Lys-Arg-Arg-Ala (residues 20-25 of SEQ ID NO: 42) at the C-terminal end is not necessary whereas the nineteenth Pro was essential for maintaining the complete protective activity of HN. Therefore, the minimum region required for maximum activity is from Pro3 to Pro19, which was dubbed HN-17 (SEQ ID NO: 21).

The top panel on the left of FIG. 22 demonstrates the effect of HN lacking the three N-terminal residues (ΔN3) and HN-17 on neuronal death induced by the four FAD genes. HN-17 demonstrated a sufficient antagonizing activity on cell death induced by all of the three FAD genes other than the above-mentioned V642I APP, whereas ΔN3 peptide show no activity on cell death by any of the genes. The other panels of FIG. 22 demonstrate the dose-response relationship of the effect of synthetic HN-17 on neuronal death induced by each of the four FAD genes. Although HN-17, compared to the original HN, had slightly lower activity to suppress cell death induced by M146L PS-1, and required higher concentrations for the activity, low μM HN-17 exhibited a common sufficient protective action against cell death by any of the four FAD genes. The result suggests that the two N-terminal residues and the five C-terminal residues are not necessary for the common protective action.

Further, it was verified whether the HN-17 residues are essential for the HN-17 protective action. First, 10 nM S14G HN-17 (HNG-17) (SEQ ID NO: 24) was demonstrated to completely antagonize cell death of F11 cells induced by the four FAD genes and of primary cultured neurons by Aβ-1-43, similar to the case using 10 nM HNG. Then, HNG-17 derivatives (SEQ ID NO: 25 to 41), wherein each of the residues from Pro3 to Pro19 of HNG-17 was substituted with Ala one at a time, were synthesized; and the effect of the derivatives on cell death of primary cultured neurons induced by 25 μM Aβ1-43 was examined. FIG. 23 demonstrates the result of testing on cell death suppressive effect of each Ala-substituted HNG-17 derivative. The substituted residues are indicated below the graph, that indicates cell mortality values. According to the examination, seven residues essential for neuronal protection against cell death induced by Aβ were clearly identified: Pro at position 3; Cys at position 8; Leu at position 9; Leu at position 12; Thr at position 13; Gly at position 14 (originally Ser); and Pro at position 19. The role of other residues are not denied in the examination, but was demonstrated to be replaceable with Ala without affecting the protective activity. The result, that Pro at position 3, Cys at position 8, Gly at position 14, and Pro at position 19 is essential for the activity, agrees with the data obtained by the HN deficiency experiments (FIG. 21) and the HN amino acid residue replacement experiments described above (FIGS. 9 and 10). It is notable that substitution of Ser at position 14 to Gly enhances the protective activity whereas substitution to Ala results in loss of the protective activity. This indicated that slight changes of specific residues and side chains enhances or decreases the protective activity of HN against Aβ1-43.

The other panels of FIG. 23 demonstrate the results of examination on the effect of Ala-substituted (Ala-scanned) HNG-17 against cell death of F11 neurons induced by each of the four FAD genes. According to the data, residues having essential roles in antagonism were exactly the same as those necessary for antagonizing cell death of primary cultured neurons induced by Aβ. This suggests that HN protects neurons from a wide spectrum of AD damages through a common mechanism. The 7 essential residues may maintain some kind of secondary structure necessary for the recognition by a specific mechanism (receptors, and such) on the cell surface.

The superior ability of HN and HNG activity, and the fact that the activity strictly depends on the primary structure suggests the existence of a specific receptor. Antagonism of HN against neuronal death induced by the four FAD genes and by Aβ1-43 indicated extremely similar dose-response characters, as mentioned above, which also support the hypothesis (existence of a specific receptor). The dose-response character was also observed for both HN derivatives having positive (S14G) and negative (C8A) functions. Detailed analysis of the structure/function relationship verified that the regions and residues of HN necessary for the antagonism against these various AD damages precisely coincide in all types of HN. Furthermore, experiments on the secretion ability-defective mutant revealed that extracellular secretion of HN is essential for exhibiting the protective activity. These data indicate that the action of HN is caused from outside of the cell through specific cell surface receptors.

Example 14

Production of C8-substituted HNG

HN peptide has a crysteine (Cys) as the eighth residue, and substitution of this Cys with alanine (Ala) caused loss of activity as mentioned above. Moreover, the dimer form (C8-C8) sHN, which lacks the SH group of Cys at position 8, had decreased antagonizing activity on cell death. This suggests that modifications of the SH group of Cys residue corresponding to the position 8 of the HN peptide affect the cell death antagonizing activity of the peptide. Many enzymes, that can modify the SH group of a Cys residue, exist in blood and human body tissue. Thus, for clinical applications of a polypeptide of the invention, such polypeptides that do not contain a Cys residues, or wherein the modification of the SH group of the Cys residue does not affect the activity of the polypeptide are preferably. Therefore, mutant polypeptides, wherein the Cys at position 8 of HNG polypeptide was substituted with other amino acids, were produced and the antagonizing activity of these mutant polypeptides on cell death was measured.

F11 cells in their original form, or F11 cells transfected with V642I-APP cDNA (1 μg) were treated with any one of the mutated HNG polypeptides (10 nM), which Cys at position 8 (C8) was substituted with one of the 19 other possible amino acid residues. 72 hours after transfection initiation, cell mortality was measured by trypan blue exclusion assay. The results demonstrated that polypeptides, whose C8 was substituted with basic amino acids, such as His (SEQ ID NO: 46), Lys (SEQ ID NO: 48), or Arg (SEQ ID NO: 54), indicated significant suppression activity on neuronal death (FIG. 24, top panel).

Next, the antagonizing activity of mutated polypeptides on cell death induced by FAD genes other than V642I-APP cDNA was examined. F11 cells in their original form or upon transfection with 1 μg of FAD genes (K595N/M596L-APP, M146L-PS-1, or N141I-PS-2 cDNA) were treated with any one of the mutated HNG polypeptides (10 nM), whose C8 was substituted with another amino acid. 72 hours after transfection initiation, cell mortality was measured by try-pan blue exclusion assay. As a result, mutated HNG polypeptide whose C8 was substituted with a basic amino acid, such as His, Lys, or Arg, inhibited neuronal death of F11 cells, as expected. The characteristic of the inhibition activity was similar to that observed in cells transfected with V642I-APP cDNA (FIG. 24, center panel).

Furthermore, effect of the mutated polypeptides on cell death of primary cultured cortical neurons induced by Aβ was also examined. In the presence of any one of the mutated HNG polypeptides (10 nM), wherein C8 has been substituted with other amino acid residues, primary cultured cortical neurons were treated with 25 μM Aβ1-43. 72 hours after the initiation of Aβ treatment, cell mortality was measured by trypan blue exclusion assay, and assay of viable cells were performed by Calcein staining. As a result, substituted polypeptides, wherein the C8 was substituted with His, Lys, or Arg, suppressed cell death of primary cultured cortical neurons induced by Aβ, similar to that indicated above (FIG. 24, lower panel). Mutant HNG polypeptides wherein the C8 was substituted with Lys or Arg demonstrated a strong neuronal death suppression activity in all type of cell deaths comparable to the original HNG polypeptide. Those polypeptides, wherein the C8 was substituted with His, showed slight decrease in the cell death suppression activity. These results demonstrate that the Cys residue of the polypeptide of this invention can be substituted with other amino acids that do not have a SH group, and that substitution to basic amino acids, such as His, Lys, and Arg, preferably to Lys or Arg is useful.

Example 15

Production of HNG Derivatives

Enhancement of the HNG action by mutation of HNG (S14G HN) was verified. According to an experiment, examining the neuroprotective action of HNGs wherein multiple amino acid residues are substituted with other amino acids, polypeptides with higher rescue activity compared to HNG were obtained by mutating two positions, R4A/F6A (SEQ ID NO: 60). The polypeptide, dubbed AGA-HNG, not only completely rescued cell death of nerve cell line induced by FAD genes at a concentration as little as 0.1 nM, but completely rescued cell death of primary cultured neurons by Aβ at a concentration of 0.3 nM FIGS. 25A-25F. Arg and Phe at position 4 and 6 of HNG, respectively, are positions which are cleaved by trypsine-like protease and chymotrypsin-like protease, respectively (see FIG. 25A). Thus, it is likely that R4A/F6A substitution of HNG enhances resistance to degradation. A remarkable high activity for AGA-HNG is implied by the fact that AGA-HNG detoxifies the neurotoxicity of Aβ of high concentration, a 100000-fold higher concentration than AGA-HNG. Anti-AD agent that has such a broad spectrum with high neuroprotective action has not been reported so far. Application of AGA-HNG or derivatives thereof to chemotherapy of AD is expected.

Industrial Applicability

The present invention provides Humanin polypeptide, which has the ability to antagonize neurodegeneration associated with Alzheimer's disease. The polypeptide is the first molecule which has the ability to antagonize cell death of neurons induced by four kinds of FAD genes and Aβ. Further, the polypeptide can antagonize cell death of cloned neurons induced by V642I APP, NL-APP, PS-1 mutants, and PS-2 mutants, and cell death of primary cultured neurons induced by Aβ1-43. Protective factors acting extracellularly and possessing a wide spectrum, antagonizing Aβ and all of the known types of early onset FAD genes, had never been characterized before. Usefulness of HNG for elucidating the mechanism of neuronal death associated with Alzheimer's disease, as well as the extreme usefulness of HNG for clinical applications was particularly demonstrated by the fact that neurotoxicity associated with AD is completely antagonized with 10 nM or less of HNG. The protective action of HNG is extremely high, and HNG has generality and stringent specificity. Therefore, HNG, AGA-HNG, and derivatives generated thereof are extremely useful as pharmaceuticals to prevent neuronal death associated with Alzheimer's disease, and as seed compounds for the development of new pharmaceuticals for Alzheimer's disease.

The invention claimed is:

1. An isolated polypeptide that suppresses neuronal death associated with Alzheimer's disease having an amino acid sequence of Formula (I):

Pro-$Xn_1$-(Cys/bXaa)-(Leu/Arg)-$Xn_2$-Leu-Thr-(Gly/Ser)-$Xn_3$-Pro (I) (SEQ ID NO: 63)

wherein "Cys/bXaa" indicates Cys or a basic amino acid; "(Leu/Arg)" indicates Leu or Arg; "(Gly/Ser)" indicates Gly or Ser; and $Xn_1$, $Xn_2$, and $Xn_3$ independently indicate arbitrary amino acid sequences not more than 10 residues in length, respectively.

2. An isolated polypeptide selected from the group consisting of:
   (a) a polypeptide having an amino acid sequence selected from the group consisting of SEQ ID NOs: 5 to 8, 10, 12, 13, 21 to 24, 26 to 29, 32, 33, 37 to 40, 46, 48, 54, and 60 and
   (b) a polypeptide that suppresses neuronal death associated with Alzheimer's disease having an amino acid sequence which differs from a polypeptide of SEQ ID NOs: 5 to 8, 10, 12, 13, 21 to 24, 26 to 29, 32, 33, 37 to 40, 46, 48, 54, and 60, in such a way that one amino acid has been substituted, deleted, inserted, or added.

3. A fusion polypeptide comprising the polypeptide of any of claims 1 to 2 fused with one or more other polypeptides.

4. An isolated DNA encoding a polypeptide selected from the group consisting of:
   (a) a polypeptide that suppresses neuronal death associated with Alzheimer's disease having the amino acid sequence of Formula (I):
   Pro-$Xn_1$-(Cys/bXaa)-(Leu/Arg)-$Xn_2$-Leu-Thr-(Gly/Ser)-$Xn_3$-Pro (I) (SEQ ID NO: 63)
   wherein "Cys/bXaa" indicates Cys or a basic amino acid; "(Leu/Arg)" indicates Leu or Arg; "(Gly/Ser)" indicates Gly or Ser; and $Xn_1$, $Xn_2$, and $Xn_3$ independently indicate arbitrary amino acid sequences not more than 10 residues in length, respectively;
   (b) a polypeptide comprising an amino acid sequence which differs from a polypeptide of SEQ ID NOs: 5 to 8, 10, 12, 13, 21 to 24, 26 to 29, 32, 33, 37 to 40, 46, 48, 54, and 60 in such a way that one amino acid has been substituted, deleted, inserted, or added, wherein the polypeptide suppresses neuronal death associated with Alzheimer's disease;
   (c) a polypeptide comprising an amino acid sequence selected from the group consisting of SEQ ID NOs: 5 to 8, 10, 12, 13, 21 to 24, 26 to 29, 32, 33, 37 to 40, 46, 48, 54, and 60; and
   (d) a fusion polypeptide comprising the polypeptide of (a) or (c) fused with one or more other polypeptides;
   wherein the DNA does not comprise the sequence of SEQ ID NO: 4.

5. A vector into which a DNA encoding a polypeptide of any one of (a) to (c) is inserted:
   (a) a polypeptide that suppresses neuronal death associated with Alzheimer's disease having the amino acid sequence of Formula (I):
   Pro-$Xn_1$-(Cys/bXaa)-(Leu/Arg)-$Xn_2$-Leu-Thr-(Gly/Ser)-$Xn_3$-Pro (I) (SEQ ID NO: 63)
   wherein "Cys/bXaa" indicates Cys or a basic amino acid; "(Leu/Arg)" indicates Leu or Arg; "(Gly/Ser)" indicates Gly or Ser; and $Xn_1$, $Xn_2$, $Xn_3$ independently indicate arbitrary amino acid sequences not more than 10 residues in length, respectively;
   (b) a polypeptide comprising an amino acid sequence which differs from a polypeptide of SEQ ID NOs: 5 to 8, 10, 12, 13, 21 to 24, 26, to 29, 32, 33, 37 to 40, 46, 48, 54, and 60 in such a way that one amino acid has been substituted, deleted, inserted, or added, wherein the polypeptide suppresses neuronal death associated with Alzheimer's disease;
   (c) a polypeptide comprising an amino acid sequence selected from the group consisting of SEQ ID NOs: 5 to 8, 10, 12, 13, 21 to 24, 26 to 29, 32, 33, 37 to 40, 46, 48, 54, and 60; and
   (d) a fusion polypeptide comprising the polypeptide of (a) or (b) fused with one or more other polypeptides.

6. A host cell retaining the vector of claim 5.

7. A method for producing the polypeptide of any one of claims 1 to 2 or a fusion polypeptide comprising the polypeptide of any one of claims 1 to 2, comprising:
   culturing a host cell retaining a vector into which a DNA encoding the polypeptide of any one of claims 1 to 2, or a fusion polypeptide comprising the polypeptide of any one of claims 1 to 2 fused with one or more other polypeptides, is inserted; and
   recovering an expressed polypeptide from the host cell or culture supernatant thereof.

8. A pharmaceutical composition comprising the polypeptide of any one of claims 1 to 2.

9. The polypeptide of claim 1, wherein $Xn_1$ is an amino acid sequence consisting of 3 to 5 arbitrary amino acids, $Xn_2$ is an amino acid sequence consisting of 1 to 3 arbitrary amino acids, and $Xn_3$ is an amino acid sequence consisting of 3 to 5 arbitrary amino acids.

10. The polypeptide of claim 1, wherein the polypeptide comprises an amino acid sequence of SEQ ID NO: 101.

11. The polypeptide of claim 1, wherein the polypeptide comprises an amino acid sequence of SEQ ID NO: 102.

12. The polypeptide of claim 2, wherein the polypeptide comprising an amino acid sequence selected from the group consisting of SEQ ID NOs: 5 to 8, 10, 12, 13, 21 to 24, 26 to 29, 32, 33, 37 to 40, 46, 48, 54, and 60.

13. The DNA of claim 4, wherein $Xn_1$ is an amino acid sequence consisting of 3 to 5 arbitrary amino acids, $Xn_2$ is an amino acid sequence consisting of 1 to 3 arbitrary amino acids, and $Xn_3$ is an amino acid sequence consisting of 3 to 5 arbitrary amino acids.

14. The DNA of claim 4, wherein the DNA encodes a polypeptide comprising an amino acid sequence of SEQ ID NO: 101.

15. The DNA of claim 4, wherein the DNA encodes a polypeptide comprising an amino acid sequence of SEQ ID NO: 102.

16. The DNA of claim 4, wherein the DNA encodes a polypeptide comprising an amino acid sequence selected from the group consisting of SEQ ID NOs: 6 to 8, 10, 24, 26 to 29, 32, 33, 37 to 40, 46, 48, 54, and 60.

17. The vector of claim 5, wherein $Xn_1$ is an amino acid sequence consisting of 3 to 5 arbitrary amino acids, $Xn_2$ is an amino acid sequence consisting of 1 to 3 arbitrary amino acids, and Xn$_3$ is an amino acid sequence consisting of 3 to 5 arbitrary amino acids.

18. The vector of claim 5, wherein the DNA encodes a polypeptide comprising an amino acid sequence of SEQ ID NO: 101.

19. The vector of claim 5, wherein the DNA encodes a polypeptide comprising an amino acid sequence of SEQ ID NO: 102.

20. The vector of claim 5, wherein the DNA encodes a polypeptide comprising an amino acid sequence selected from the group consisting of SEQ ID NOs: 5 to 8, 10, 12, 13, 21 to 24, 26 to 29, 32, 33, 37 to 40, 46, 48, 54, and 60.

21. A composition comprising a polypeptide of claim 2, and a carrier.

* * * * *

UNITED STATES PATENT AND TRADEMARK OFFICE
CERTIFICATE OF CORRECTION

PATENT NO. : 7,314,864 B1 Page 1 of 1
APPLICATION NO. : 10/088724
DATED : January 1, 2008
INVENTOR(S) : Ikuo Nishimoto It is certified that error appears in the above-identified patent and that said Letters Patent is hereby corrected as shown below:

Column 22, line 63: the "A" in ARGFSCLLLLTGEIDLP should be underlined, to read -- <u>A</u>RGFSCLLLLTGEIDLP --

Column 23, line 54: "Priamry" should read -- Primary --

In claim 5(b) (column 84, line 13):
"8, 10, 12, 13, 21 to 24, 26, to 29, 32, 33, 37 to 40, 46," should read -- 8, 10, 12, 13, 21 to 24, 26 to 29, 32, 33, 37 to 40, 46, --

Signed and Sealed this

Fifteenth Day of July, 2008

JON W. DUDAS
*Director of the United States Patent and Trademark Office*